United States Patent
Sundström

(10) Patent No.: US 8,128,637 B2
(45) Date of Patent: Mar. 6, 2012

(54) DEVICE FOR REMOVING ACROCHORDONS

(75) Inventor: Staffan Sundström, Helsingborg (SE)

(73) Assignee: TagAway Devices ApS, Rungsted Kyst (DK)

( * ) Notice: Subject to any disclaimer, the term of this patent is extended or adjusted under 35 U.S.C. 154(b) by 603 days.

(21) Appl. No.: 11/758,396

(22) Filed: Jun. 5, 2007

(65) Prior Publication Data

US 2007/0276353 A1 Nov. 29, 2007

Related U.S. Application Data

(63) Continuation of application No. PCT/IB2005/054334, filed on Dec. 20, 2005.

(30) Foreign Application Priority Data

Dec. 21, 2004 (SE) ........................................ 0403102

(51) Int. Cl.
*A61B 17/50* (2006.01)
(52) U.S. Cl. .......................... 606/131; 606/151; 606/157
(58) Field of Classification Search .................. 606/131, 606/157, 134, 139, 151, 140; 604/304, 306, 604/307, 500; 602/41, 52, 54; 523/118; 128/894
See application file for complete search history.

(56) References Cited

U.S. PATENT DOCUMENTS

| 4,444,187 | A | | 4/1984 | Perlin |
| 5,158,563 | A | | 10/1992 | Cosman |
| 5,578,047 | A | * | 11/1996 | Taylor ............................ 606/157 |
| 6,066,147 | A | | 5/2000 | Mears |
| 2003/0087960 | A1 | * | 5/2003 | Burstein ........................ 514/557 |
| 2006/0259042 | A1 | | 11/2006 | Ali Hassanien |
| 2006/0282104 | A1 | | 12/2006 | Williamson, IV et al. |
| 2008/0319475 | A1 | | 12/2008 | Clark et al. |

FOREIGN PATENT DOCUMENTS

| EP | 1430840 A2 | | 6/2004 |
| GB | 2 322 802 A | | 9/1998 |
| GB | 2322802 A | * | 9/1998 |
| JP | 2003-144442 | | 5/2003 |
| WO | WO 99/47048 | | 9/1999 |
| WO | 0135832 A2 | | 5/2001 |
| WO | WO 2005/039421 | | 5/2005 |
| WO | 2006067743 A2 | | 6/2006 |

OTHER PUBLICATIONS

Robert A Schwartz et al., "Acrochordon", WebMD, last updated May 11, 2005.
Mark C. Luba et al., "Common Benign Skin Tumors", American Family Physician, vol. 67, No. 4, Feb. 15, 2003, pp. 729-738.
International Search Report, mailed Jul. 5, 2011, from related International Application No. PCT/IB2011/000265, filed Feb. 1, 2011.

* cited by examiner

*Primary Examiner* — Ryan Severson
*Assistant Examiner* — Tin Nguyen
(74) *Attorney, Agent, or Firm* — Winston & Strawn LLP

(57) ABSTRACT

The invention relates to a device for removal of bothersome acrochordons or skin tags from the skin. The device has an adhesive surface which allows manipulation and locking of the skin tag in such a way that acrochordon ectomic strangulation can occur without anesthetic or risk for bleeding or infections. The device includes three parts with one or several surfaces, the edges of which can be pivoted, folded, rotated or bent in relation to each other, whereby a more or less elastic strangulation of the skin tag causes an occlusion of the blood flow. The skin tag is simultaneously sealed to the skin surface and concealed by the device which makes the painless ectomic process cosmetically acceptable.

7 Claims, 63 Drawing Sheets

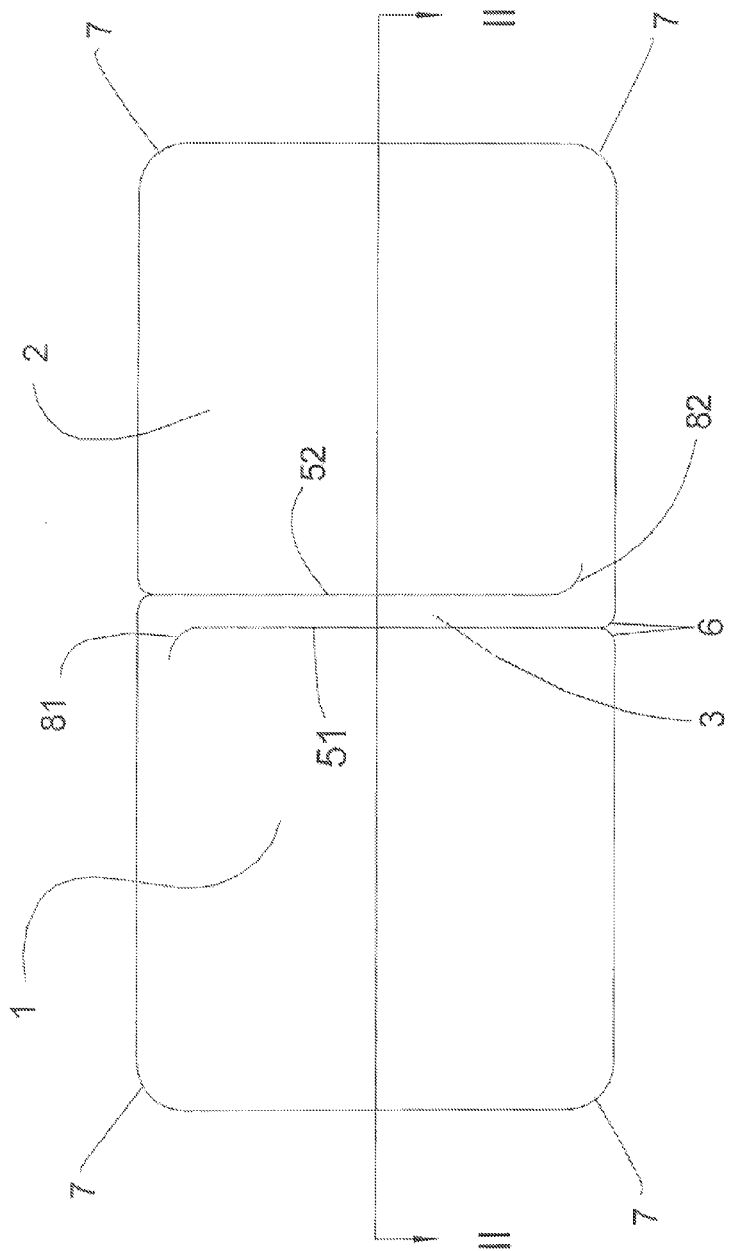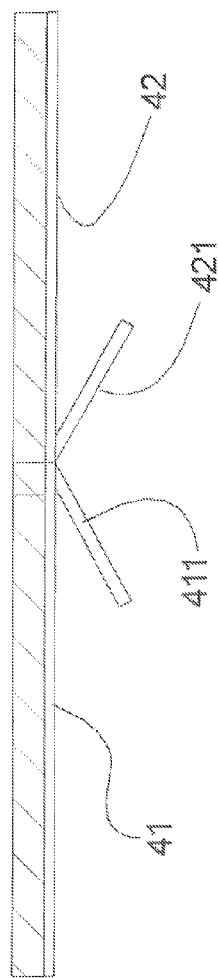

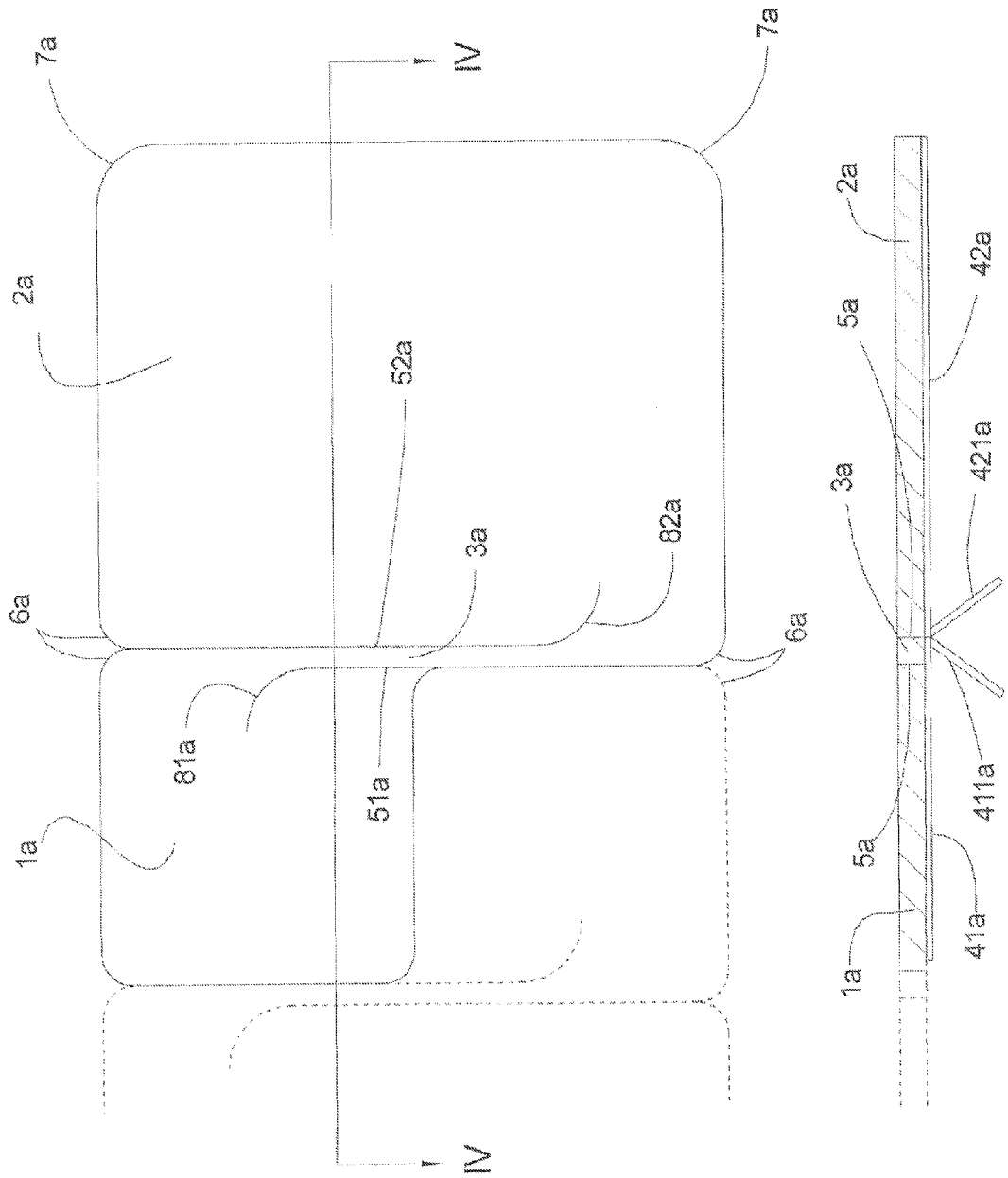

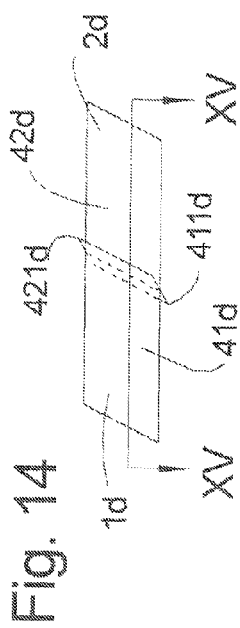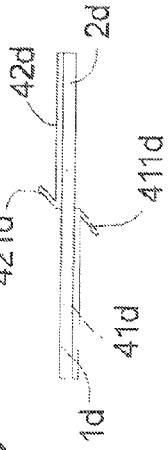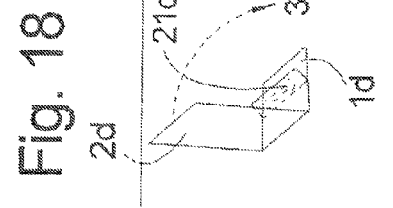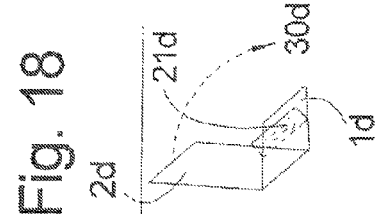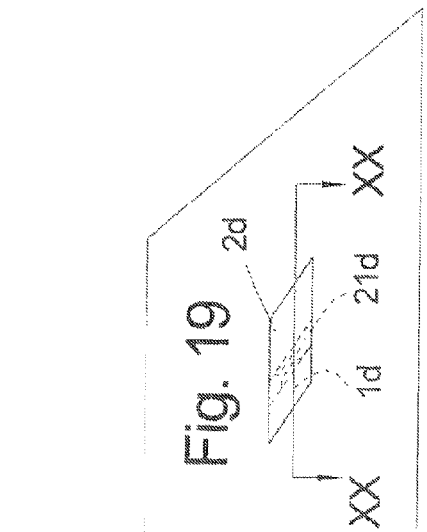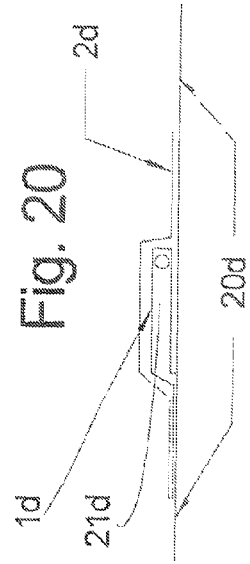

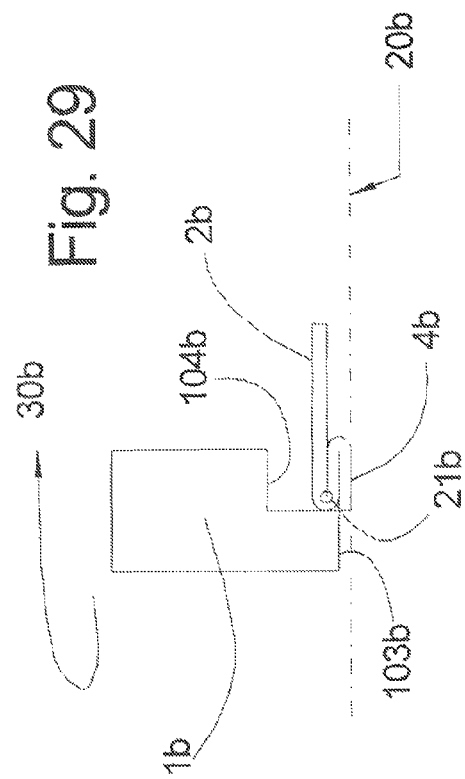
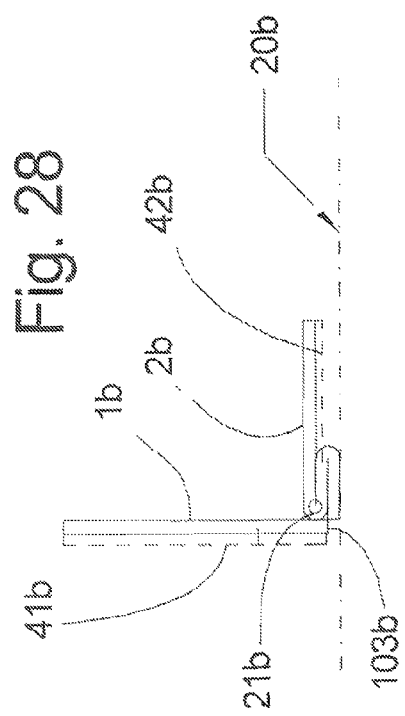
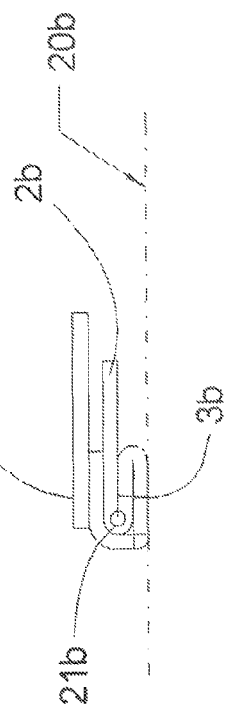

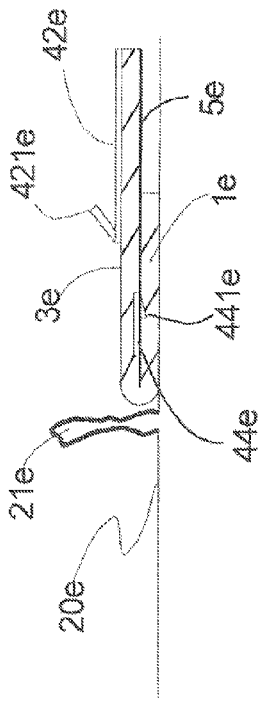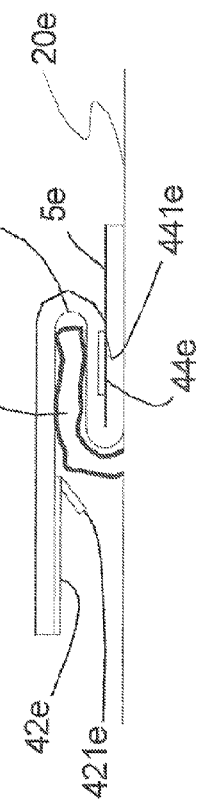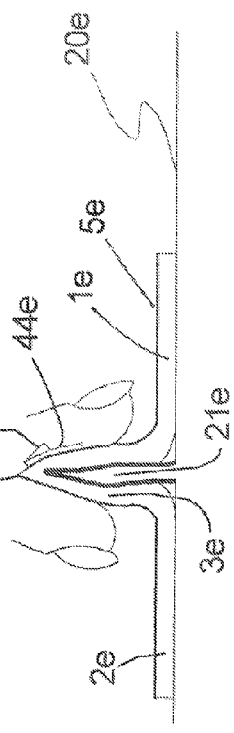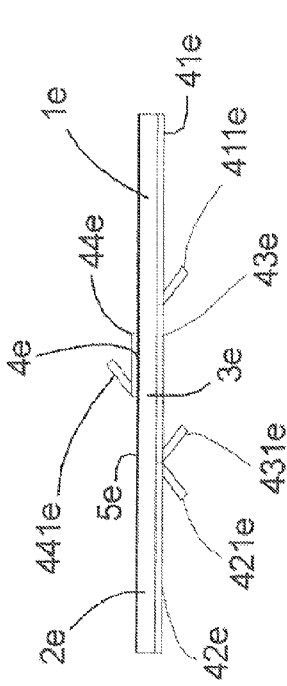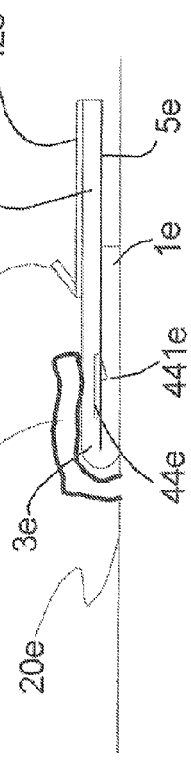

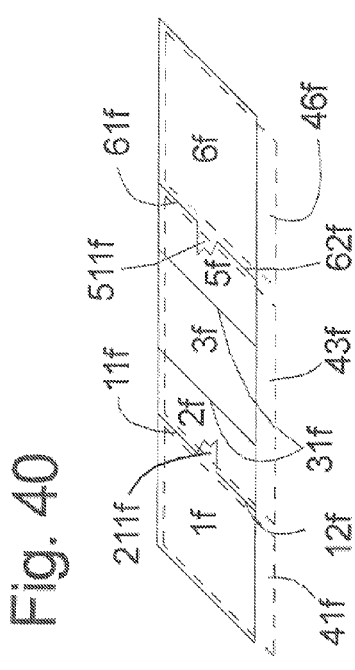
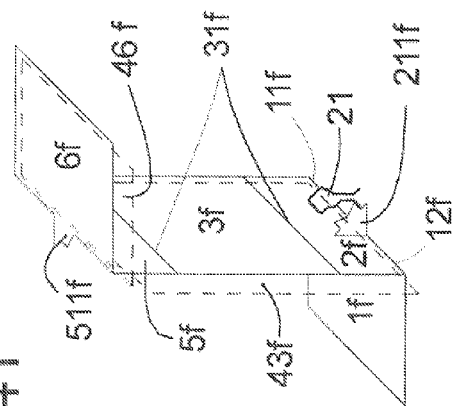
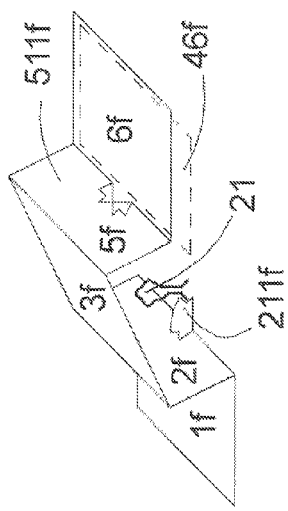
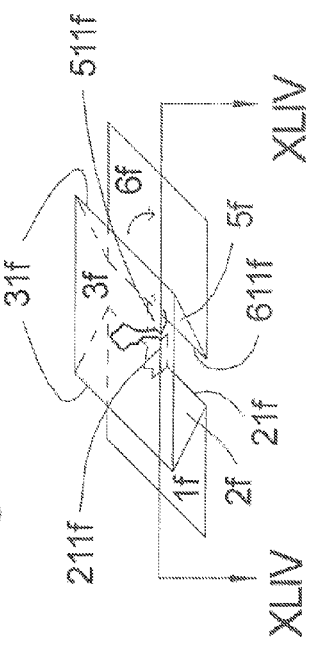
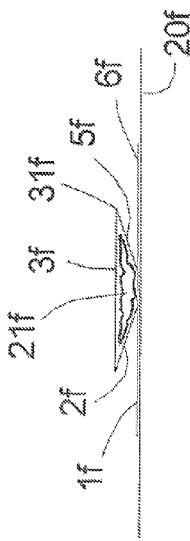

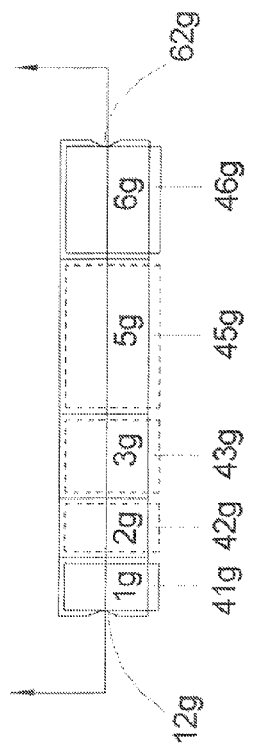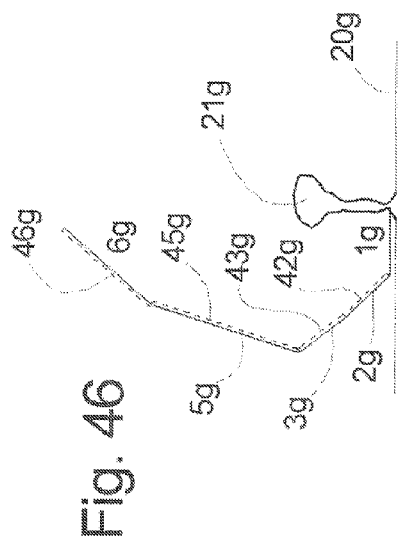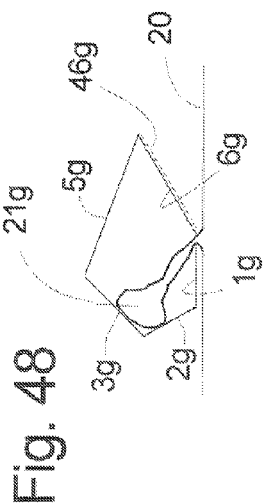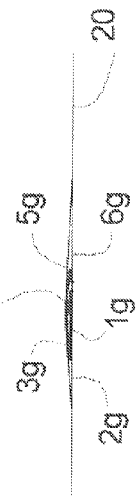

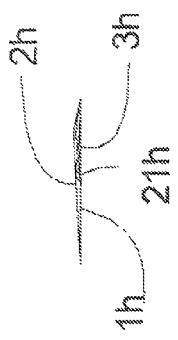
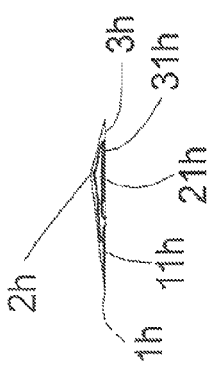
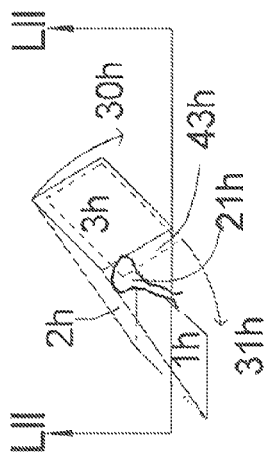
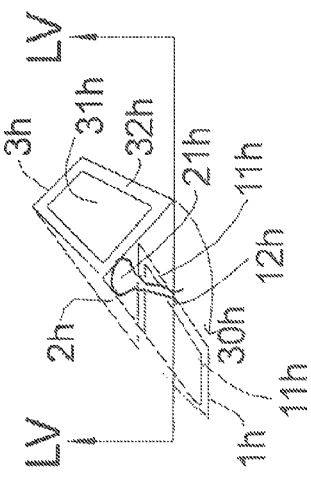
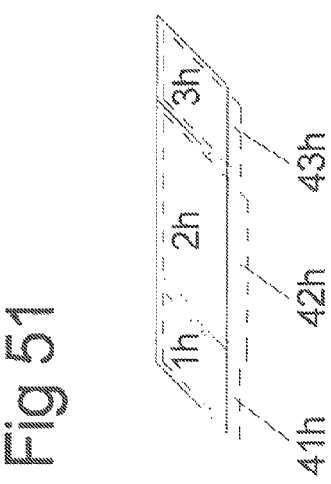
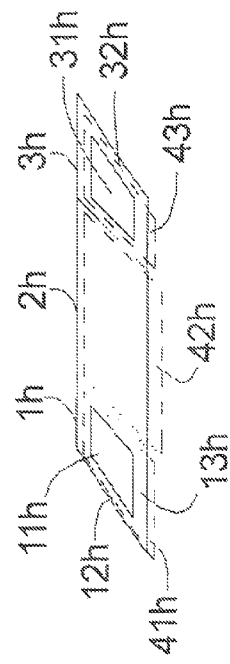

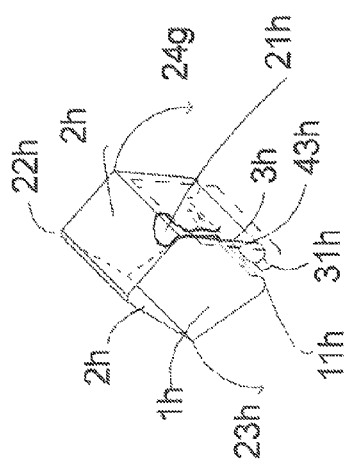
Fig 57
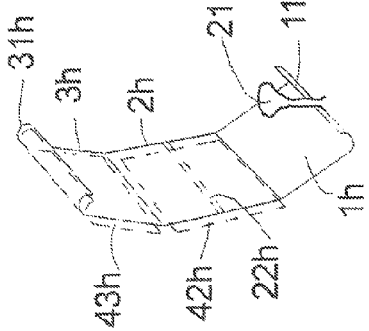
Fig 58 A
Fig 58 B
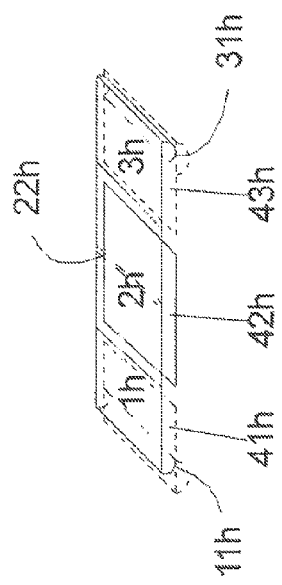
Fig 59
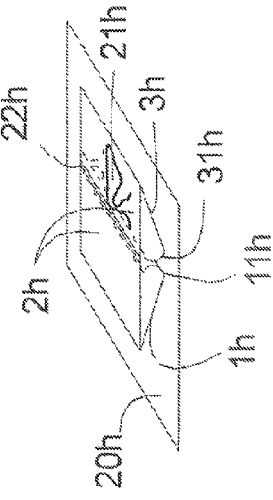
Fig 60
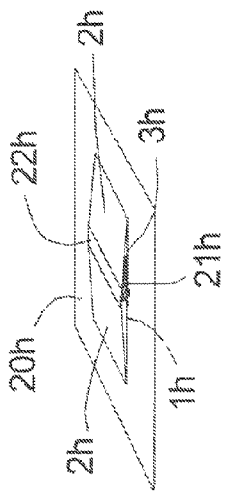

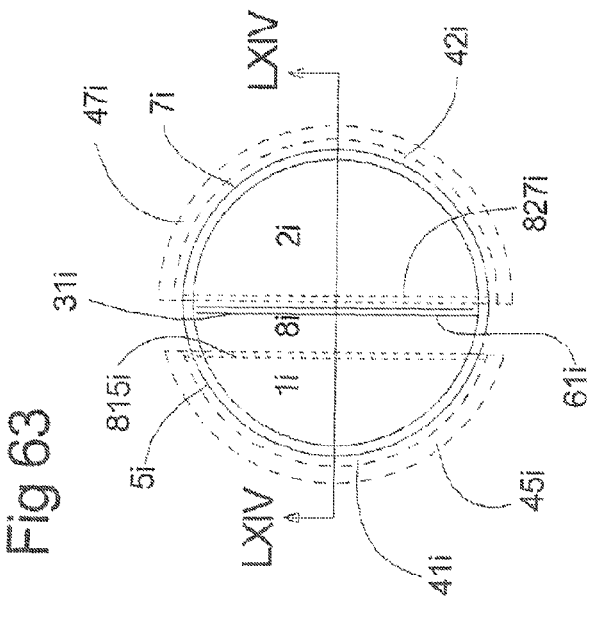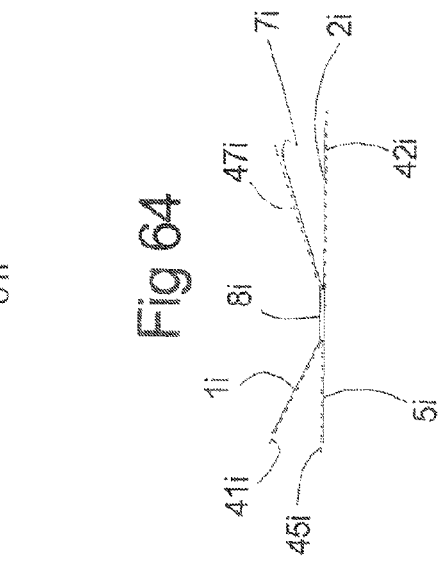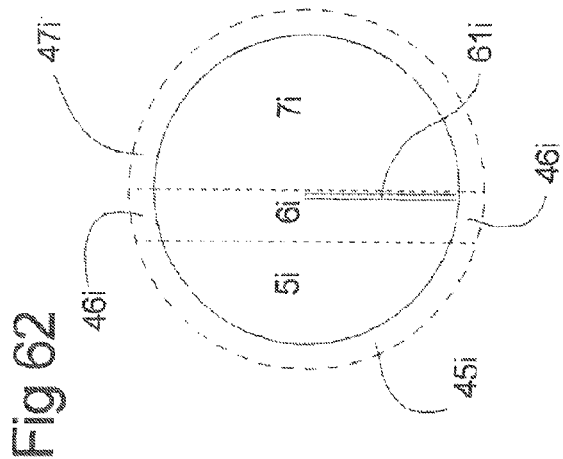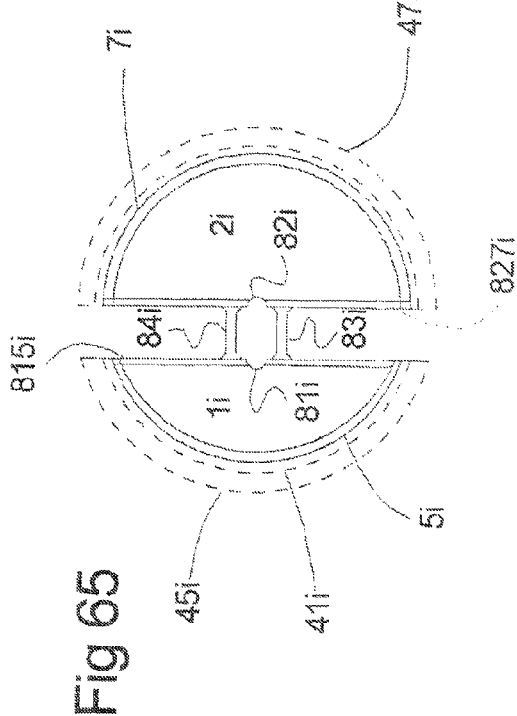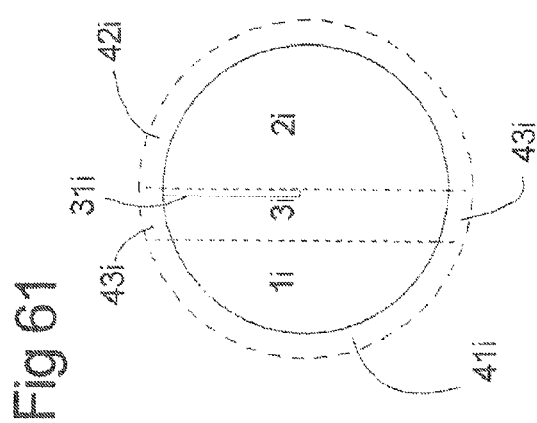

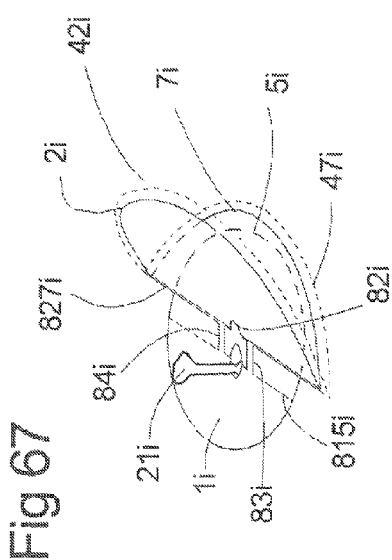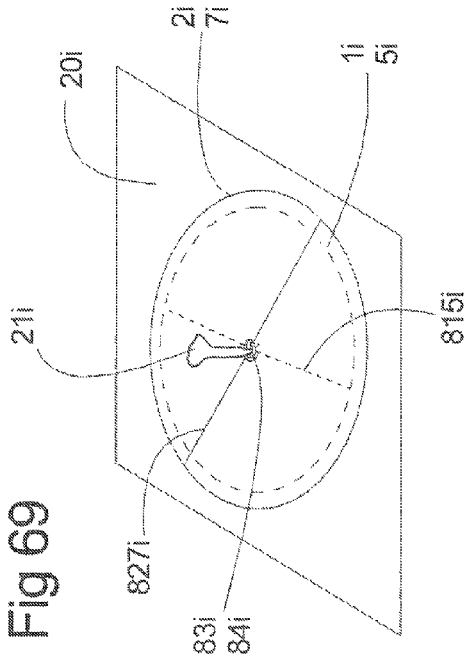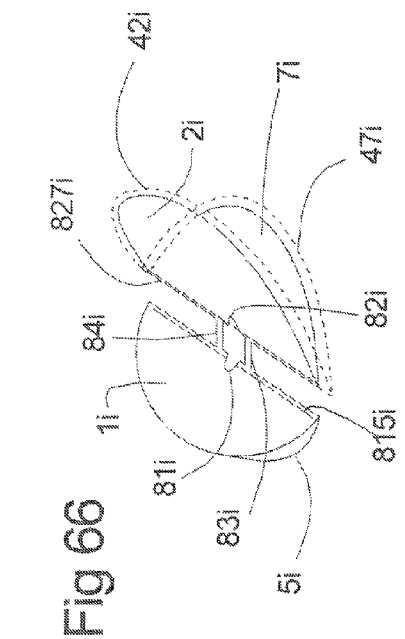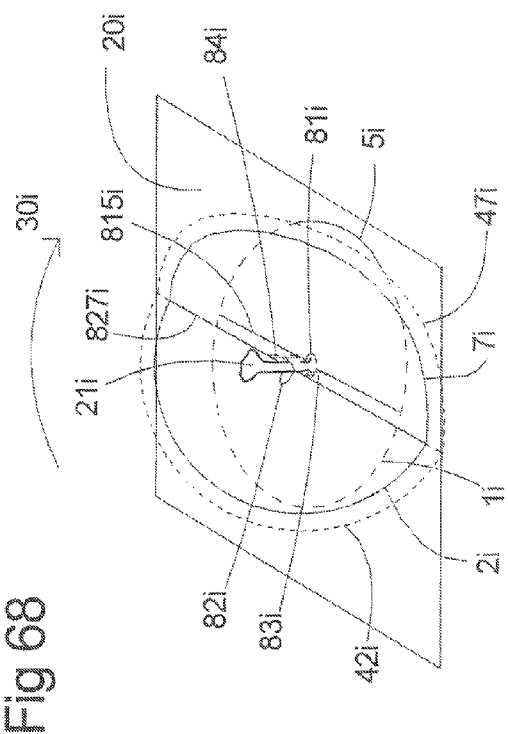

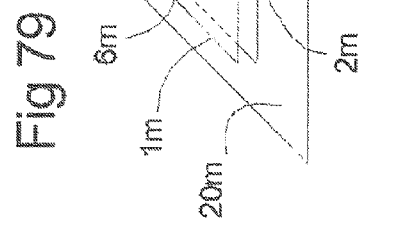
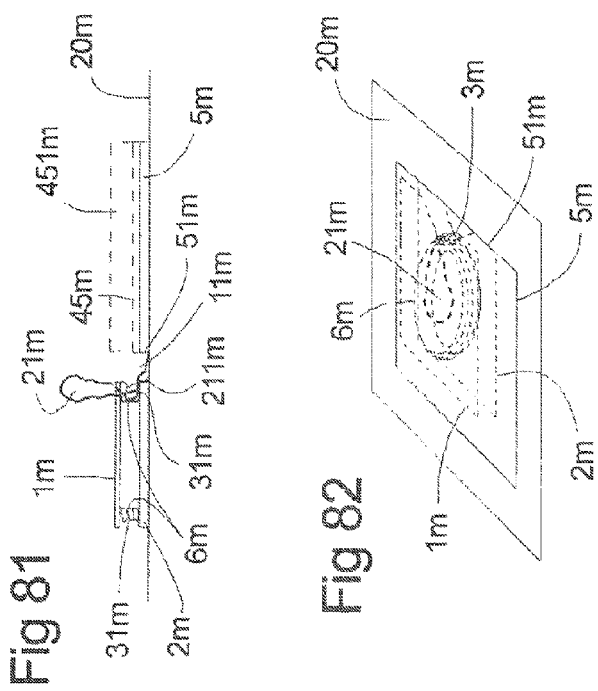
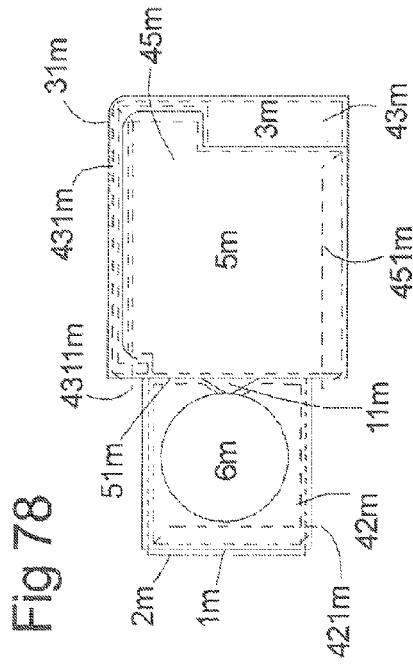
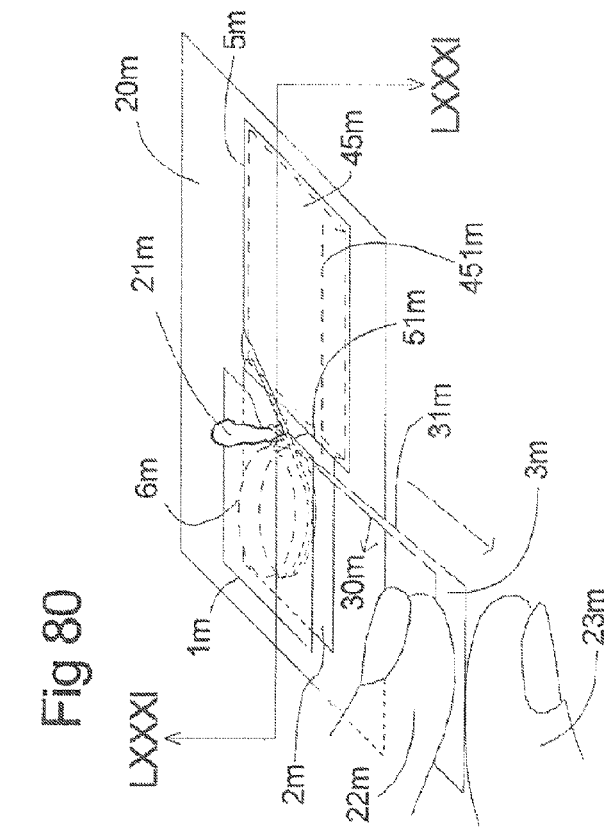

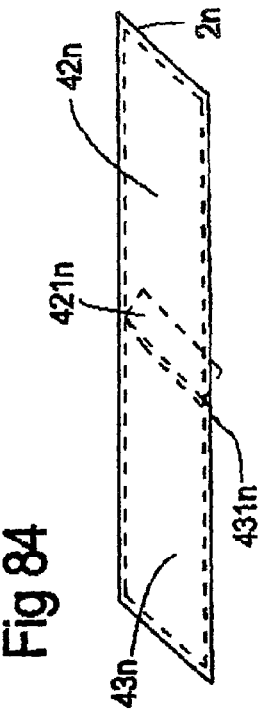
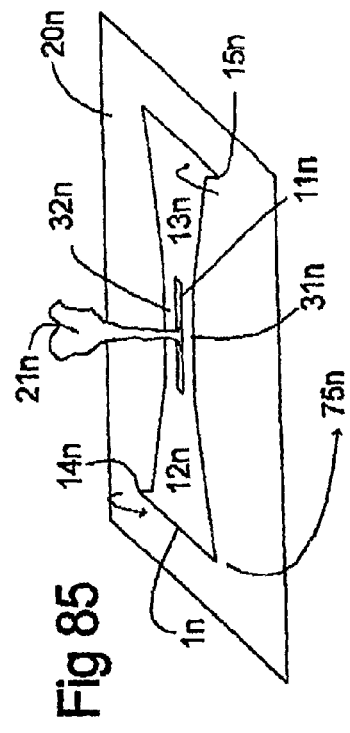
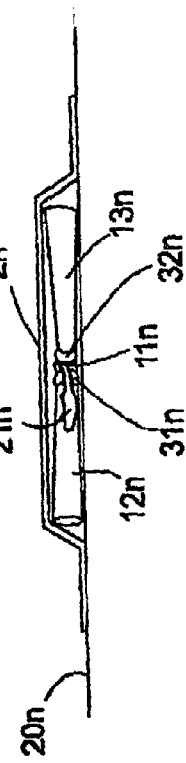
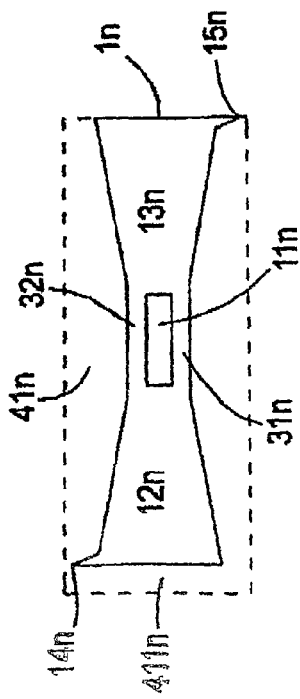
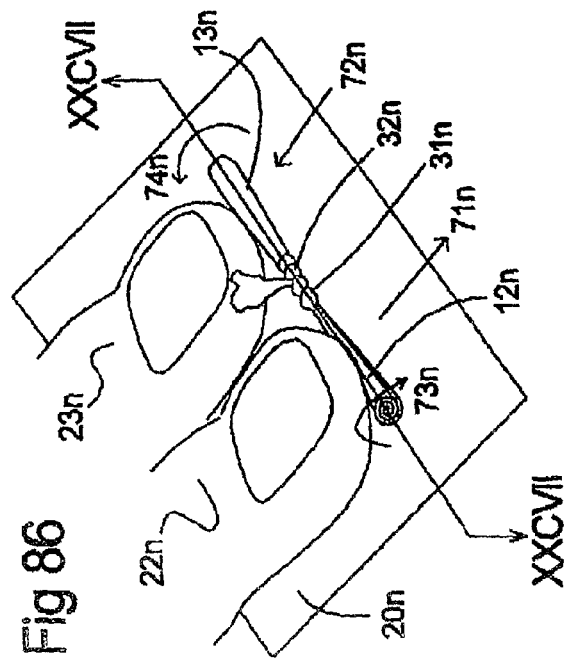

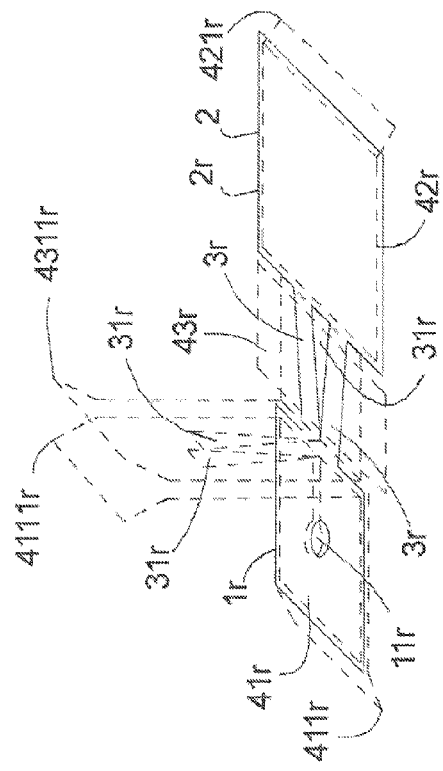
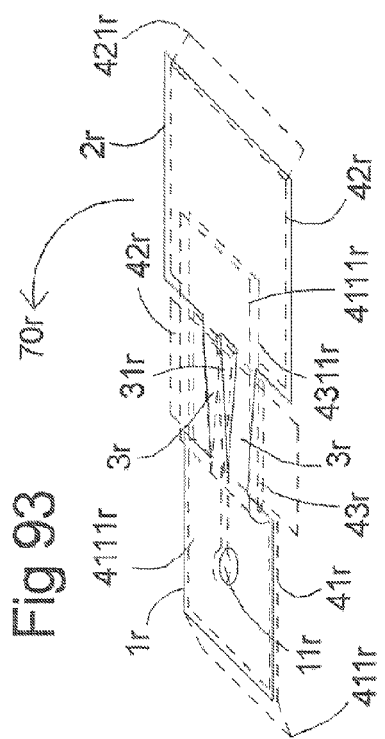
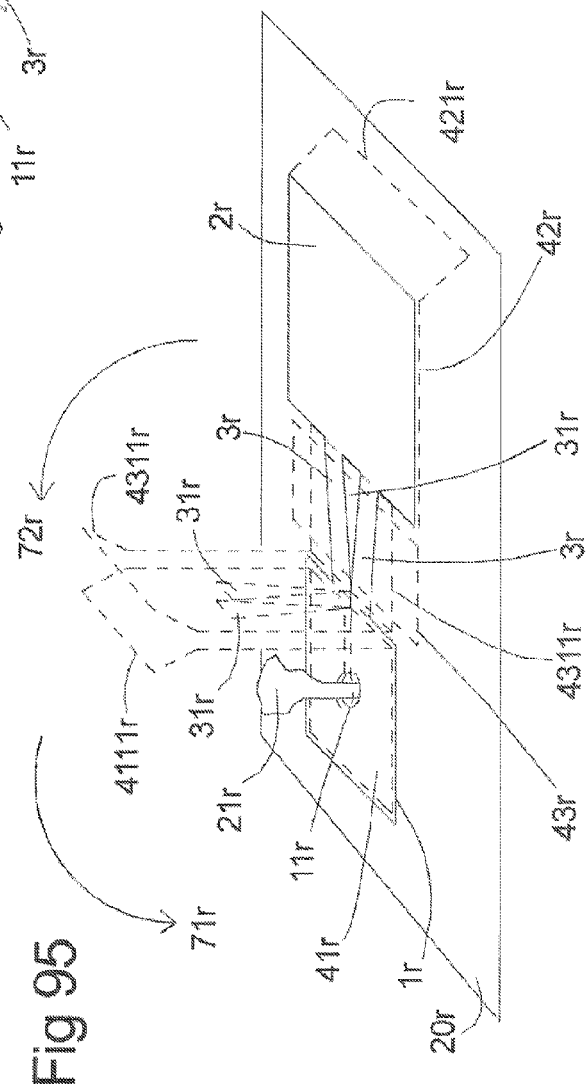

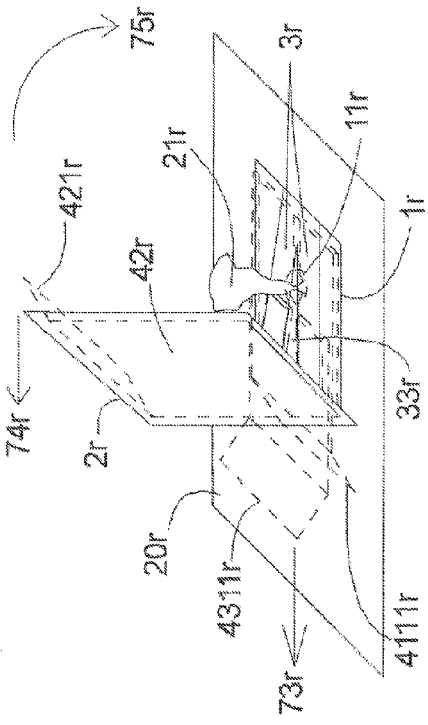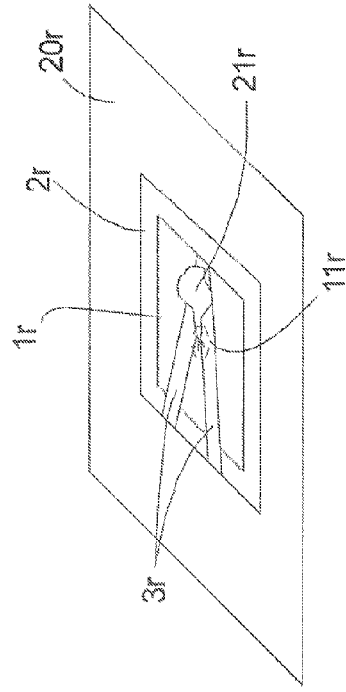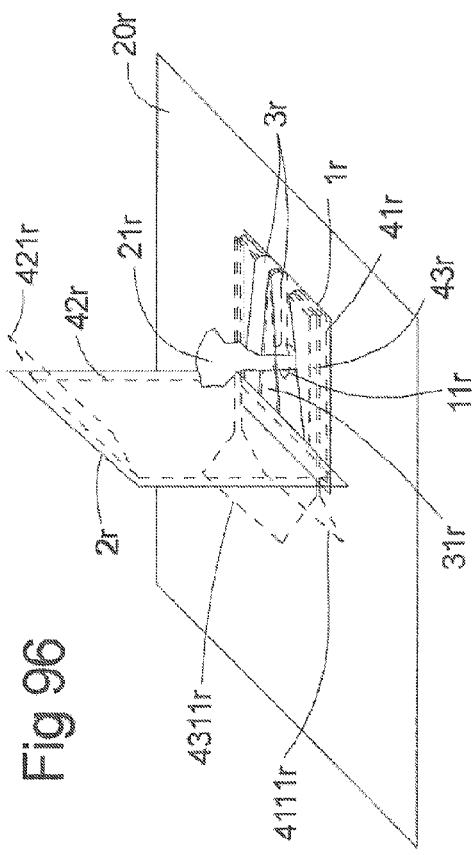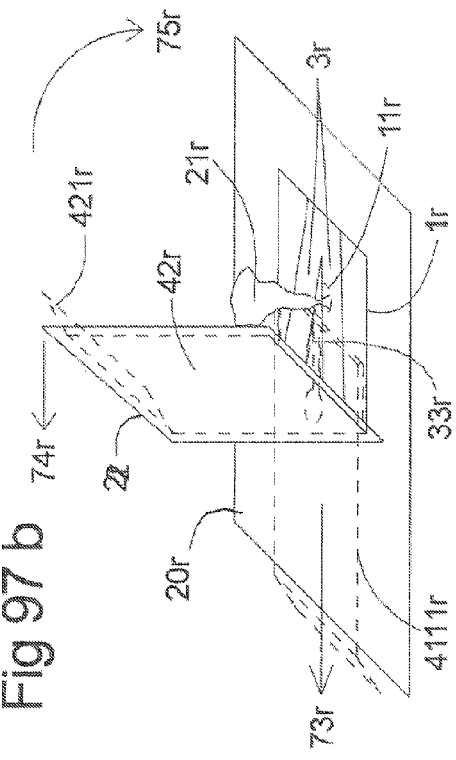

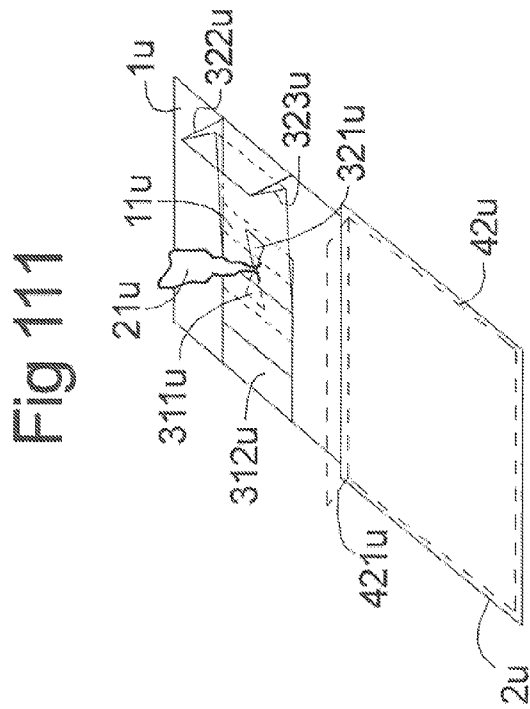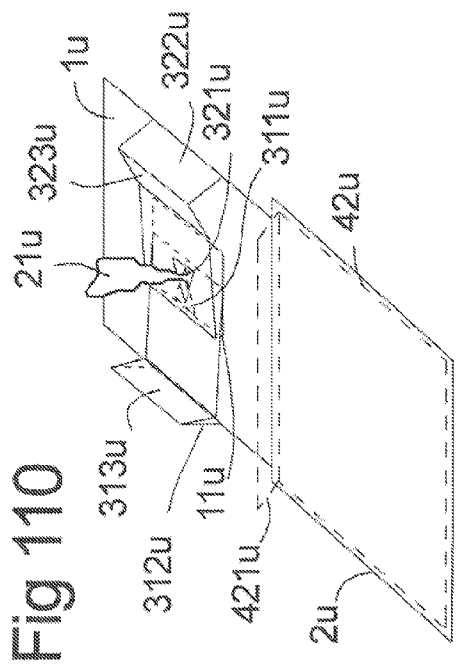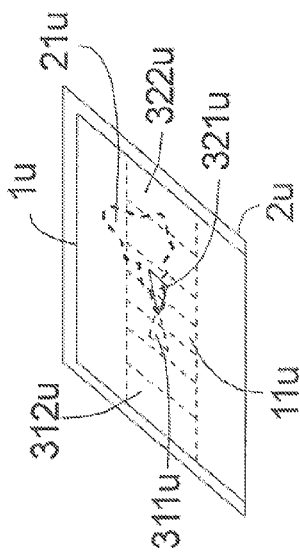

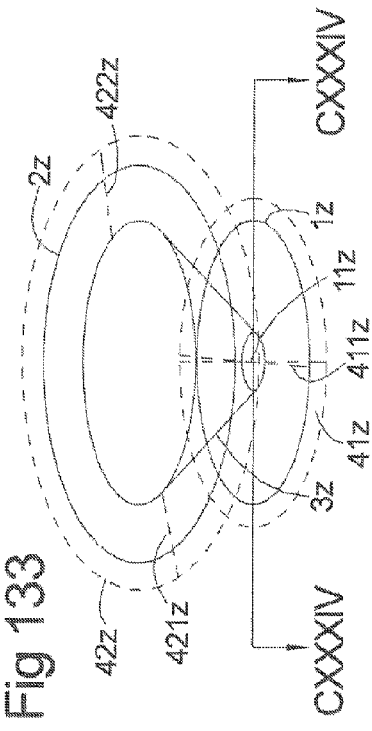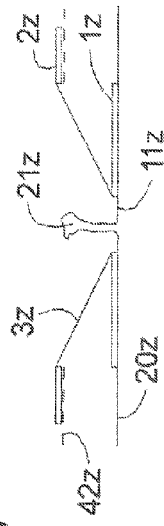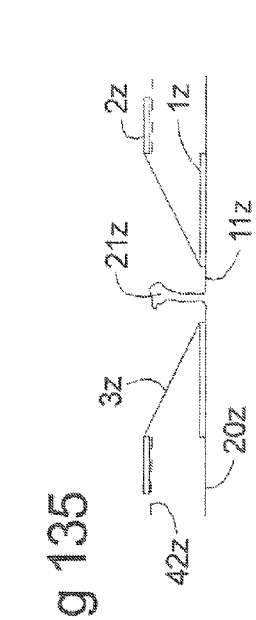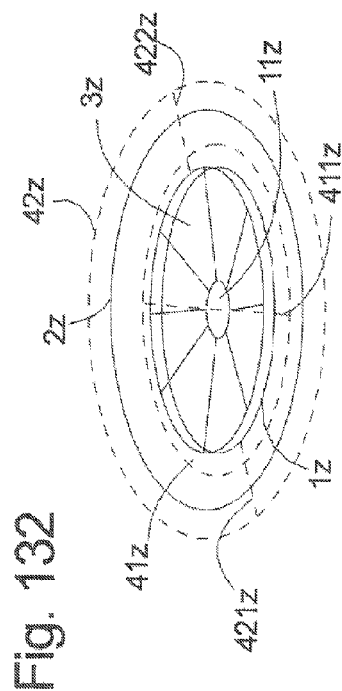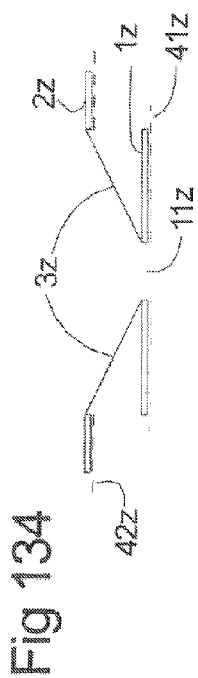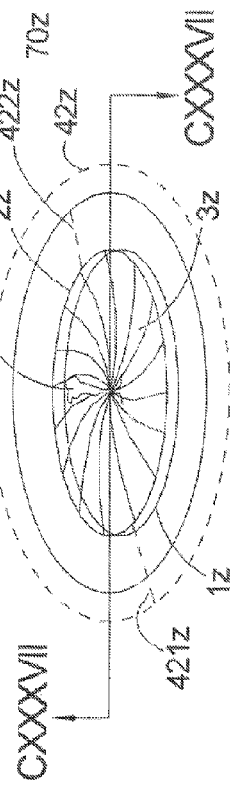

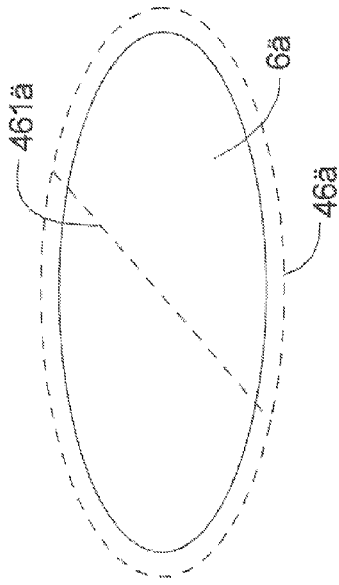
Fig 143
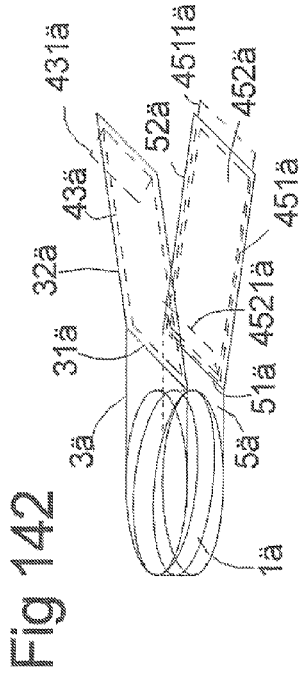
Fig 142
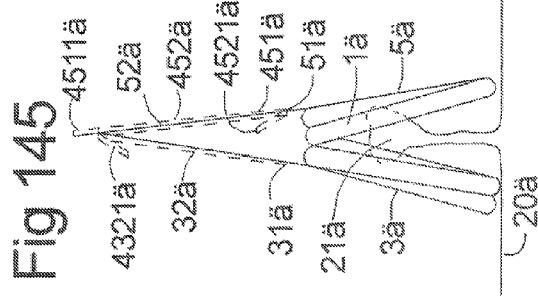
Fig 146
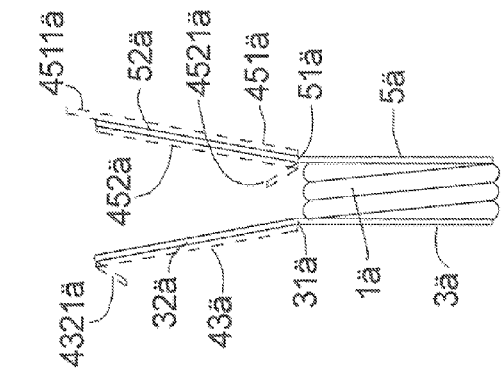
Fig 145
Fig 144

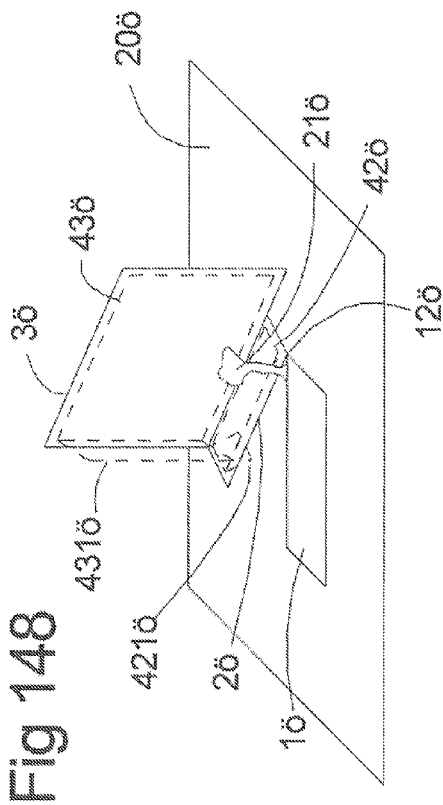
Fig. 147
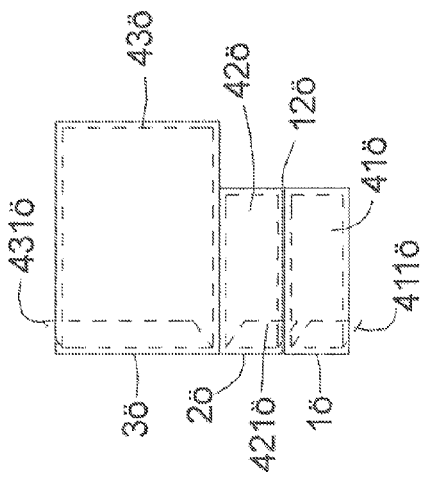
Fig. 148
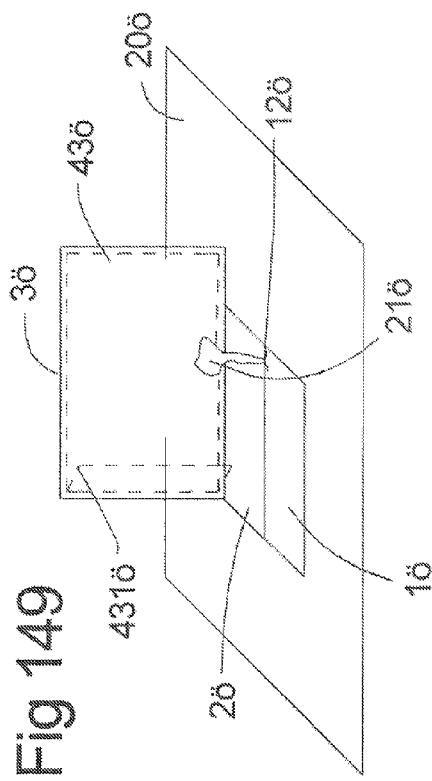
Fig 149
Fig 150

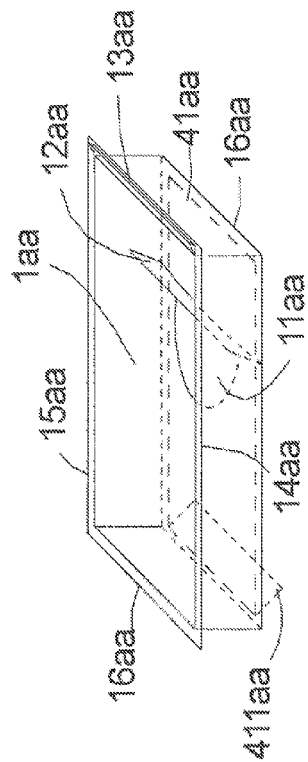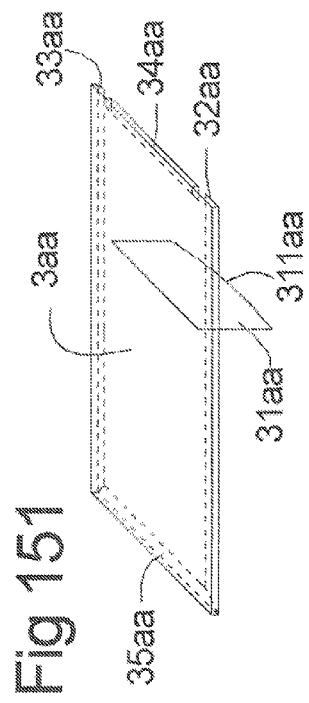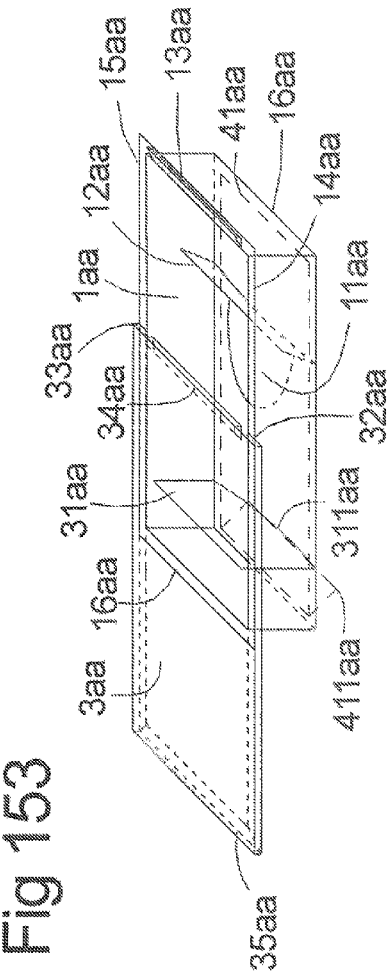

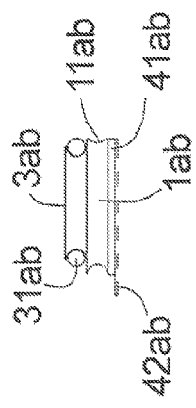
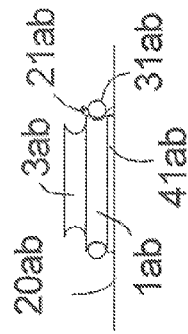
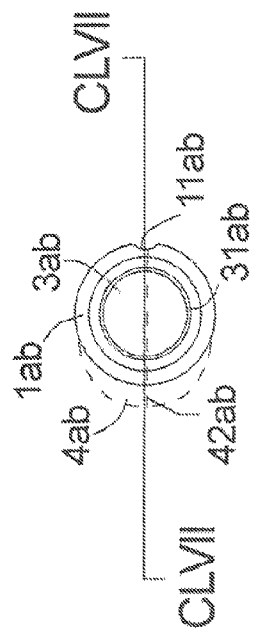
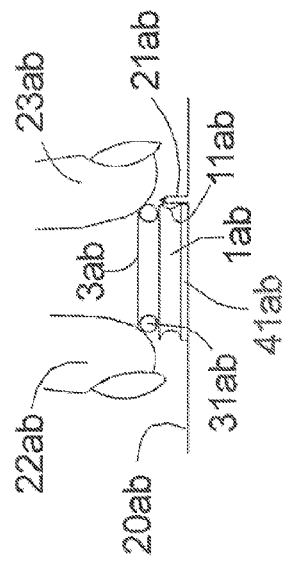

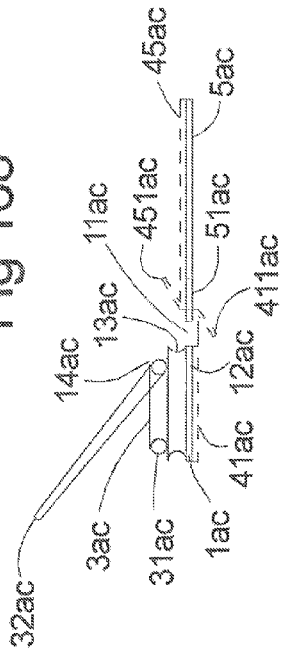
Fig 167
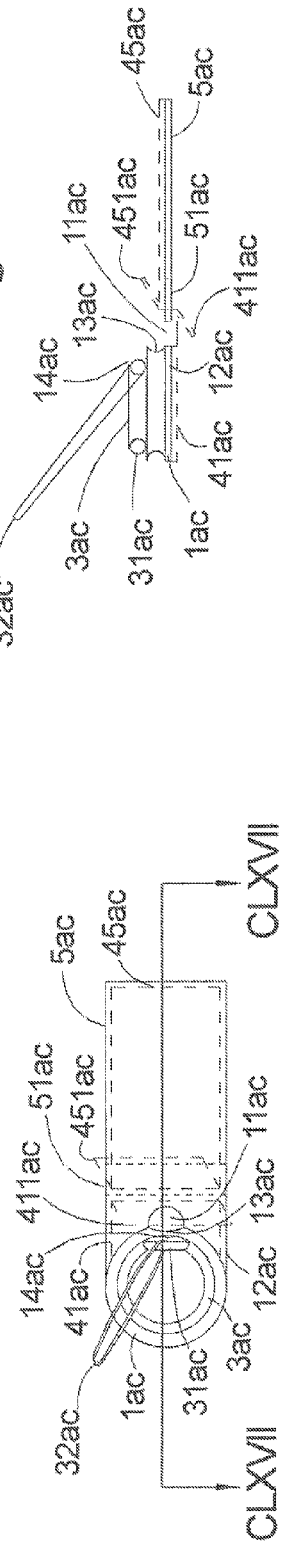
Fig 168
Fig 169
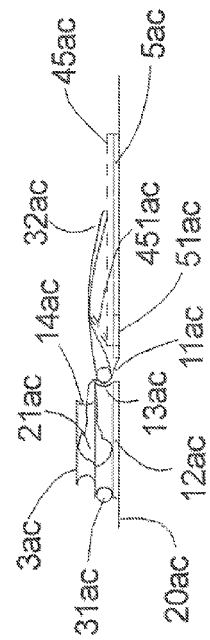
Fig 170
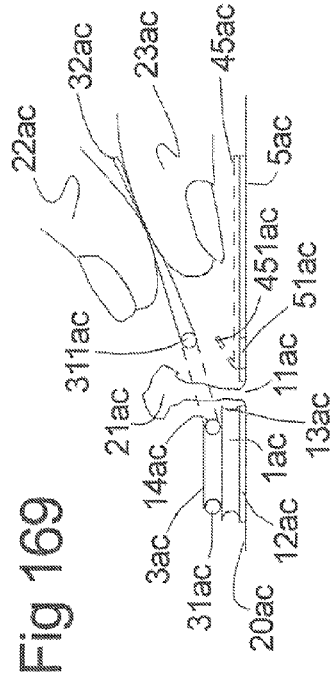
Fig 171
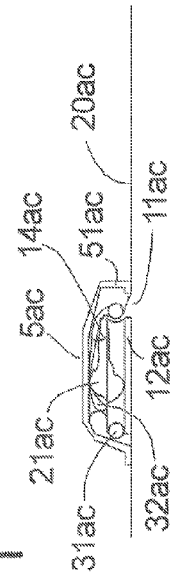

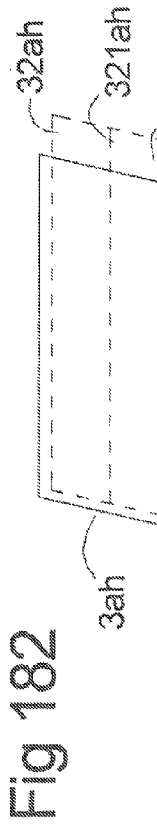
Fig 182
Fig 183
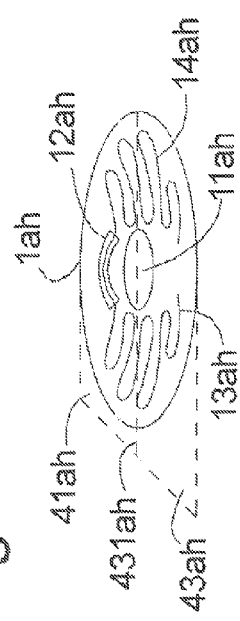
Fig 185
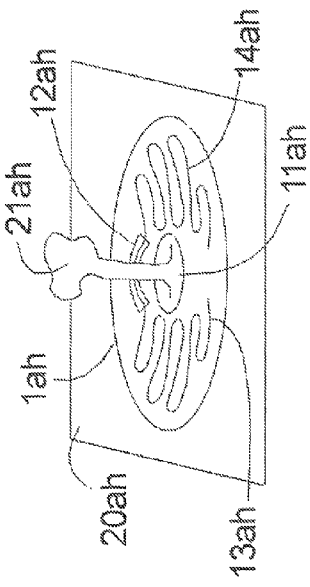
Fig 184
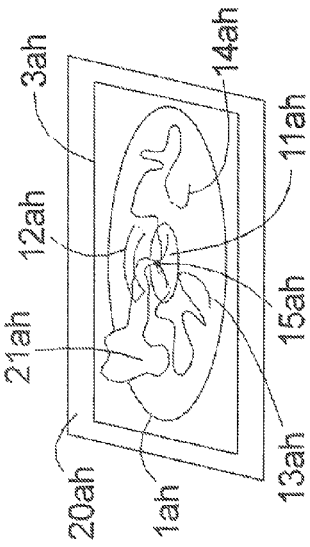
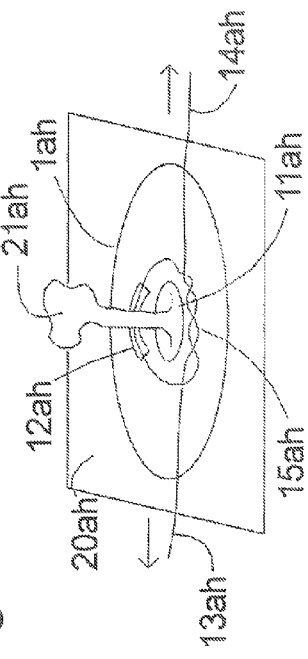
Fig 186

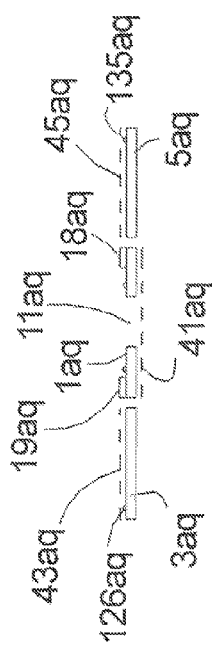
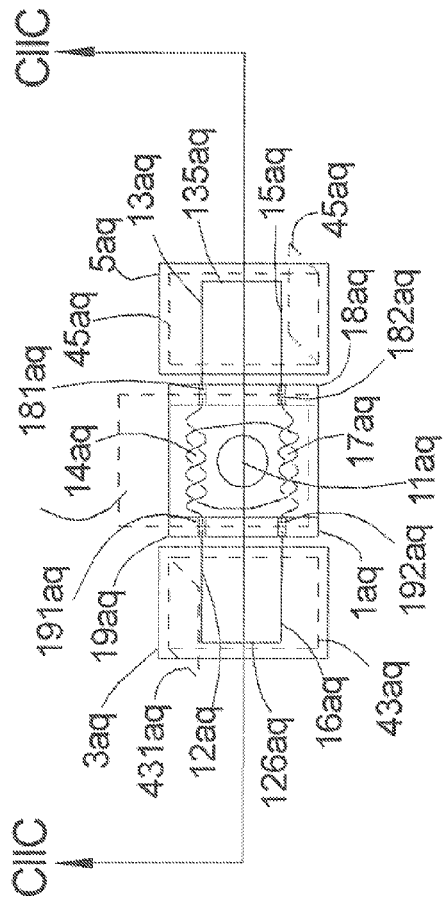
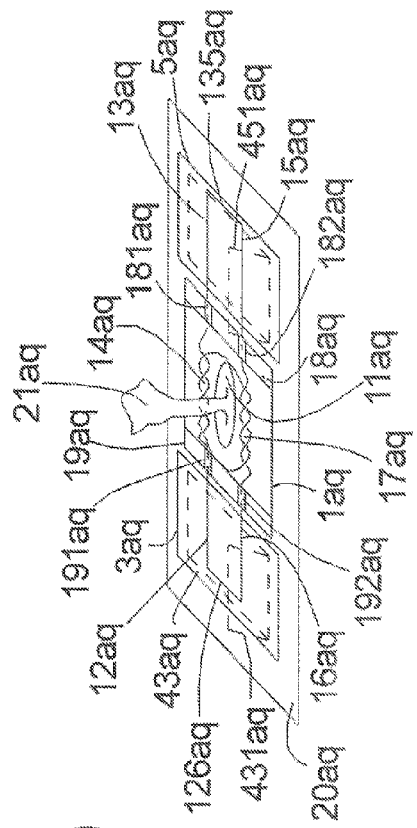

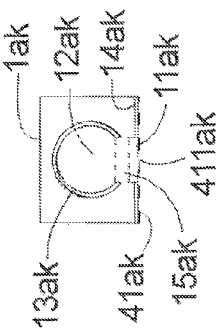
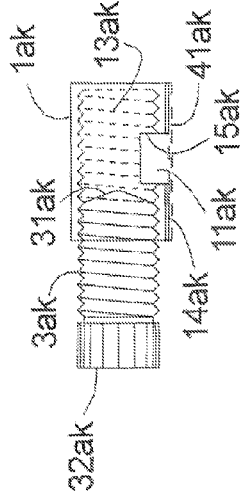
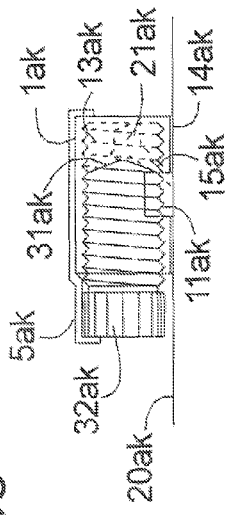
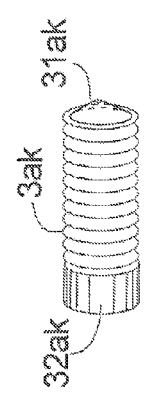
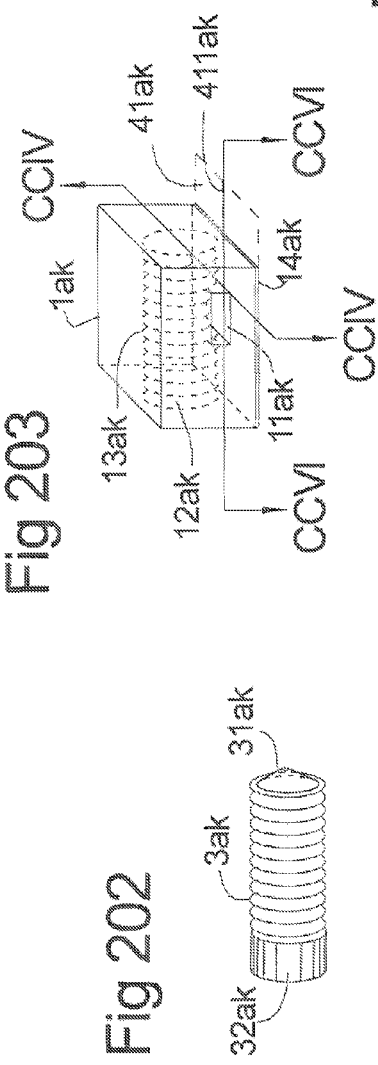
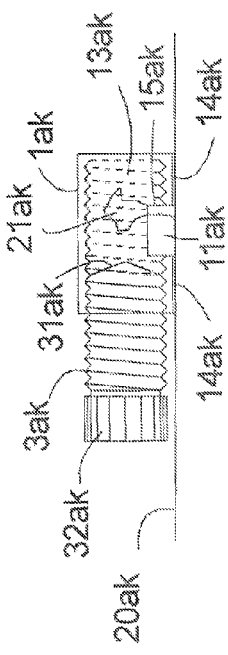

DEVICE FOR REMOVING ACROCHORDONS

CROSS-REFERENCE TO RELATED APPLICATIONS

This application is a continuation of International application PCT/IB2005/054334 filed Dec. 20, 2005, the entire content of which is expressly incorporated herein by reference thereto.

BACKGROUND OF THE INVENTION

Acrochordons or skin tags are common, easily diagnosed, skin colored or hyper pigmented, benign multiple skin tumors. They are often small and stalked and appear mostly on the neck, axillae, groin and upper torso of middle aged and elderly people. Acrochordons are very benign, asymptomatic forms of tumors which can be irritating following abrasion by clothes or which because of where it is situated can be cosmetically compromising.

In such cases skin tags can be removed professionally using local anesthetic and subsequent freezing with liquid nitrogen, burning by means of electro-desiccation or excision using a scalpel or scissors.

These methods give rise to a sore with risk for infections, scars and pain and in addition, necessitate some kind of bandage.

SUMMARY OF THE INVENTION

The invention enables self-treatment of benign, easily diagnosed skin tumors which appear as small filamentary or pedunculated growths on the skin surface, and which are termed acrochordons or skin tags.

To that aspect the invention relates to a method for occlusive removal of a protruding skin tag from a skin area. The method comprises the steps of encircling or enfolding the area of the protruding skin tag's nearest the skin, applying an occlusion pressure to the enclosed or enfolded skin tag, whereby sustained blood supply is occluded and necrosis of the skin tag is initiated, immobilising the skin tag relative to the skin area for a period sufficient to allow release of the skin tag from the skin area, and removing the skin tag.

The invention discloses a plurality of devices that can be used in the method according to the present invention. One device according to the invention comprises an adhesive member which fixes the device to the skin and which has an aperture, an edge or a surface or other support portion which encloses or contact the skin tag's base on the skin surface. The device also has a clamp which is connected to the adhesive member in different ways and which, because of its shape, can nip the skin tag's base on the skin surface and occlude the blood flow. Additionally, the device has a locking member which seals the skin tag to the skin to conceal it.

An adhesive band-shaped device consisting of different types of adhesive materials has protective films which can be removed and expose the different parts of the device. By using different types of adhesive materials, it is possible to seal the skin tag to the surface of an adhesive band-shaped device with protective films which can be removed and expose, and which are then turned at an angle of 90 degrees. The sealed skin tag can also be rotated before it is fastened to the skin surface. The rotation or twisting of the skin tag or a combination of both these procedures results in an occlusion of the skin tag's blood flow.

In another embodiment of the invention a small, adhesive, short, thread-like device is wrapped around the base of the skin tag between two adhesive units with a low tension to stop the blood flow.

In this case, the adhesive thread is fixated to the skin tag's surface and the different ends lock to each other, which increases the occlusion effect and prevents the thread from slipping when the applied tension disappears. Lacking blood flow, the living tissue in the skin tag quickly recedes and falls off spontaneously in the occlusion area. Such an occlusion of living tissue is well-known within surgery and is used within all medical specialties.

According to the invention, the skin tag is securely fixed by the support portion and the pressure member of the device which in turn through the adhesion and locking members sit tightly glued to the skin surface, which means that when the device is removed from the skin after a while, the tied-off skin tag is automatically removed too.

The advantages of the invention are that individuals themselves can, in a simple and inexpensive manner, remove skin tags from their skin without pain or blood effusion and without risk for infection as no wound is formed. Additionally, the removal of the skin tag occurs without scarring which means that the individual does not feel cosmetically compromised during the few days of treatment.

When the skin tag is removed, it seldom reappears in the same place again, although it is not unusual for a new skin tag to appear in close proximity or in the same area as a previously removed skin tag.

The device according to the invention comprises small thin strips, bands or discs s of material with one or several adhesive surfaces consisting of more or less flexible or elastic hydrocolloids, hydrogels, foams, nonwoven or polymer fabrics. The adhesive surfaces on the strips, bands or discs etc. have protective films or covering strips which partly inactivate the bonding agent and partly divide the adhesive surfaces into smaller adhesive surfaces. These surfaces constitute the adhesion member, pressure member and locking member of the device and can be activated at different times depending upon the order in which the protective films or covering strips are removed when the device is applied to the skin tag. Some of the pressure members of the device have surfaces that are straight, curved or circular, which in different ways can be maneuvered around the base of the skin tag so that single, double, multi-sided or circular casing occurs, resulting in the occlusion of the proximal blood flow.

In another embodiment of the invention, the device comprises two small adhesive, more or less elastic sheets which are kept together by a short thin thread or bridge-like construction. One of the sheets or the adhesion member is glued to the skin first, after which the skin tag is grasped between the thumb and forefinger and stretched lightly straight upwards. The thread or pressure member may then be bound between the sheets round the base of the skin tag so that an occlusive ligation of the skin tag occurs. This does not require much strength because the cross-section area of the skin tag is small and all parts of the bridge-like construction are continually sealed to the skin tag's surface and previously applied bridges. Finally the other sheet or locking member is fixed to the skin, or according to the preferred embodiment, on top of the skin tag so that it is concealed during the release period.

In a further embodiment, the band-shaped device has slits which extend halfway across the band from both ends, which makes it possible to rotate and bend the band in different ways round the skin tag sealed within the device. To facilitate manipulation of a skin tag, some of the protective films or covering strips are on the adhesive side of the slits, rendering the band more rigid and facilitating rotation and/or folding of the skin tag.

In a third embodiment, there is a short, thin band consisting of the materials described above, where one side of the band has reinforced adhesive qualities. First of all the bonding agent in the central part of the band is activated and the skin tag is stuck between the thumb and forefinger in the direction of the band's cross section. The skin tag is then rotated 180-360 degrees, whereby the bonding agent on one of the outer end of the band is stuck to the skin. Then the other outer end of the band is activated and stuck to the skin so that the rotated and thereby occluded skin tag is fixed in a fold where the skin tag lies parallel to the skin surface.

In a fourth embodiment, the adhesive area is located diagonally on both sides of the band-shaped device. The skin tag is fixed in a fold right over one of the adhesive surfaces, and is then stuck to the skin. The other adhesive surface is then stuck over the first one for increased stability and invisibility.

In a fifth embodiment, an entire side of the band-shaped device is adhesive. Additionally, there is a small area transversal to the band's other side, which is also adhesive. In this embodiment, the skin tag is fixed longitudinally in a fold formed in the central adhesive section of the band. The central section including the skin tag can then be bent down and stuck on top of some of the ends after activation of the outer, small, adhesive surface. Thereby, an occlusive fold is created that reduces blood circulation to the skin tag. The occlusive effect can be increased if the entire device with the skin tag sealed in the fold is rotated before the fold is bent down and stuck to an end.

In a sixth embodiment of the invention, the base of the skin tag is squeezed between specially formed, more or less hard edges with incisions, bead, flaps, or through different types of eccentric clamping mechanisms where the base of the skin tag is squeezed off and occluded simultaneously with the adhesion and locking of the different surfaces to each other such that the skin tag is fixated in a position parallel to the skin's surface.

In a seventh embodiment according to the invention, the skin tag is in the middle of the device according to the invention, after which the different parts of the device are turned towards each other such that the existing more or less elastic, adhesive, flexible bands, sheets or rings between the parts are wrapped, drawn, crimped or rotated around the skin tag's base resulting in a satisfactory occlusion.

In an eighth embodiment of the invention, an occlusion is achieved at the skin tag's base by a shearing effect, whereby it is wedged tightly in a V-shaped, more or less flexible section.

A similar effect can be achieved in a ninth embodiment of the invention where the skin tag is slid through an aperture in three different sections lying on each other of the device according to the invention. By displacing the three layers in different directions in relation to each other, the edges of the aperture applies pressure on the base of the skin tag and result in an occlusion of the blood flow.

In a tenth embodiment of the invention the skin tag is placed in an elongated aperture in an elastic, adhesive band which is then rolled in a circle around the skin tag, whereby the long sides of the aperture are twisted around the base of the skin tag, resulting in an occlusion.

In an eleventh embodiment of the invention the skin tag is squeezed at the base in a transversally cut slit in the convex wall of a bent, more or less elastic and flexible tube, after which the skin tag is stuck in the pipe and affixed.

In a twelfth embodiment of the invention, the base of the skin tag is squeezed between two twists of a more or less elastic and flexible, spiral-shaped device with a thin, adhesive, band-shaped section which is then bent down and stuck to the skin surface which simultaneously fixes the skin tag.

In a thirteenth embodiment of the invention, there are sheets or wings at the top or bottom of the small vessels which are stuck to the skin above the skin tag. By moving the top and bottom ends in relation to each other, the wings are clamped to the base of the skin tag. When an adequate influence on the blood flow is obtained, the wings are locked in an occlusive manner.

In a fourteenth embodiment of the invention, O-rings or other more or less elastic or flexible rings, threads or straps are used which by pressing the skin tag's base against an appropriately formed counter aperture stick to the skin and can give rise to an occluded compression of the blood flow.

In a fifteenth embodiment of the invention, a device with threads is used with one or several knots or loops which in different ways can be tied or wrapped around the lower part of the skin tag which, when occluded, can be concealed and stabilized in some form of a more or less adhesive covering section.

In a sixteenth embodiment of the invention, the occlusion of the skin tag can be achieved by an adhesive and very elastic film with an extremely small aperture which is pulled over the skin tag and which, when retracted, occludes the blood flow to the base.

In a seventeenth embodiment of the invention, an occlusion can be achieved by attaching sticky devices to the skin where a spiral contracts so that the skin tag is fixated simultaneously to the compression of this base or where a clasp or a pair of connected triangles pinch the skin tag's base on both sides.

BRIEF DESCRIPTION OF THE DRAWING FIGS.

The invention shall be illustrated in detail in the following on the basis of the accompanying drawings, in which:

FIG. 1 is an overview of a device according to the invention in the form of a thin band, where the adhesive surface is situated against the paper.

FIG. 2 is a longitudinal section of FIG. 1 taken along II-II.

FIG. 3 is an overview of another embodiment of the invention where the device has an asymmetric form.

FIG. 4 is a longitudinal section of the device taken along IV-IV in FIG. 3.

FIG. 14 is an overview of a third embodiment of the invention where the band-shaped device has two diametrically opposed adhesive surfaces on each side of the device.

FIG. 15 is a longitudinal section taken at XV-XV in FIG. 14 and shows the adhesive surfaces with protective films and associated flaps.

FIG. 16 illustrates how a skin tag is placed in the middle of one side of the activated adhesive surface.

FIG. 17 illustrates how the skin tag in FIG. 16 is first sealed and then rotated.

FIG. 18 illustrates how the sealed skin tag in FIG. 17 is stuck horizontally to the skin surface.

FIG. 19 illustrates how the other surface of the band in FIG. 16 is activated and stuck on top of the skin stuck as taken in FIG. 18.

FIG. 20 is a longitudinal section taken along the axis XX-XX in FIG. 19, which shows how safe and secure the fixated skin tag lies in a correctly applied device.

FIG. 28 is a longitudinal section along the line XXVIII-XXX in FIG. 27, which shows how another part of the band-shaped device is prepared for fixing to the skin.

FIG. 29 is a longitudinal section of FIG. 28, which illustrates how by rotating the prepared section in FIG. 28 around itself, it is possible to stick it to the device shown in FIG. 27, which is already attached to the skin.

FIG. 30 is a longitudinal section of FIG. 29, which illustrates how the already applied device occludes and fixes the skin tag on the skin.

FIG. 31 illustrates a longitudinal section of the fifth embodiment of the device, which is an alternative embodiment to the one in FIGS. 8 and 9.

FIG. 32 is a longitudinal section which shows how the device in FIG. 31 is fixed to the skin in the area of the skin tag.

FIG. 33 is a longitudinal section of the device in FIG. 32 which shows how the skin tag is fixed to the surface of the device.

FIG. 34 is a longitudinal section of the device in FIG. 33 which illustrates how a transversal fold is formed around the skin tag.

FIG. 35 is a longitudinal section of the device which shows how the skin tag is sealed in the fold described in FIG. 34.

FIG. 36 illustrates a longitudinal section of a device applied to the skin, where the fold with the sealed skin tag shown in FIG. 35 is bent sharply and fixed parallel to the skin surface so that the blood flow is occluded. When the device is removed from the skin after the degeneration period, the skin tag will follow without causing pain or bleeding.

FIG. 40 is an overview of another embodiment of the invention consisting of a more or less rigid, band-shaped device where one side is adhesive. The device has five sections and four pre-prepared folds where two of the folds have centrally placed, opposite cut-outs.

FIG. 41 is an overview where one section in FIG. 40 is stuck on the skin with cut-outs placed against the base of the skin tag.

FIG. 42 shows how the three middle sections in FIG. 40 are twisted around the skin tag.

FIG. 43 is an overview which shows how the twists in FIG. 42 are completed such that the opposite cut-outs shown in FIG. 40 lie against the other side of the skin tag.

FIG. 44 is a cross section of FIG. 43 which shows how the skin tag, which is occluded on both sides of the opposite cut-outs, is completely concealed and fixed in one of the three central sections of the created fold and is simultaneously fixed to the skin surface.

FIG. 45 is an overview of another embodiment of the invention consisting of a band-shaped device which is adhesive on one side and has 5 sections of differing sizes.

FIG. 46 is a longitudinal section along the line XLVI-XLVI in FIG. 45, which illustrates how an end of the band-shaped device on one of the sections is stuck to the skin as near the skin tag as possible.

FIG. 47 is a longitudinal section along the line XLVI-XLVI in FIG. 45, which demonstrates how the different sections of the band-shaped device in FIG. 45 are folded over the skin tag.

FIG. 48 is a longitudinal section along the line XLVI-XLVI in FIG. 45, where another section of the other end of the device is placed as near the skin tag as possible.

FIG. 49 is a longitudinal section along the line XLVI-XLVI in FIG. 45, which shows how two of the five sections of the device are stuck to the skin, following which the occlusion of the skin tag's base begins.

FIG. 50 is a longitudinal section along the line XLVI-XLVI in FIG. 45, where three of the sections of the device are stuck to the skin, thus occluding, encircling and fixing the skin tag to the skin.

FIG. 51 is an overview which shows another embodiment of the invention consisting of a more or less rigid, band-shaped device with three sections each having an adhesive side.

FIG. 52 is an overview of the band-shaped device in FIG. 51 where one of the exterior sections is applied to the skin as near the base of the skin tag as possible.

FIG. 53 is a longitudinal section along the line Lll-Lll in FIG. 52, where the second of the exterior sections of the band-shaped device is applied as near as possible to the base of the skin tag, and where the adhesive side of the middle section is pressed down and fixes the skin tag on top of the sections on the skin and simultaneously occluding the base.

FIG. 54 illustrates a variant of the invention as per FIG. 51, where the outermost ends of the two exterior sections have a hard central part and a soft periphery and where the outer free edge of the exterior sections of the device are cut at an angle and where each of the sections have an adhesive side.

FIG. 55 is an overview which shows how one of the angled edges of the exterior sections is stuck to the skin near the base of the skin tag and how the two other sections are folded over the skin tag.

FIG. 56 is a cross section along the line LV-LV in FIG. 55 which shows how the angled edge of the other section is stuck to the base of the skin tag, after which the adhesive side of the middle section is bent down and fixes the skin tag on top of the exterior sections and simultaneously occludes the base of the skin tag.

FIG. 57 is an overview of the device according to the invention, which shows a more or less rigid device with three sections each with its adhesive side, where the outer edge of the exterior sections is rolled a half turn and a transversal fold is made in the center of the middle section.

FIG. 58A is an overview of the device where the rolled edge of one of the exterior sections is placed against the base of the skin tag.

FIG. 58 B is an overview which shows how the middle and other exterior sections are folded over the skin tag and how the second one of the exterior sections' outer edge is placed against the base of the skin tag.

FIG. 59 is an overview where the upright fold of the middle section is pushed down to a level parallel to the skin.

FIG. 60 is an overview which demonstrates partly how the skin tag can be fixed on the upper side of the exterior sections and partly how the occlusion the base of the skin tag by the rolled up edges can be increased by continuing to put pressure on different parts of the upper side of the middle section.

FIG. 61 is an overview of a section of the device according to the invention which consists of a more or less flexible and elastic, thin disc with an adhesive underside covered by a protective film, which is divided into three parts by two parallel slits extending through the protective film, where one slit is part of a radius which is punched through the disc.

FIG. 62 is an overview of another disc identical to that described in FIG. 61, but with a more or less bigger radius.

FIG. 63 is an overview where the slit of the smaller disc is inserted in the bigger disc, after which the central strips of the protective film from both discs in FIGS. 61 and 62 are removed, and the exposed adhesive surfaces are centered and stuck to each other.

FIG. 64 is a cross section of the line LXIV-LXIV in FIG. 63 and describes how both discs form two new asymmetrical discs on either side of the common, stuck-together area.

FIG. 65 is an overview illustrating how material is removed from the common, stuck-together area such that the discs acquire their central cavities and retain two centrally placed, thin strips which keep the two asymmetrical discs together.

FIG. 66 is an overview showing how the protective film is removed from one of the asymmetrical discs so that the adhesive surface is exposed.

FIG. 67 is an overview illustrating how the smaller disc is stuck to the skin with a skin tag projecting through the centrally placed aperture.

FIG. 68 is an overview illustrating where the skin tag is slid through the thin strips between the disc and through the aperture in the bigger disc.

FIG. 69 is an overview illustrating how the existing strips between the discs occlude the base of the skin tag and how the bigger disc is stuck to the skin on top of the smaller disc.

Figure 70:
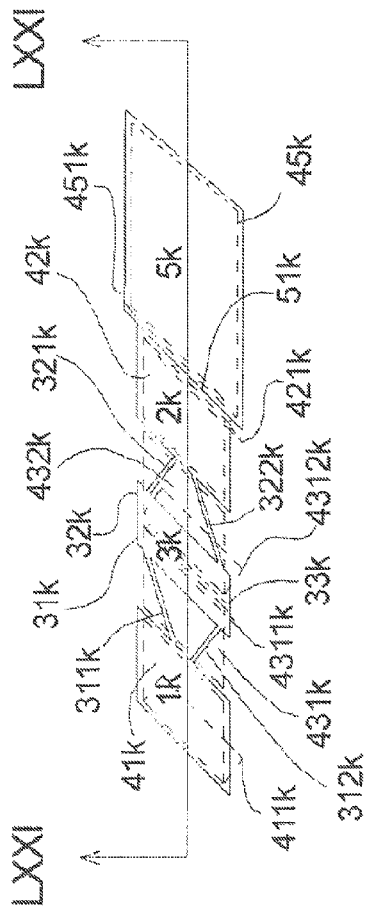

FIG. 70 is an overview of a thin, band-shaped device with 4 sections each having an adhesive surface where there are narrow strips between three of the sections.

Figure 71:
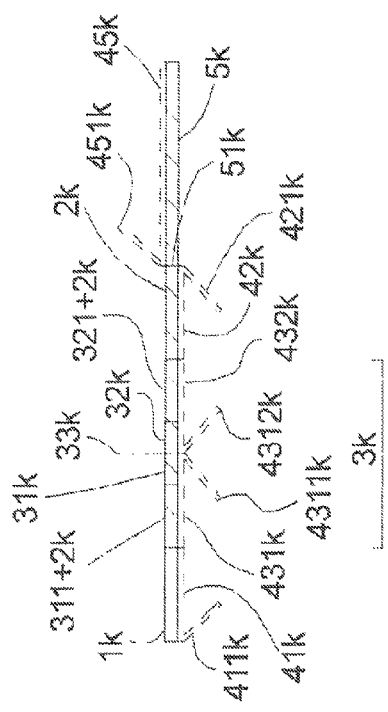

FIG. 71 is a cross section along the line LXXI-LXXI in FIG. 70 which illustrates the division between the adhesive surfaces and the protective films on the device.

Figure 72:
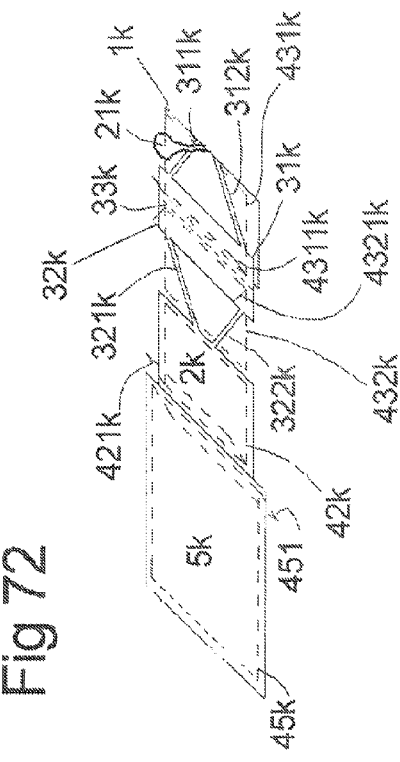

FIG. 72 is an overview illustrating how the section of the device in FIG. 70 is placed against the base of the skin tag.

Figure 73:
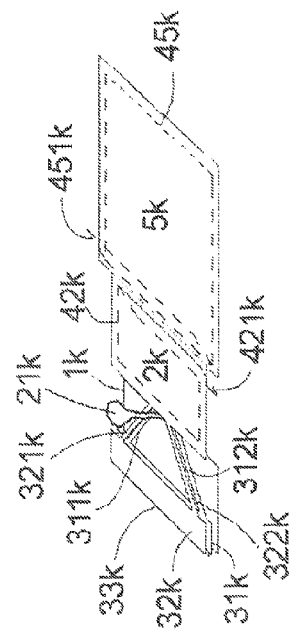

FIG. 73 is an overview illustrating how another section of the device is placed on the skin on the side of the skin tag opposite to that shown in FIG. 72.

Figure 74:
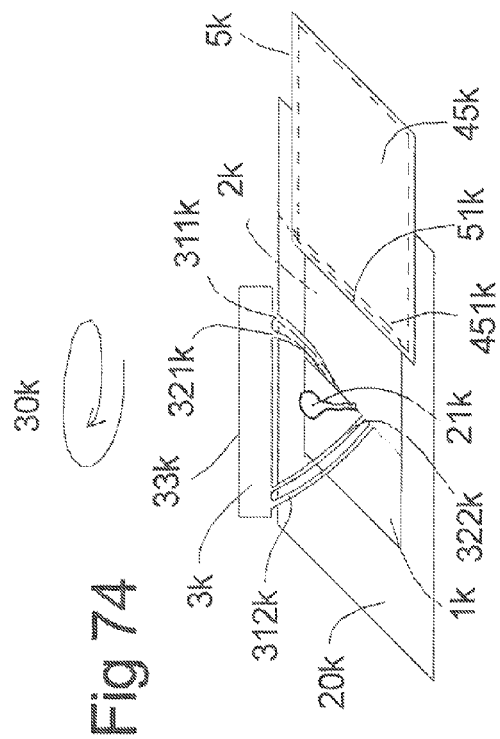

FIG. 74 is an overview where the sections placed on the skin are rotated around the skin tag.

Figure 75:
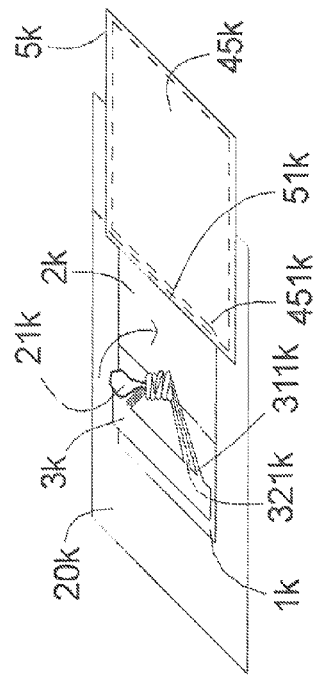

FIG. 75 is an overview showing the occlusion of the base of the skin tag.

Figure 76:
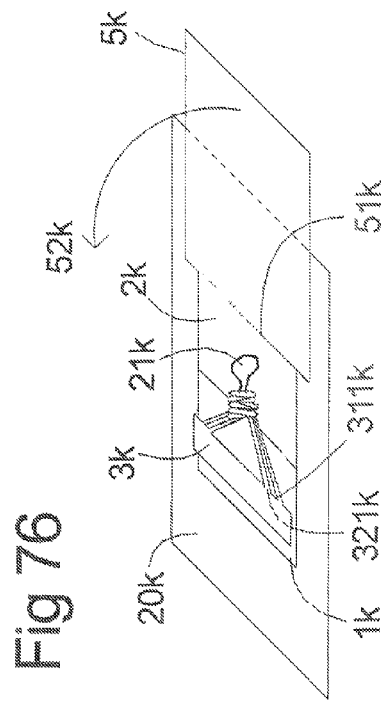

FIG. 76 is an overview showing the skin tag which has been folded down on top of the two sections of the device lying on the skin, and the protective film which has been removed from the fourth section of the device.

Figure 77:
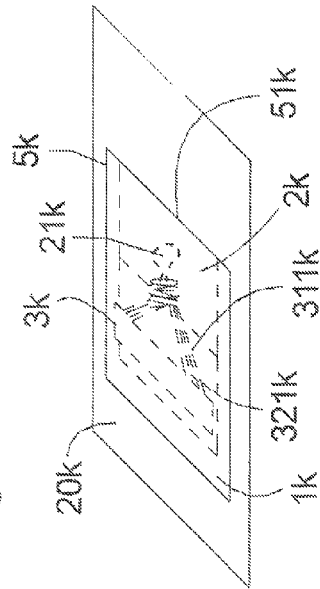

FIG. 77 is an overview illustrating how the fourth section of the device is folded over the occluded skin tag, fastening it on top of the two adhesive sections on the skin while at the same time concealing it from sight, increasing the cosmetic value of the device.

FIG. 78 is an overview illustrating a device consisting of a larger section which is adhesive on the top side and which through to a preexisting fold with an aperture, is stuck to with a smaller section with adhesive on the bottom side. On top of the central part of the smaller section is a low, hollow, cylinder-shaped section with an adhesive outer side. On top of the cylinder-shaped section is a more or less rigid section with an adhesive underside.

FIG. 79 is an overview showing the device placed on the skin such that the skin tag is in the middle of the aperture in the preexisting fold between the larger and smaller section.

FIG. 80 is an overview illustrating how the smaller section in FIG. 79 is stuck to the skin and how the narrow, thread-shaped section which is adhesive on one side and is extending around a part of the larger device is freed and wound around the cylinder, thus occluding the base of the skin tag.

FIG. 81 is a cross section along the line LXXXI-LXXXI in FIG. 80 where the skin tag is pressed and occluded against the cylinder-shaped section which is stuck to the skin.

FIG. 82 is an overview illustrating how the protective film is removed from the larger section which is then folded over the other sections, fixing them to the skin and to the occluded skin tag on the more or less rigid top side of the section.

FIG. 83 is an overview of a little band-shaped device with a centrally located, round, oval or parallelepipedic aperture and an adhesive underside.

FIG. 84 is an overview of a section intended to cover and fix the applied device to the occluded skin tag.

FIG. 85 is an overview, which shows how the skin tag goes through the central aperture and how the device is then stuck to the skin.

FIG. 86 is an overview showing how the two flaps in FIG. 85 are rolled from diametrically opposed directions such that the base of the skin tag is occluded.

FIG. 87 is a cross section along the line XXCVII-XXCVII in FIG. 86, where the section in FIG. 84 fixes the occluded skin tag to the skin surface.

Figure 88:
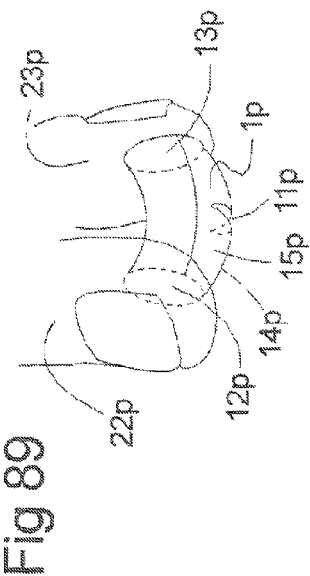

FIG. 88 is an overview of a semi-rigid, tube-shaped, slightly bent device with adhesive on all sides and a little transversal slit in the outer convex surface.

Figure 89:
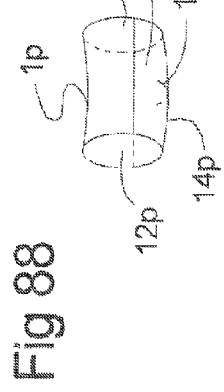

FIG. 89 is an overview showing how the device is clamped together between the thumb and forefinger in such a manner that the slit is widened.

Figure 90:
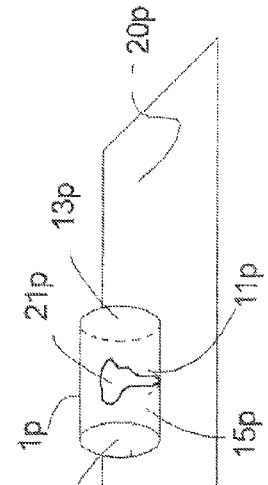

FIG. 90 is an overview where the device clamped together in FIG. 89 has been slid over the skin tag on the surface of the skin.

Figure 91:
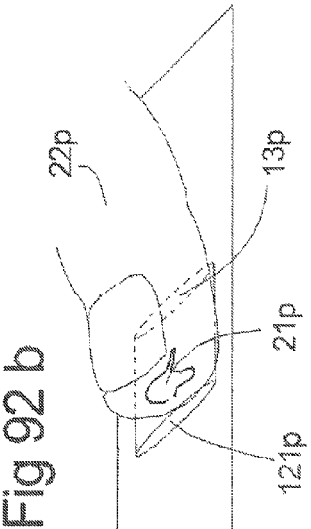

FIG. 91 is an overview showing the device with the slit being stuck to the skin.

Figure 92:
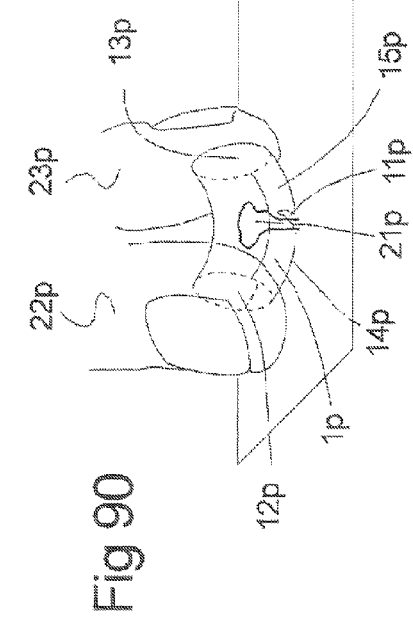
Figure 92:
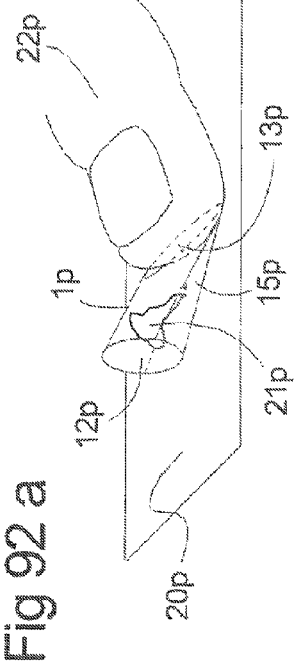

FIG. 92 A is an overview where the skin tag is fixed inside the tube-shaped device.

FIG. 92 B is an overview showing how the occluded skin tag is fixed and concealed on the skin surface.

FIG. 93 is an overview of a band-shaped device with a smaller section which is adhesive on both sides and has a centrally located aperture, a larger section intended to cover and fix the skin tag after occlusion, and a section located in the middle and consisting of two strips in a sharp V-shaped with adhesive on both sides.

FIG. 94 is an overview of the device shown in FIG. 93, where two of the protective films are turned upwards to a vertical position.

FIG. 95 is an overview where the aperture in the smaller section is slid over the skin tag and then stuck to the skin.

FIG. 96 is an overview where the vertical protective film and the section in the sharp V-shaped is bend down over the skin tag and where the larger section will be in a vertical position on the other side of the skin tag.

FIG. 97 A is an overview showing how the occluding effect of the V-shaped device can be controlled using the protective films in FIG. 94.

FIG. 97 B is an overview where the occlusion of the skin tag is completed and the larger section is pulled into the correct position.

FIG. 98 is an overview showing the occluded skin tag being fixed and concealed on the skin surface.

Figure 99:
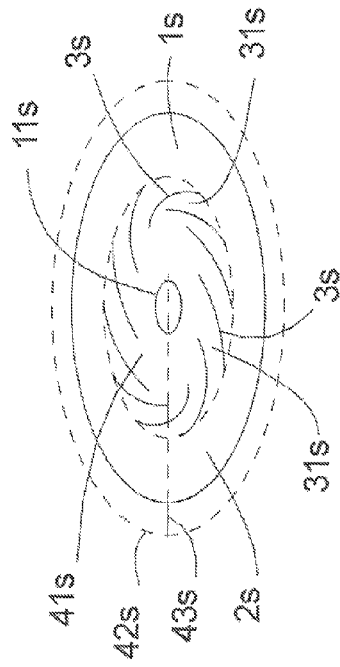

FIG. 99 is an overview of a thin, more or less circular device with a centrally located aperture and an adhesive side which is covered by an inner and outer protective film, slit by an incision to facilitate removal.

Figure 100:
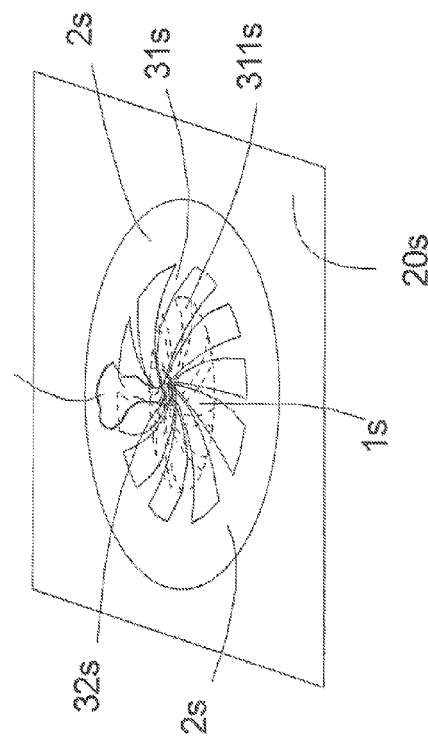

FIG. 100 is an overview showing how radii have been punched or cut though the device in the outer part of the inner protective film.

Figure 101:
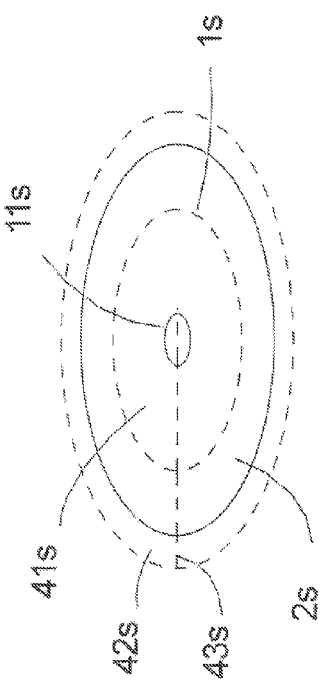

FIG. 101 is an overview where the skin tag has first been slid through the central aperture of the device, where the inner central part is then stuck to the skin.

Figure 102:
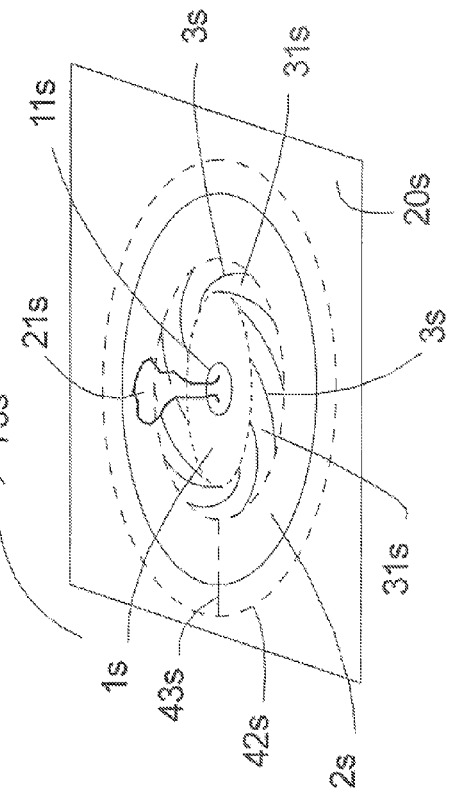

FIG. 102 is an overview showing how, by twisting the free outer section of the device in FIG. 101, the punched radii are wound around the skin tag and occlude the base; following which the outer part has been stuck to the skin.

Figure 103:
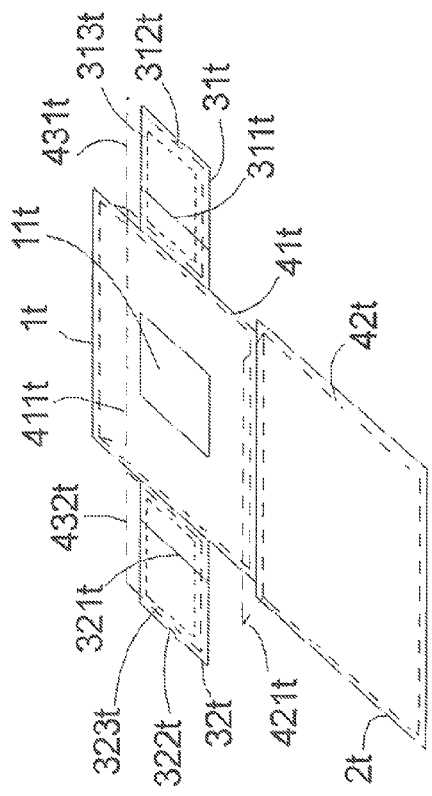

FIG. 103 is an overview of a device where a central section with a central opening on one of its sides is connected with a large section intended to cover and fix the skin tag to the skin surface. On the opposite sides of the central section are a couple of inverted, more or less rigid sections with an adhesive surface and a peripheral softer edge.

Figure 104:
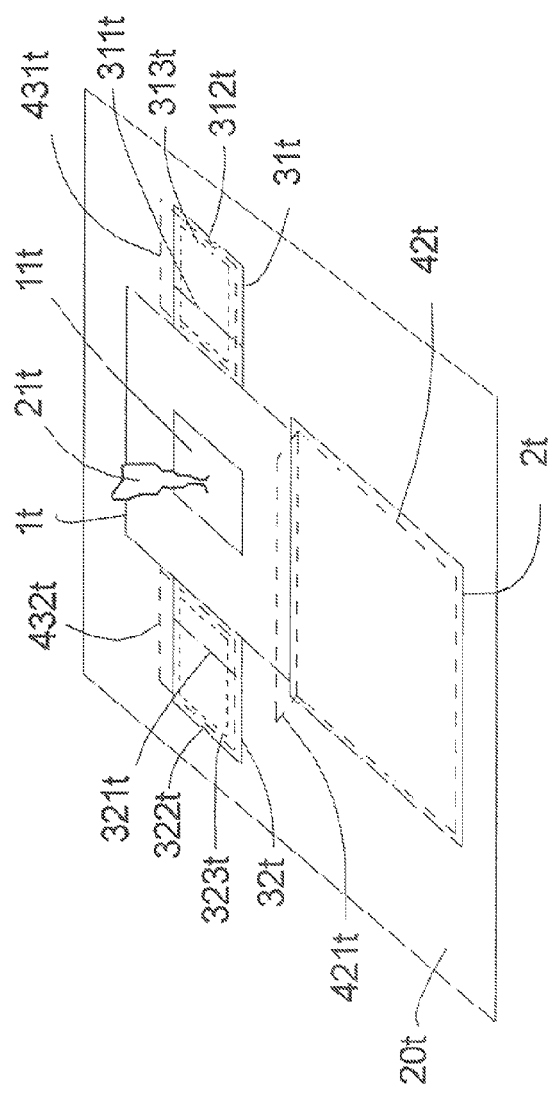

FIG. 104 is an overview showing how the skin tag is folded in the central opening, and the central section of the device is stuck to the skin surface.

Figure 105:
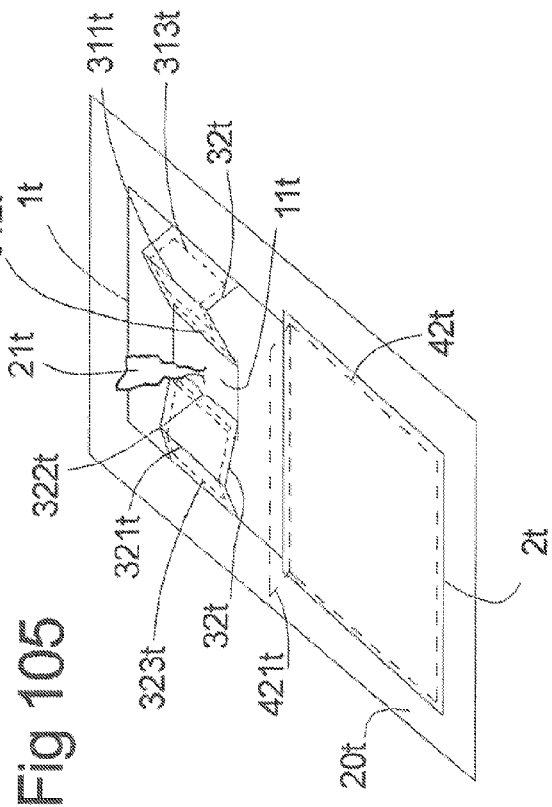

FIG. 105 is an overview where the inversed sections are bent in the central opening and the soft edge of each section is placed against the opposite side of the base of the skin tag.

Figure 106:
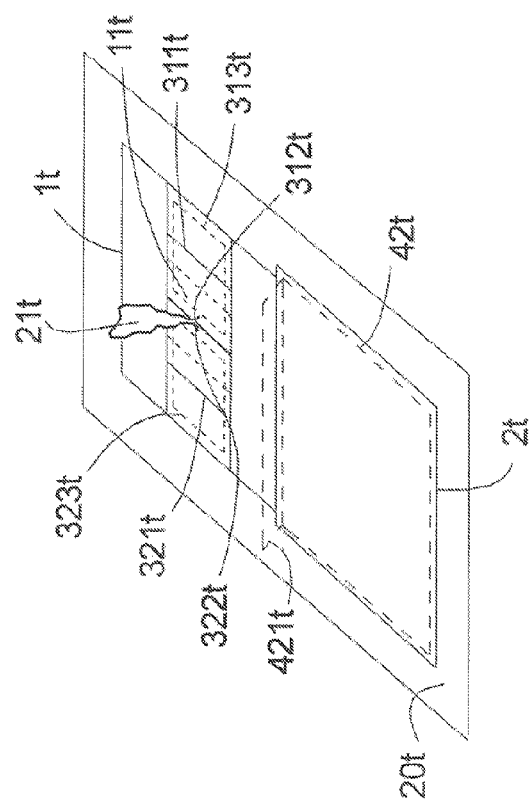

FIG. 106 is an overview showing how the inversed sections are stuck to the skin in the central opening, whereby the base of the skin tag is occluded by the soft elastic edge.

Figure 107:
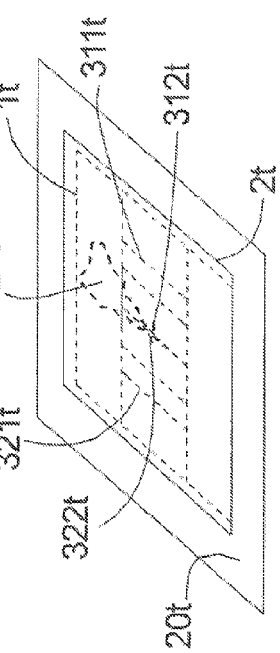

FIG. 107 is an overview showing how the larger section is folded over the occluded skin tag in order to conceal and fix it to the skin.

Figure 108:
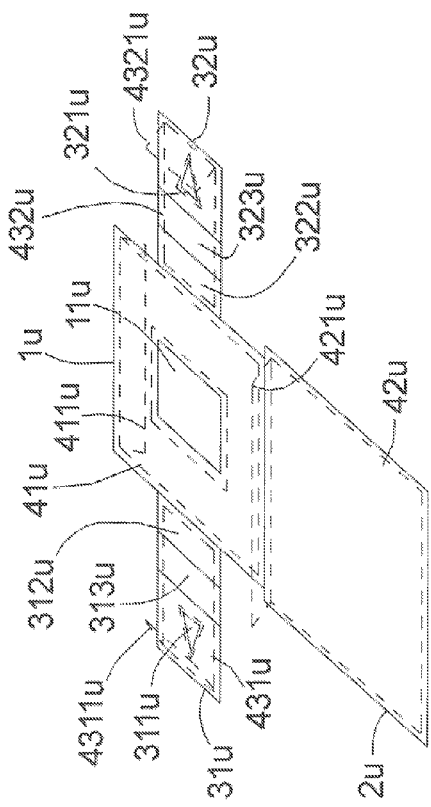

FIG. 108 is an overview of a device according to FIG. 103, where the inversed, more or less rigid sections each have their own triangle-shaped notch.

Figure 109:
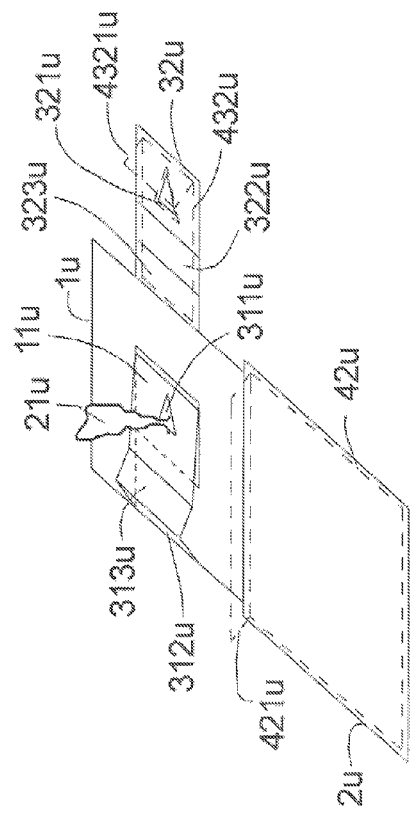

FIG. 109 is an overview showing how the central section of the device is stuck to the skin and how the protective film is removed from one of the inversed sections and how these triangle-shaped notches are slid over the skin tag.

FIG. 110 is an overview showing how the notch of the second inversed section is placed over the skin tag.

FIG. 111 is an overview showing how, by folding over and pulling the excentrically formed, inversed sections, the skin tag can be occluded from two opposite directions.

FIG. 112 is an overview where the larger section is folded over the occluded skin tag, fixing and concealing it on top of the inversed sections.

Figure 113:
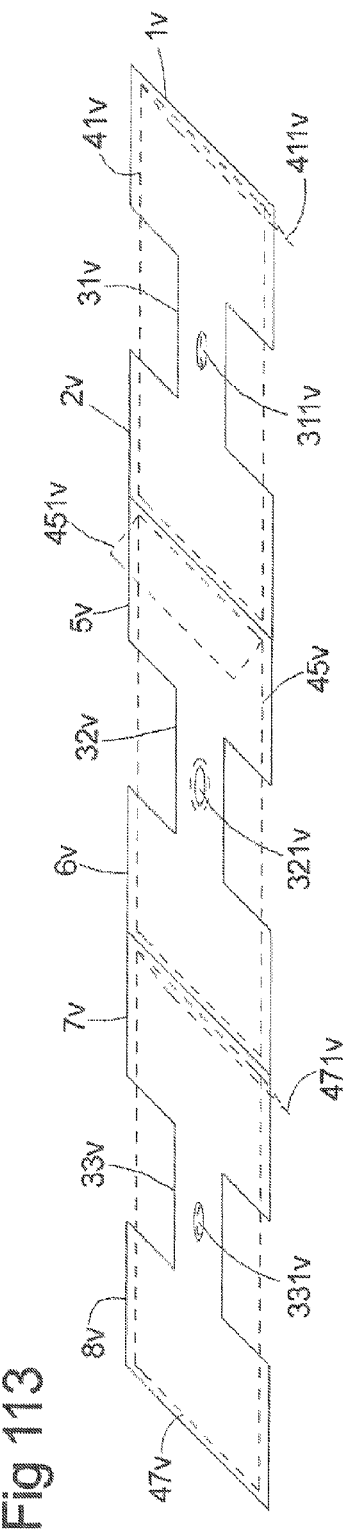

FIG. 113 is an overview of a band-shaped device consisting of three connected, H-shaped sections each with their own adhesive surface. Centrally in each H-shaped section is a punched aperture.

Figure 114:
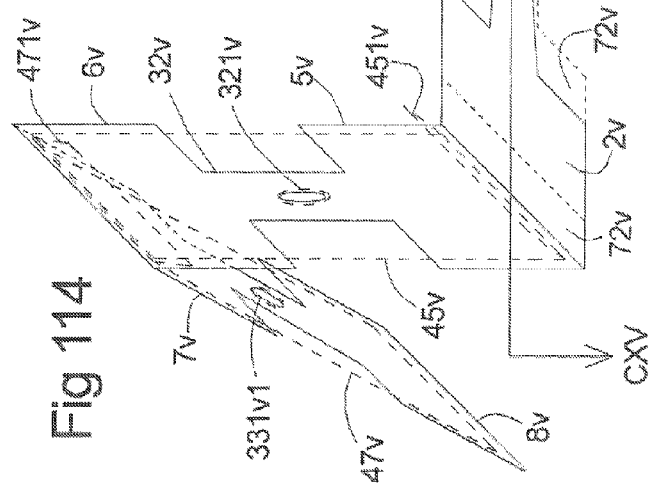

FIG. 114 is an overview of the device where one of the outer sections are stuck to the skin, so that the skin tag sticks up through the punched aperture in the section and how the middle section is raised to a central position such that it can be folded over the skin tag.

Figure 115:
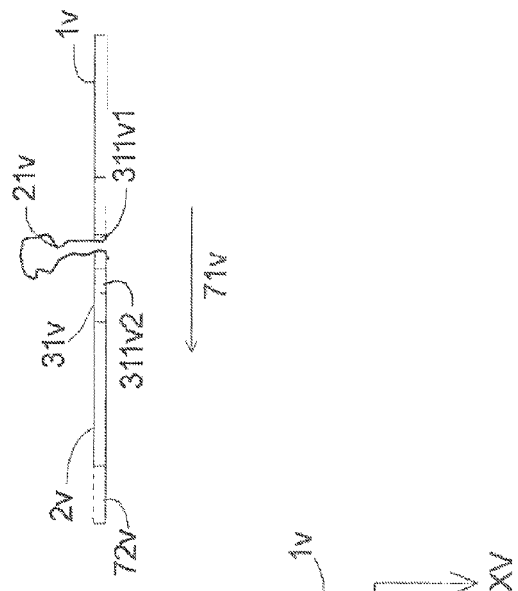

FIG. 115 is a cross section along the line CXV-CXV in FIG. 114, showing how when applied to the skin, the section is stretched in such a manner that the skin tag ends up against the edge of the aperture punched in the section.

Figure 116:
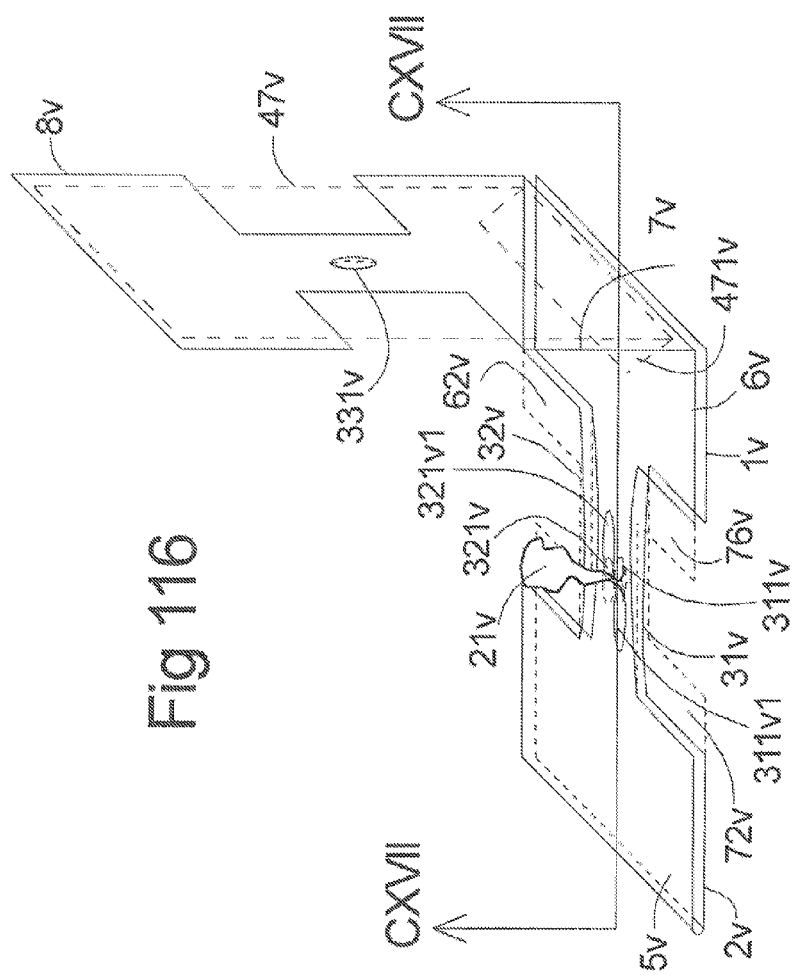

FIG. 116 is an overview where the middle section is folded over the skin tag and stretched such that the central aperture occludes the skin tag and sticks to the section on the skin.

Figure 117:
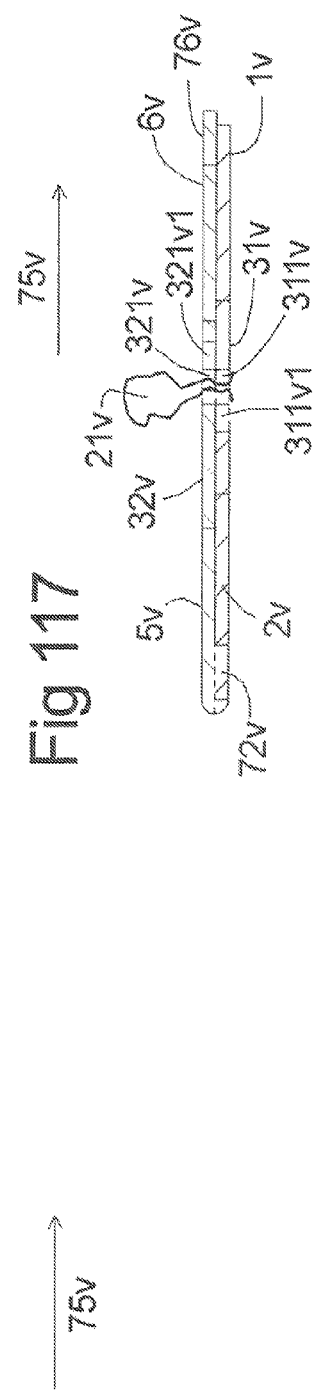

FIG. 117 is a longitudinal section along the line CXVII-CXVII in FIG. 116 showing how the middle section is stretched such that the aperture occludes the skin tag.

Figure 118:
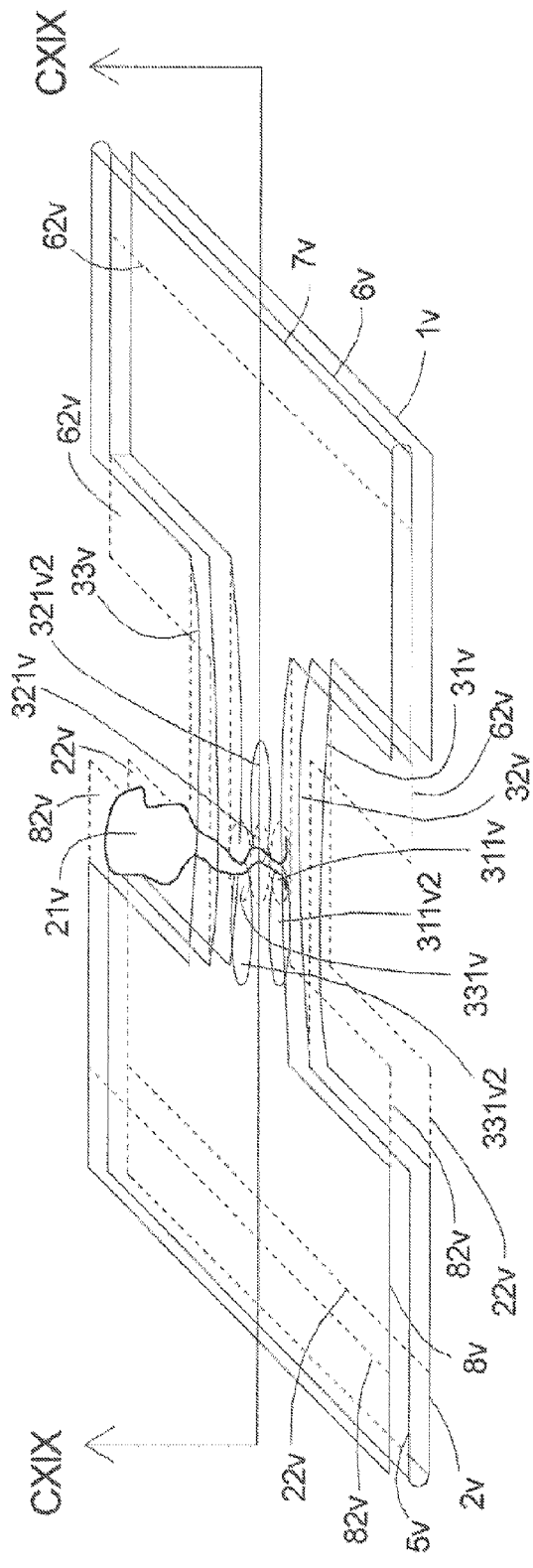

FIG. 118 in relation to the other FIGS. of this embodiment of the invention, this is an enlarged view, where the third section of the device is folded over the skin tag and stretched and stuck on the middle section.

Figure 119:
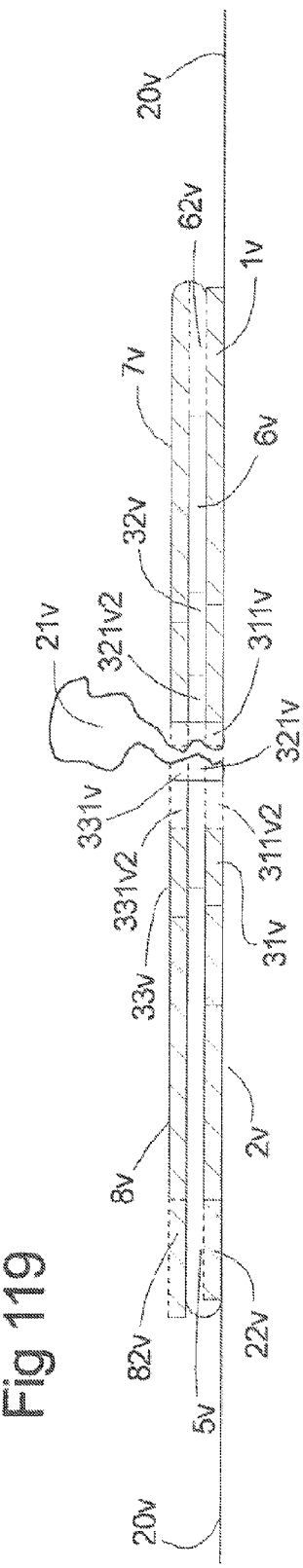

FIG. 119 is a longitudinal section along the line CXIX-CXIX in FIG. 118, which illustrates how the third section is folded over the skin tag and stretched allowing a sufficient occlusion and then stuck on the middle section.

Figure 120:
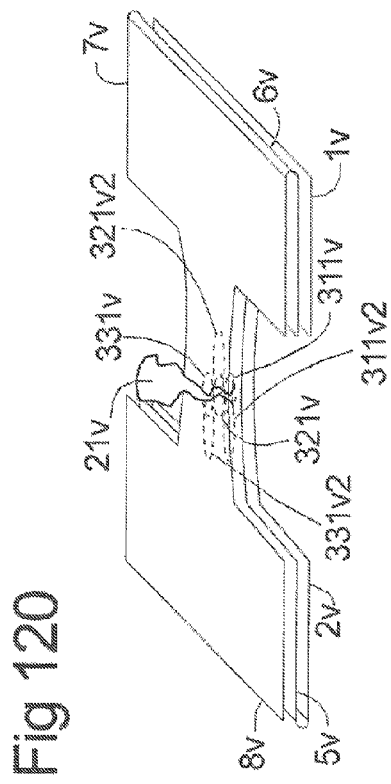

FIG. 120 is a reduced and simplified view of FIG. 118, showing how the base of the skin tag is occluded by opposite application of pressure from the centrally positioned aperture in the three sections.

Figure 121:
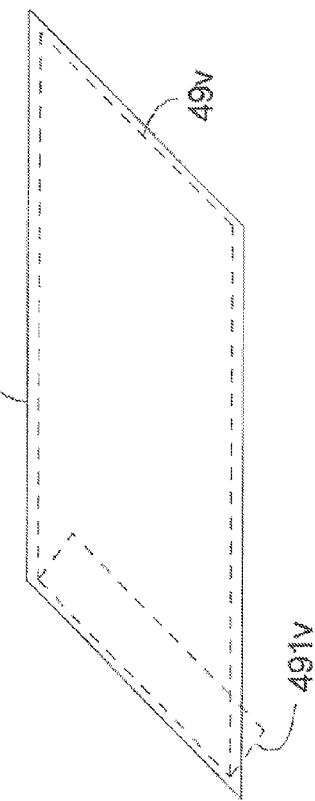

FIG. 121 is an overview showing an separate, thin, more or less elastic section with an adhesive surface, the total extent of which is larger than the total area of the device applied to the skin surface in FIG. 120.

Figure 122:
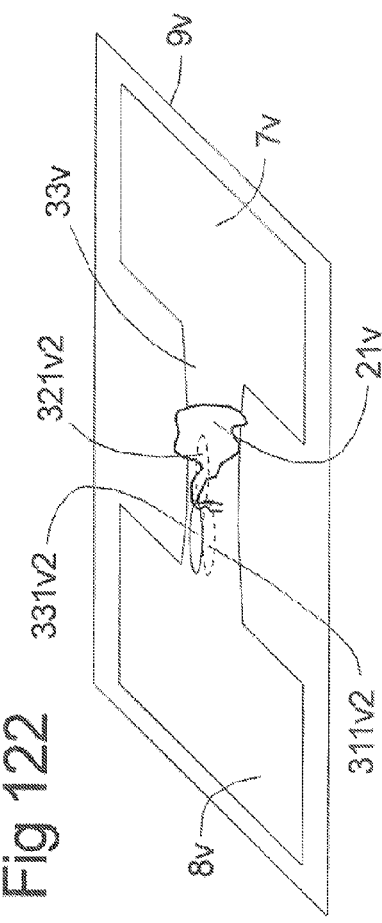

FIG. 122 is an overview where the separate section in FIG. 121 is stuck on top of the applied device and onto the skin surface, fixing and concealing the occluded skin tag.

Figure 123:
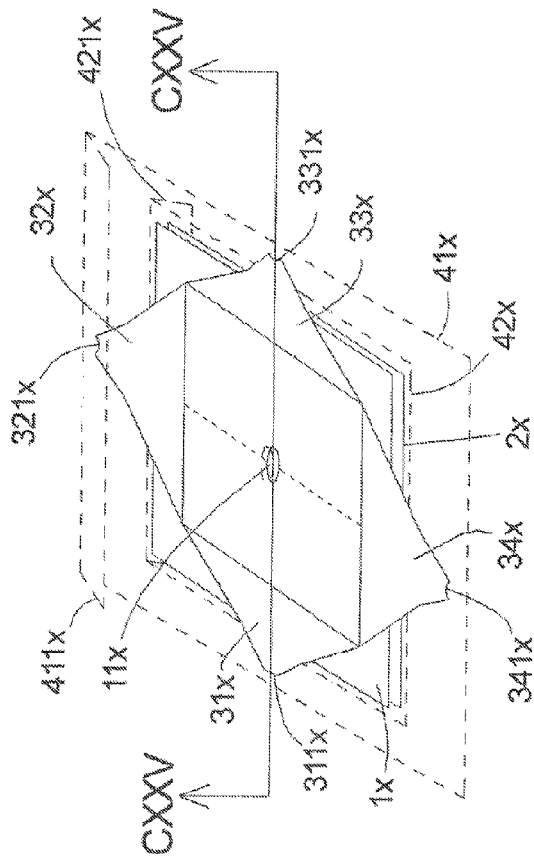

FIG. 123 is an overview showing a device with a more or less flexible, lower section consisting of a central aperture and two adhesive surfaces; and an upper, more rigid section which is equal in size, with four equally large, paired, opposite flaps that have been punched out in the center.

Figure 124:
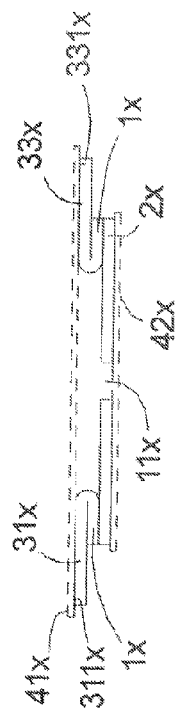

FIG. 124 is a cross section along the line CXXIV-CXXIV in FIG. 123, where the lower section with its central aperture and the upper section with its punched, outwards oriented flaps are stuck together through an outer frame extending around the device.

Figure 125:
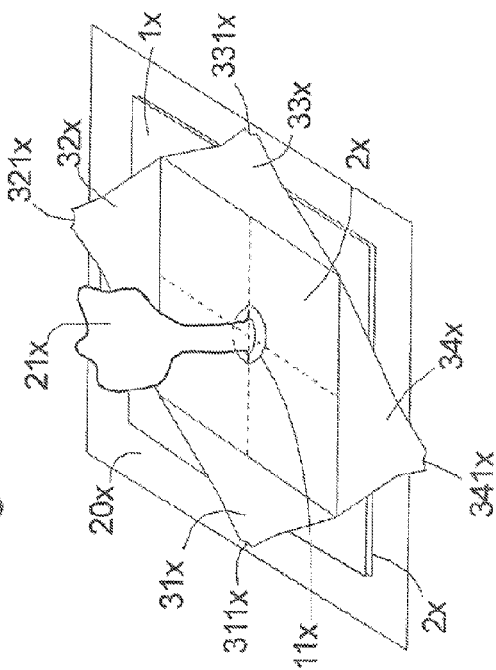

FIG. 125 is an overview showing how the device is slid over the skin tag and then stuck to the skin.

Figure 126:
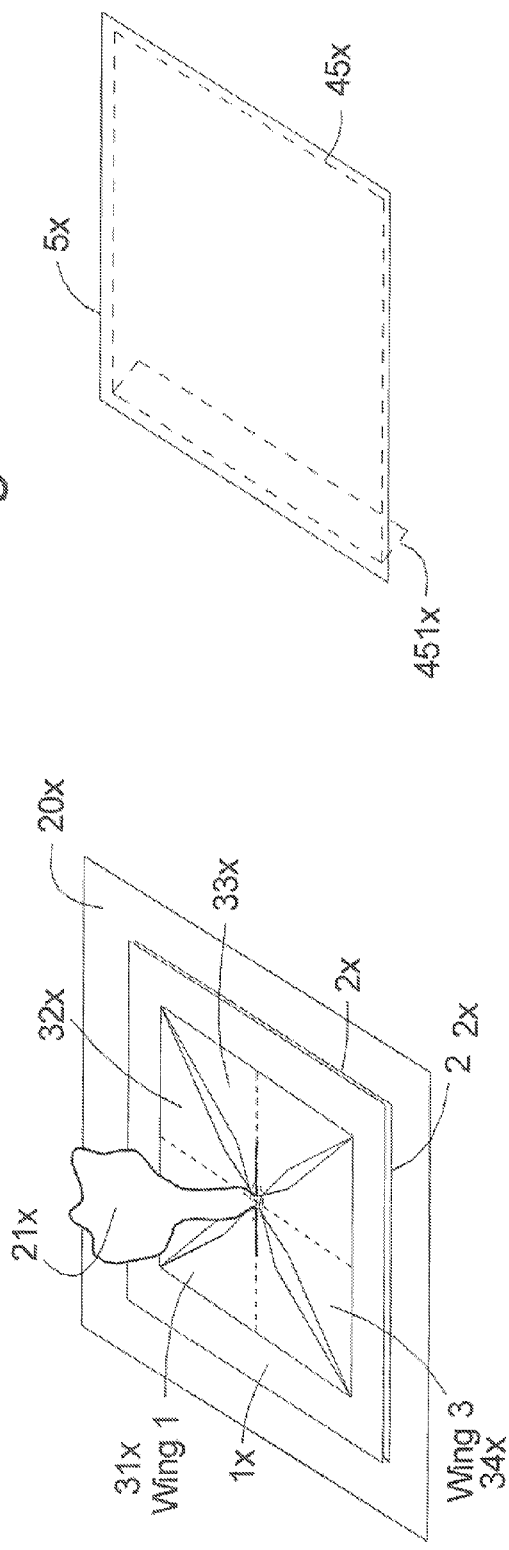

FIG. 126 is an overview illustrating how the punched out flaps from the four sides are turned inwards towards the centre and the base of the skin tag which thereby is occluded.

Figure 127:
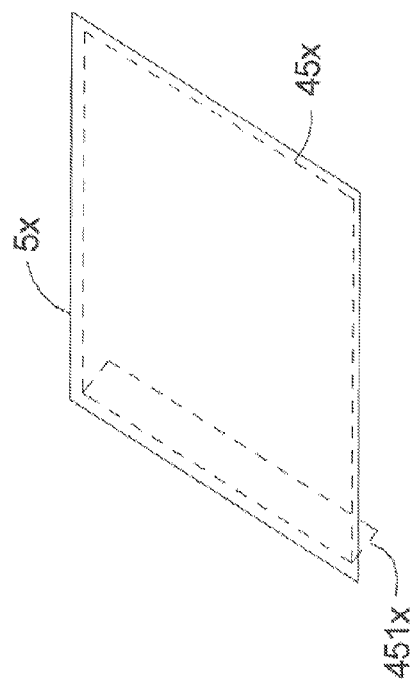

FIG. 127 is an overview showing an independent device for covering and fixing the occluded skin tag to the skin surface.

Figure 128:
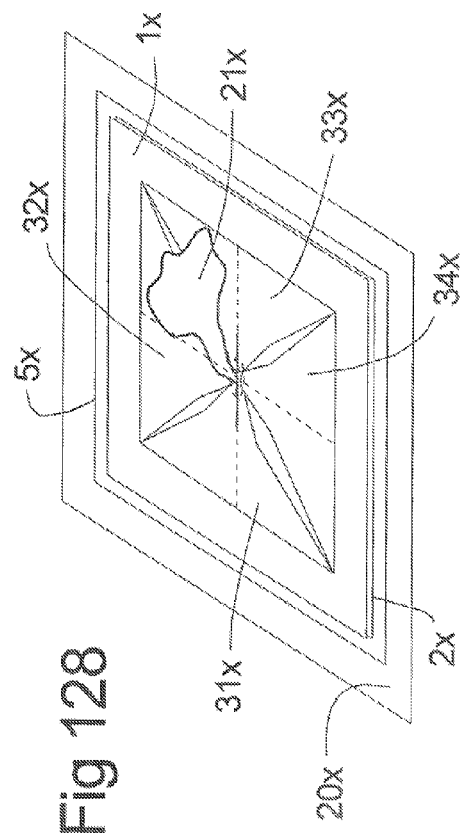

FIG. 128 is an overview where the occluded skin tag located in the device is concealed and fixed to the skin surface.

Figure 129:
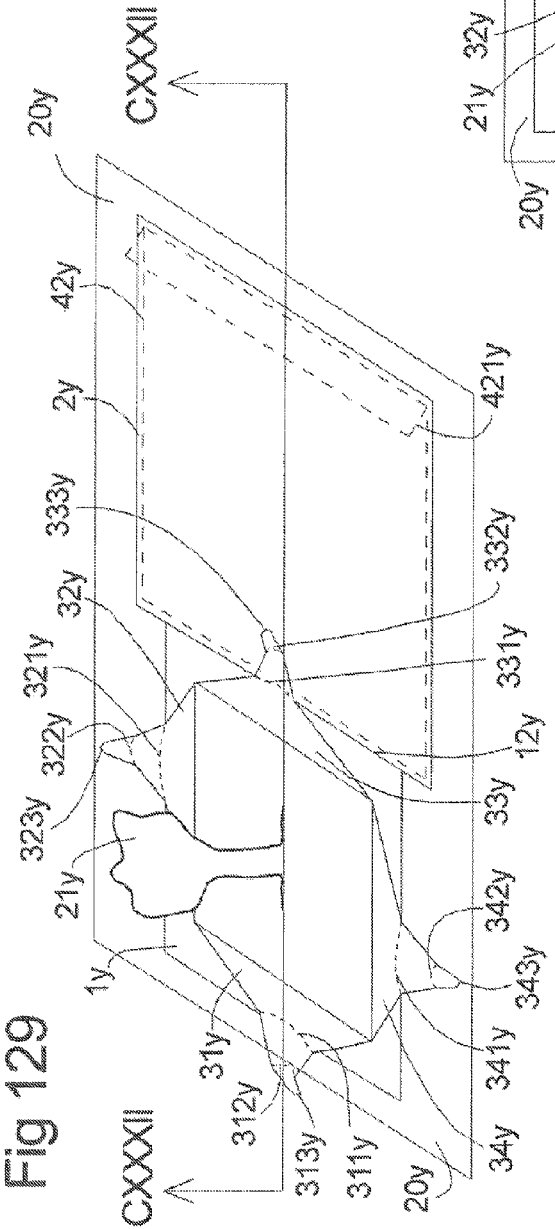

FIG. 129 is an overview of an alternative embodiment to that described in FIG. 123. The thin, band-shaped device in FIG. 129 consists of two connected devices, where the more or less hard section is stuck to the skin such that the skin tag ends up in the middle of the open central part of the section, which was created by punching four equally large flaps in which reinforcing radii were formed.

Figure 130:
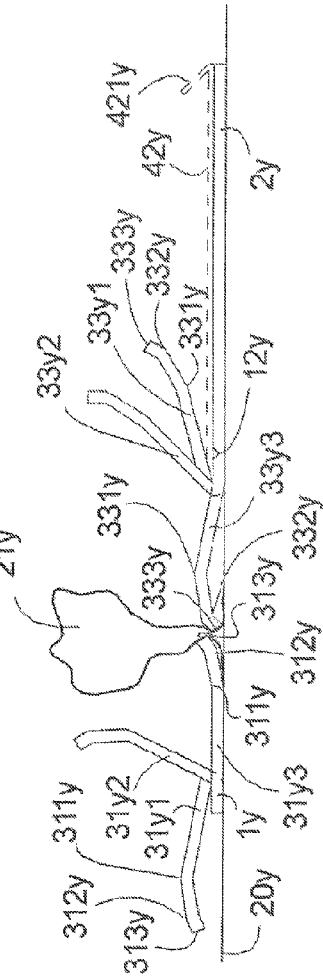

FIG. 130 is a longitudinal section along the line CXXXII-CXXXII in FIG. 129, showing how the radii formed in the flaps can influence the occlusion of the base of the skin tag when they are stuck to the skin in the central part of the device.

Figure 131:
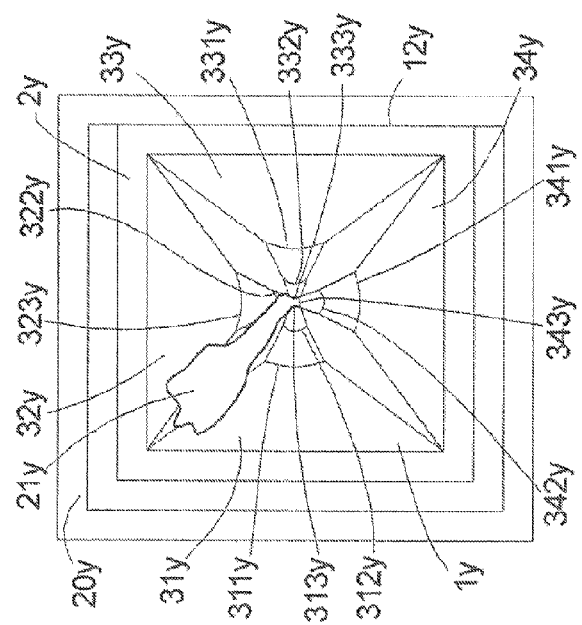

FIG. 131 is an overview where the other section of the device has been stuck over, thus fixing the occluded skin tag to the skin.

FIG. 132 is an overview of an alternative device to that described in FIGS. 99-102. According to this embodiment of the invention, the device consists of two circular sections between which there is a thin, more of less elastic film.

FIG. 133 is an overview showing how the circular sections are separated, stretching the thin film in FIG. 134.

FIG. 134 is a cross section along the line CXXXIV-CXXXIV in FIG. 133 and illustrates the position of the thin film and protective film.

FIG. 135 shows how the device in the cross section in FIG. 134 is slid over the skin tag and stuck on the skin surface.

FIG. 136 is an overview where the upper free section is rotated and the thin film in FIG. 134 is wound around the base of the skin tag.

FIG. 137 is a cross section along the line CXXXVII-CXXXVII in FIG. 136 where the base of the skin tag is occluded and where the outer section is to be stuck to the skin surface so that the applied device finally is fixed to the skin.

Figure 138:
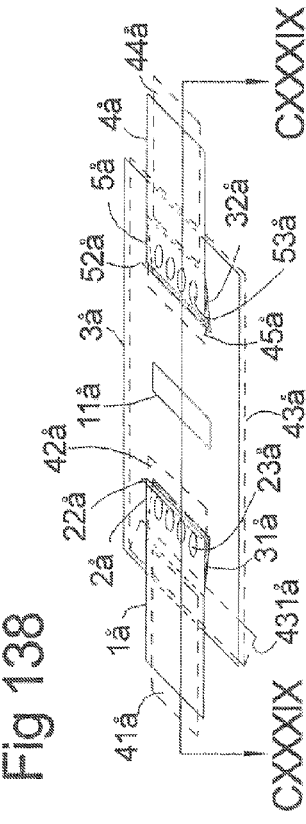

FIG. 138 is an overview showing how two of the sections of the device with lever are stuck to the third section.

Figure 139:
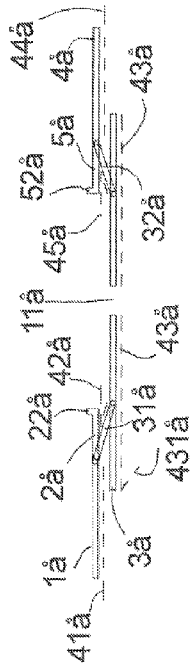

FIG. 139 is a cross section along the line CXXXIX-CXXXIX in FIG. 138 showing the positions of the lever and protective films on the sections comprised in the device.

Figure 140:
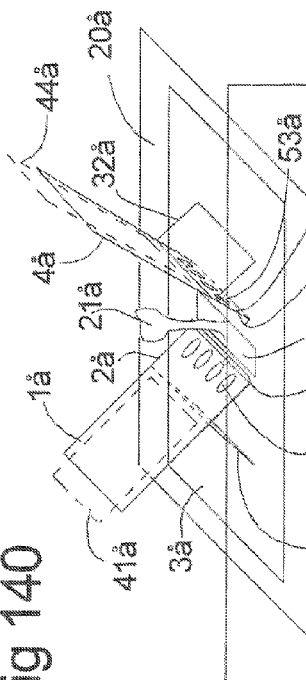

FIG. 140 is an overview where the device has been stuck to the skin and the ends of the two sections movable through the lever are placed against the base of the skin tag.

Figure 141:
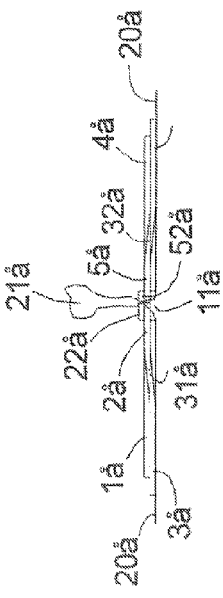

FIG. 141 is a longitudinal section along the line CXXXXI-CXXXXI in FIG. 140, in which the base of the skin tag is occluded by the two moving sections, which together with their lever are stuck to the upper side of the third section.

FIG. 142 is an overview of a device with a spiral, band-shaped section with two band-shaped sections on both sides, which because of a simple fold can be divided into two parts where the parts outside the spiral have adhesive surfaces.

FIG. 143 is an overview showing an independent section intended to cover the device described in FIG. 142 on the skin.

FIG. 144 is a vertical side view of the device according to FIG. 142, which illustrates the positions of the spiral section and the other two sections stuck to it, including their folds and adhesive surfaces.

FIG. 145 is a side view of the device according to FIG. 144, which shows how, by squeezing together the two sections fixed to the spiral section, can create an opening in part of the spirals.

FIG. 146 is a side view of FIG. 145, where the spiral section with the occluded skin tag, through one of the sections stuck to the spiral, is stuck to the skin and where the other section stuck to the spiral is stuck to the upper side of the spiral and where the entire applied spiral is finally covered by the section described in FIG. 143.

FIG. 147 is a perspective view of a device with three sections.

FIG. 148 is a perspective view showing how one of the sections is stuck to the skin.

FIG. 149 is a perspective view showing how the other section is stuck to the skin during simultaneous occlusion of the skin tag.

FIG. 150 is a perspective view where the third section is folded over the two others and conceals and stabilises the occluded skin tag on the surface of the skin.

FIG. 151 is a perspective view of a lid associated to the device with a convex, resilient wing on the lower side.

FIG. 152 is a perspective view of a box-formed section of the device in FIG. 151 with a wing fixed in the bottom of the box adjacent to a semicircular aperture.

FIG. 153 is also a perspective view illustrating how the sections in FIGS. 151 and 152 are connected.

Figure 154:
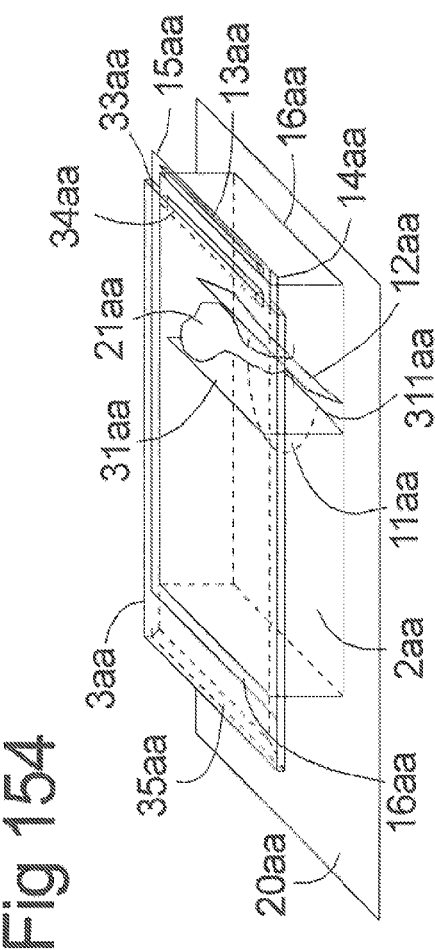

FIG. 154 is a perspective view of how sections in the FIGS. 151 and 152 can be repositioned in relation to each other so that their respective wings occlude the base of the skin tag.

Figure 155:
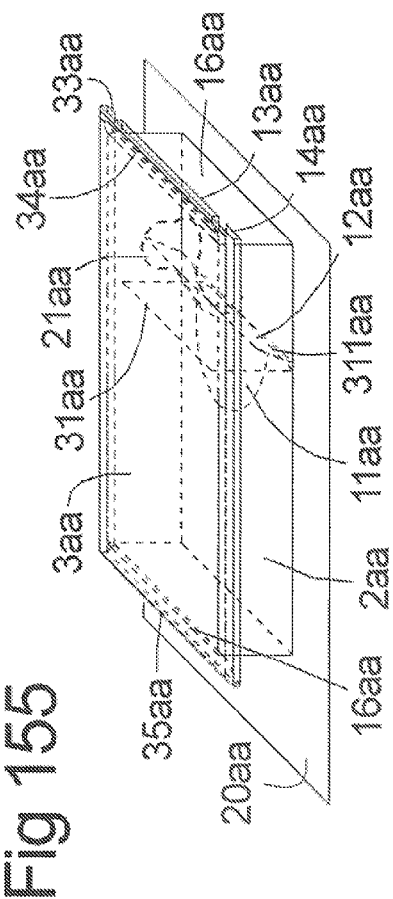

FIG. 155 is perspective view of the device shown in FIG. 53 applied to skin surface, where the skin tag is occluded and simultaneously concealed and fixed to the skin surface.

FIG. 156 is an overview of a device where a more or less smaller, flanged wheel with an O-ring is located above a more or less larger, flanged wheel which has an adhesive lower side and a little indentation in one of the edges.

FIG. 157 is a cross section along the line CLVII-CLVII in FIG. 156 and illustrates the positions of the O-ring, the indentation and the protective film on the adhesive underside.

FIG. 158 is a cross section of FIG. 156 where the device shown in FIG. 156 has been stuck to the skin surface with the skin tag in the indentation, and where the O-ring has been grasped between the thumb and the forefinger.

FIG. 159 is a cross section of FIG. 158 where the O-ring has been rolled down over the skin tag which is occluded.

Figure 160:
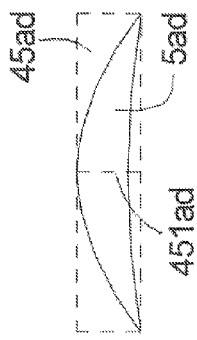

FIG. 160 is an overview of a section of a variant of the device shown in FIG. 156 with a modified indentation, where the upper flanged wheel with the O-ring is tilted in relation the lower wheel with the adhesive underside covered by a protective film.

Figure 161:
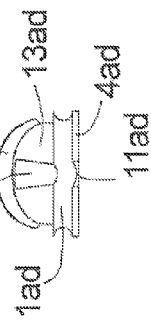

FIG. 161 is a cross section along the line CLXI-CLXI in FIG. 160 and shows the position of the O-ring, the indentation and the adhesive underside with its protective film.

Figure 162:
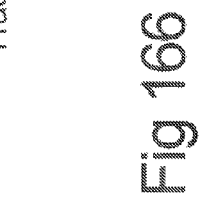

FIG. 162 is an overview of a crescent-shaped section of a device.

Figure 163:
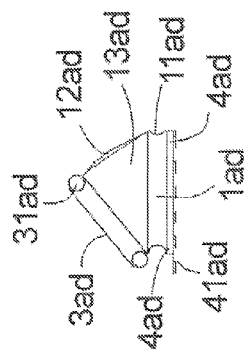

FIG. 163 is a front view of the section in FIG. 160, and shows a magnified indentation between the two slanted wheels.

Figure 164:
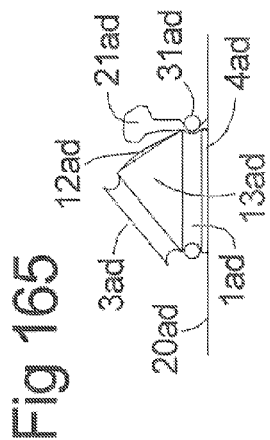

FIG. 164 is a side view showing how the section in FIG. 163 is stuck to the skin with the skin tag in the indentation.

Figure 165:
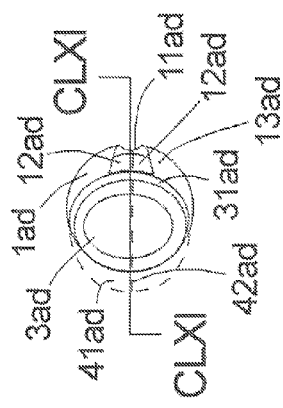

FIG. 165 is a side view illustrating how the O-ring in FIG. 164 is rolled down using a finger and the base of the skin tag is occluded.

Figure 166:
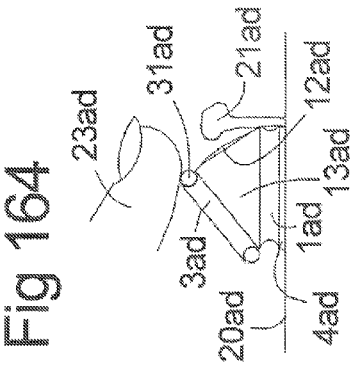

FIG. 166 is a side view where the crescent-shaped section in FIG. 162 is applied to the magnified indentation in FIG. 163 to conceal and stabilise the skin tag on the surface of the skin.

FIG. 167 is an overview of another variant of the device shown in FIG. 156 where the stacked flanged wheels have been stuck to two band-shaped, adhesive devices and where the O-ring is applied with a special strap.

FIG. 168 is a longitudinal section along the line CLXVII-CLXVII in FIG. 167 illustrating the indentation and aperture in one of the band-shaped devices and the strap.

FIG. 169 is a side view of FIG. 168 showing how the skin tag protrudes through the aperture of the band-shaped section which is stuck to the skin, and how the O-ring with the strap can be pulled over the skin tag.

FIG. 170 is a side view where the occluded skin tag has been folded in the upper, flanged wheel.

FIG. 171 is a side view where the other band-shaped section is bent over the wheel with the occluded skin tag which is concealed and fixed to the skin surface.

Figure 172:
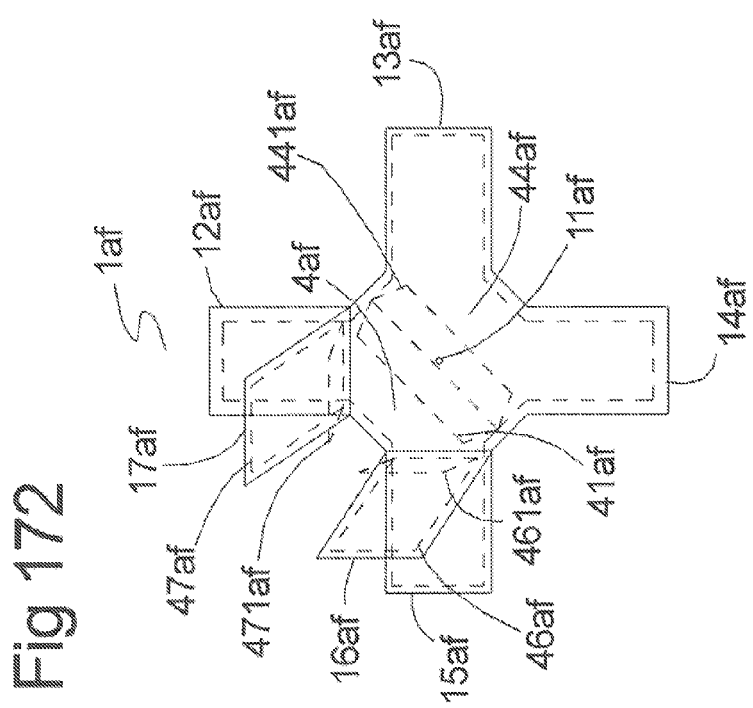

FIG. 172 is a perspective view of the cross-shaped, thin device with an adhesive underside, a minute central aperture and two extra arms with an adhesive upper side.

Figure 173:
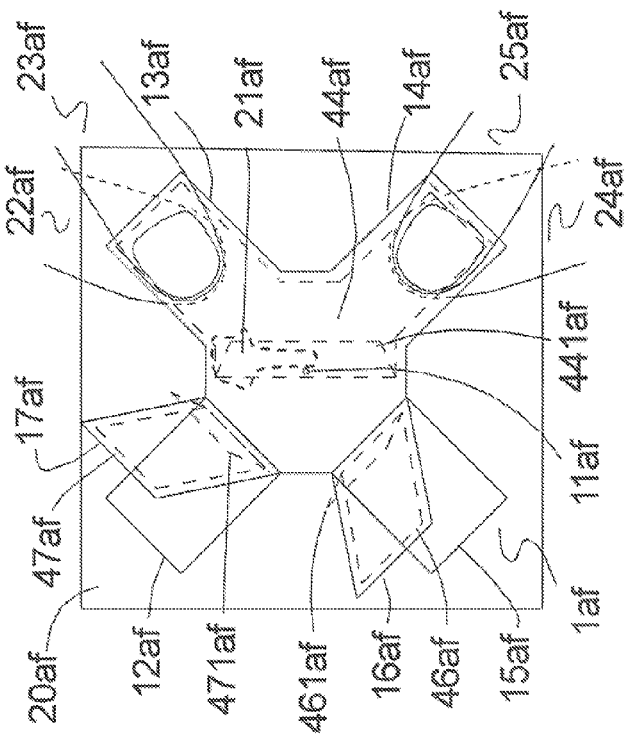

FIG. 173 is a perspective view, illustrating how the protective film is removed from one side of the cross-shaped device in FIG. 172 which is then stuck to the skin surface.

Figure 174:
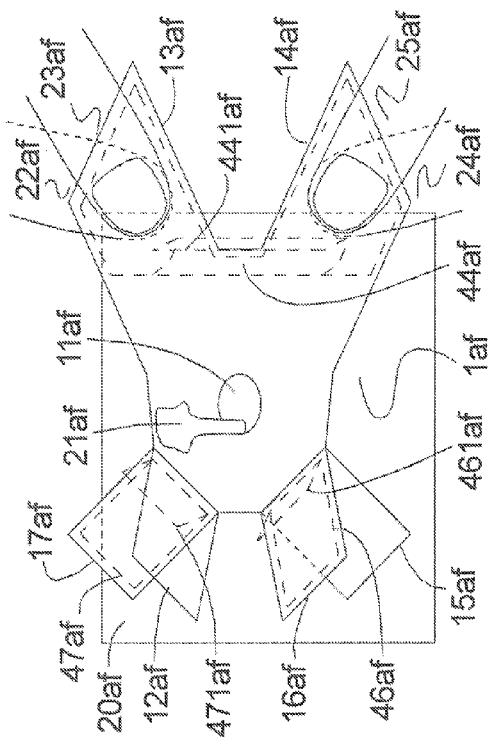

FIG. 174 is a perspective view where the free arms in FIG. 173 are stretched on the device by means of the fingers so that the little central aperture is widened so much that it can be stretched over the skin tag.

Figure 175:
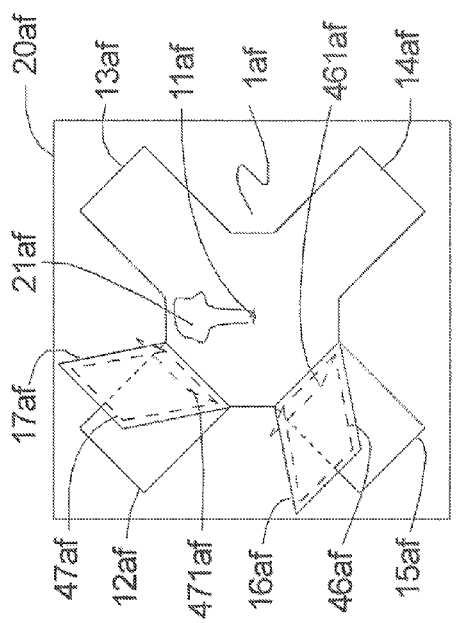

FIG. 175 is a perspective view where the central aperture contracts and occludes the base of the skin tag after having been stretched in FIG. 174, and the aperture section is stuck to the skin.

Figure 176:
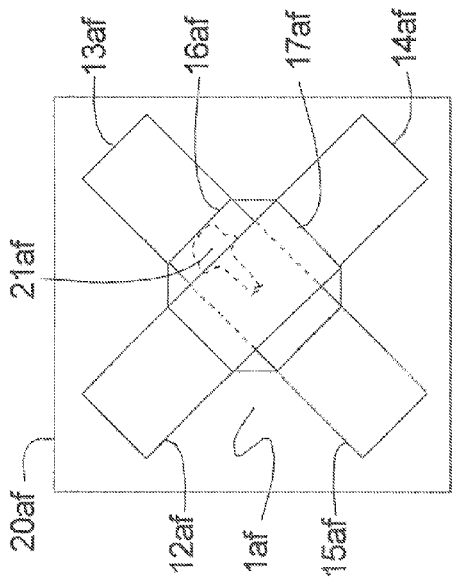

FIG. 176 is a perspective view illustrating how the two remaining arms are stuck over each other on top of the skin tag which is concealed and fixed to the skin surface.

Figure 177:
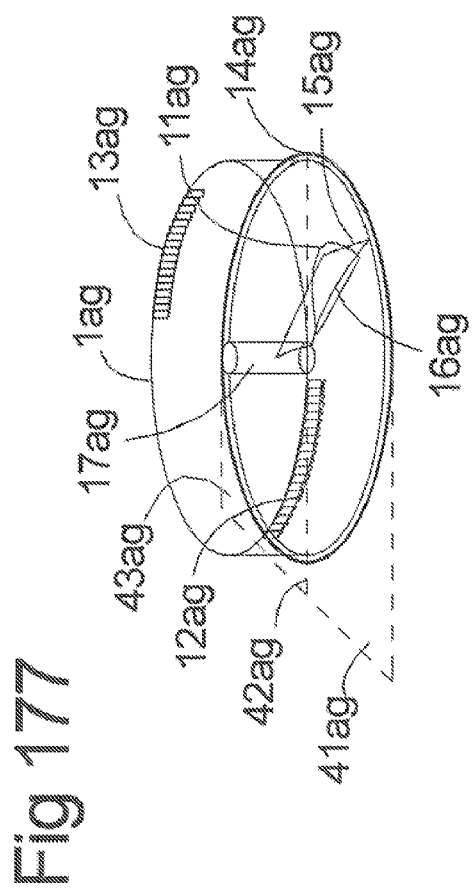

FIG. 177 is a perspective view of a round, low, circular, bowl-shaped section with an adhesive underside and a small, central cylinder located at the periphery of an aperture in the bottom, from which a wing and two thin lock strips located in the upper periphery extend.

Figure 178:
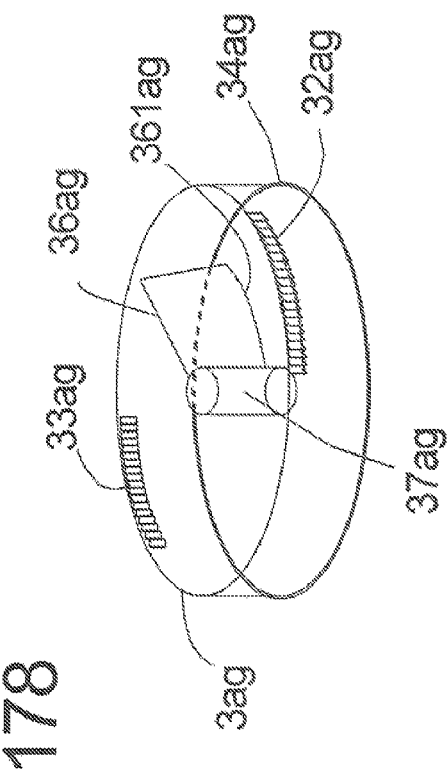

FIG. 178 is a perspective view of a low, circular, lid-shaped section with a large, centrally located cylinder, a wing hanging from the top and two lock strips.

Figure 179:
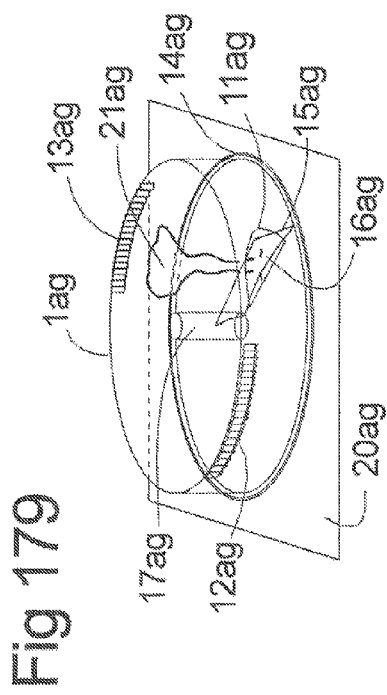

FIG. 179 is a perspective view illustrating how the bowl-shaped section in FIG. 177 is stuck to the skin with the skin tag protruding through the aperture at the bottom.

Figure 180:
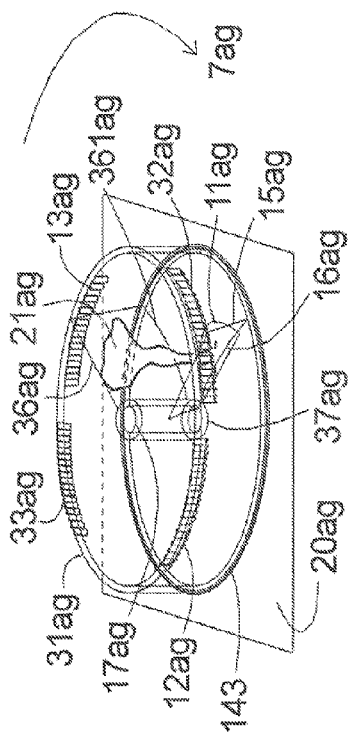

FIG. 180 is a perspective view where the lid-shaped device in FIG. 178 is placed over the bowl-shaped section shown in FIG. 179 such that the central cylinders engage each other and a wing will be located behind the skin tag and the other in front of the skin tag.

Figure 181:
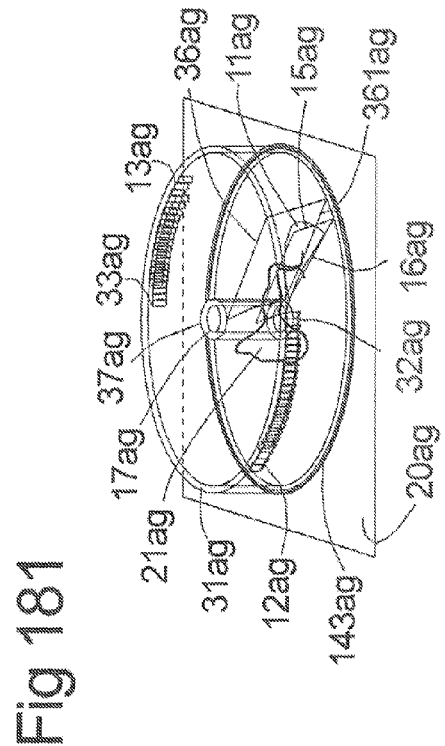

FIG. 181 is a perspective view where the lid-shaped device in FIG. 180 is rotated so that the wings occlude the base of the skin tag and at the same time are locked into place by the lock strips facing each other.

FIG. 182 is a perspective view of a band-shaped section with an adhesive underside covered by two protective films.

FIG. 183 is a perspective view of a thin, circular section with a central aperture around which a detachable thread is wound, and with an adhesive underside covered by two protective films.

FIG. 184 is a perspective view showing how the thin, circular section in FIG. 183 is stuck to the skin so that the skin tag protrudes through the central aperture.

FIG. 185 is a perspective view where the thread is tied around the skin tag with one or several knots or loops.

FIG. 186 is a perspective view illustrating how the knots are pulled together thus occluding the base of the skin tag, and how the band-shaped section in FIG. 182 is stuck over the occluded skin tag which is concealed and fixed to the skin surface.

Figure 187:
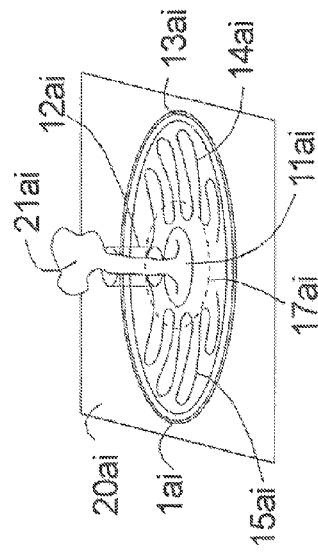

FIG. 187 is a perspective view illustrating a low, lid-shaped section with an outwardly directed edge.

Figure 188:

FIG. 188 is a perspective view showing a thin, circular section with an bottom adhesive on the underside, in which there is a central aperture with a thread wound around the aperture and a cylinder located in the aperture and a fold around the circumference.

Figure 189:
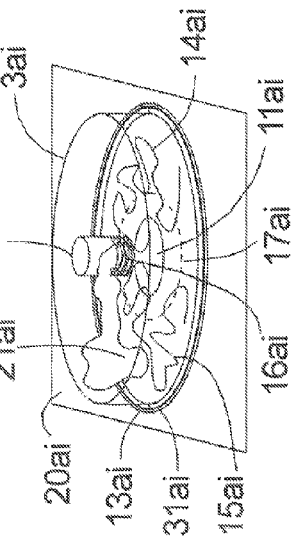

FIG. 189 is a perspective view where the thin section described in FIG. 188 is stuck on the skin, and the skin tag is in the central aperture near the cylinder.

Figure 190:
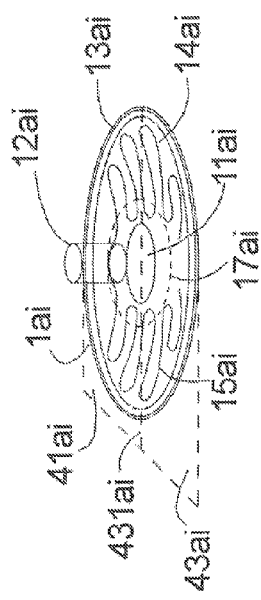

FIG. 190 is a perspective view where the thread in FIG. 189 is knotted and wound around the base of the skin tag and the cylinder.

Figure 191:
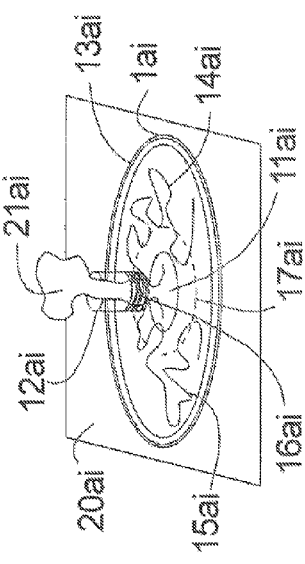

FIG. 191 is a perspective view showing how the lid-shaped section in FIG. 187 is locked into the circular fold in the thin section located on the skin in order to protect the skin tag which is occluded by the cylinder.

Figure 192:

FIG. 192 is a perspective view showing a lid-shaped section with an outwardly directed edge.

Figure 193:
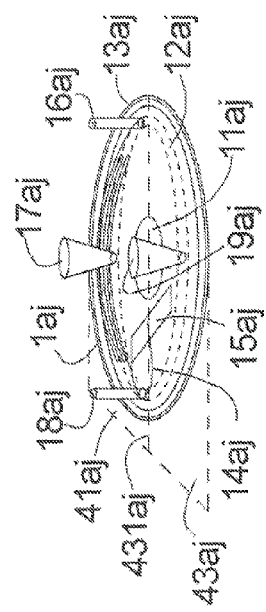

FIG. 193 is a perspective view showing a thin, circular section with an adhesive underside, a central aperture, a peripheral ring with small cones and small pins, a thread tied around the aperture, and an upturned, peripheral outer edge.

Figure 194:
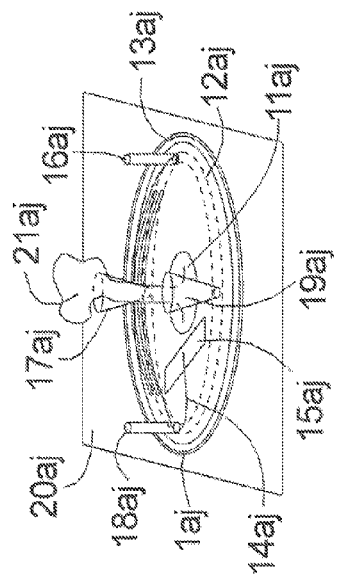

FIG. 194 is a perspective view where the circular sections in FIG. 193 are stuck to the skin with the skin tag in the middle of the central aperture.

Figure 195:
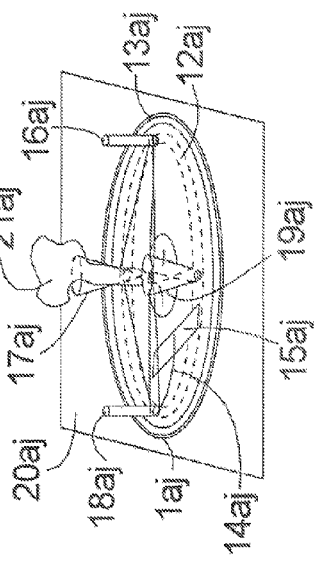

FIG. 195 is a perspective view showing how the thread in FIG. 194 is wound alternately around the pins, the base of the skin tag and the cones.

Figure 196:
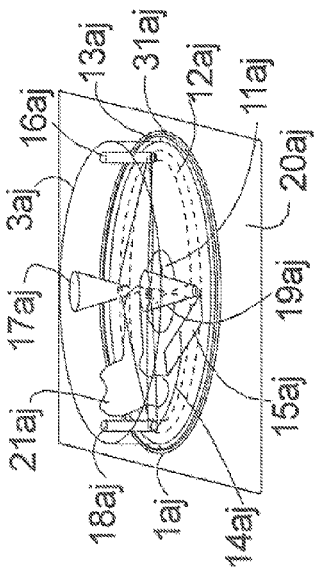

FIG. 196 is a perspective view where the lid-shaped section in FIG. 192 is snapped into place on the peripheral outer edge of the section with the occluded skin tag, shown in FIG. 195.

FIG. 197 is an overview of a device with three sections where the middle section has a central aperture, around which there are two interconnected loops, each loop being connected to a peripheral section located on each side of the middle section.

FIG. 198 is a cross section of FIG. 197 along the line ClIC-ClIC illustrating the position of the adhesive surfaces of the three sections, all of which are independent of each other.

FIG. 199 is a perspective view illustrating how the central sections in FIG. 197 are stuck to the surface of the skin with the skin tag in the middle of the central aperture.

Figure 200:
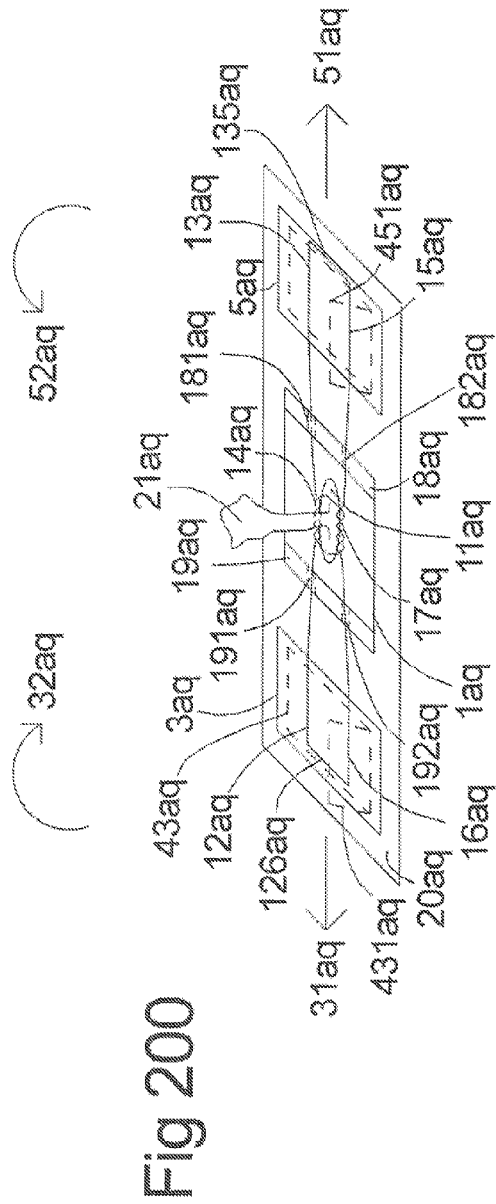

FIG. 200 is a perspective view where the two outer peripheral sections in FIG. 199 have been drawn out from the central section so that the loops with knots are pulled around the base of the skin tag.

Figure 201:
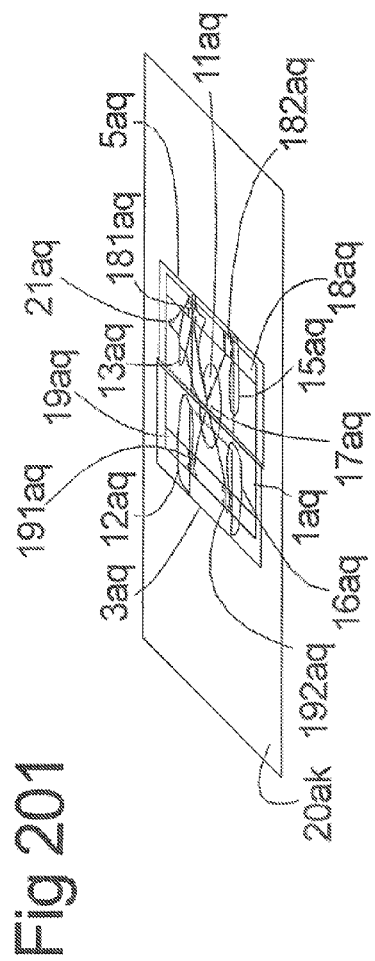

FIG. 201 is a perspective view showing how the loops in FIG. 200 are pulled apart occluding the base of the skin tag, and how the peripheral sections are turned and stuck on top of the occluded skin tag in an overlapping fashion.

FIG. 202 is a perspective view of a screw-shaped section.

FIG. 203 is a perspective view of a little brick-shaped section with a threaded aperture and an adhesive underside.

FIG. 204 is a cross section according to the line CCIV-CCIV in FIG. 203, showing the aperture under the thread and the flexible band located at the bottom inside the aperture.

FIG. 205 is a perspective view of a band-shaped section with an adhesive underside.

FIG. 206 is a longitudinal section along the line CCVl-CCVl in FIG. 203, illustrating how the screw section in FIG. 202 is screwed into the brick-shaped section in FIG. 203.

FIG. 207 is a side view showing how the sections in FIG. 206 are stuck to the skin such that the skin tag projects into the thread at the back edge of the aperture.

FIG. 208 is a side view showing how the screw on its way though the thread in FIG. 207 presses the skin tag against the flexible band in the rear edge of the aperture such that the base is occluded; and how the section in FIG. 205 is stuck on top of the brick-shaped section when the screw reaches its optimal position.

Figure 209:
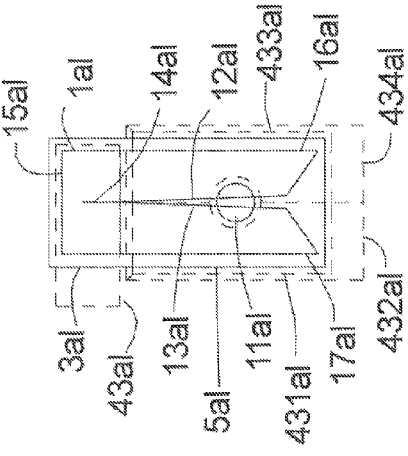

FIG. 209 is a perspective view of a section shaped like a U-shaped clip with inwardly directed inner, split legs which are located on a thin band with an adhesive lower side and an aperture.

Figure 210:
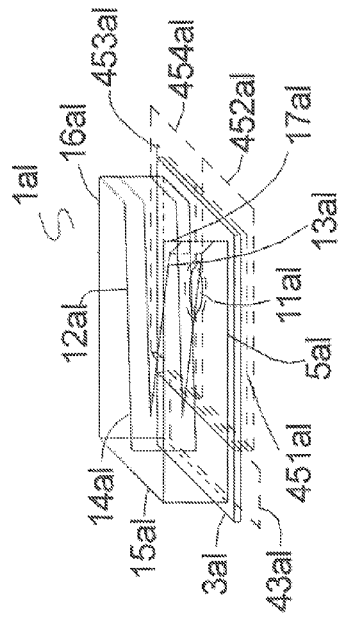

FIG. 210 is a perspective view illustrating the section in FIG. 209 where the outer legs of the U-shaped clip are squeezed together.

Figure 211:
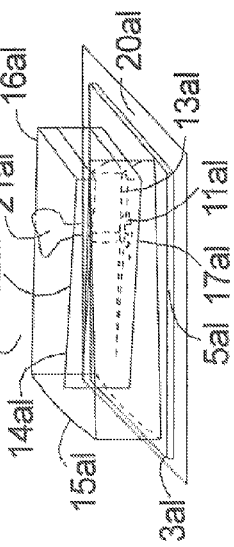

FIG. 211 is an overview of the U-shaped clip in FIG. 209.

Figure 212:
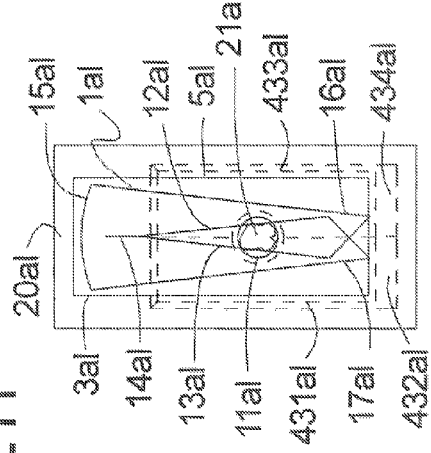

FIG. 212 is a perspective view of the squeezed clip shown in FIG. 210.

Figure 213:
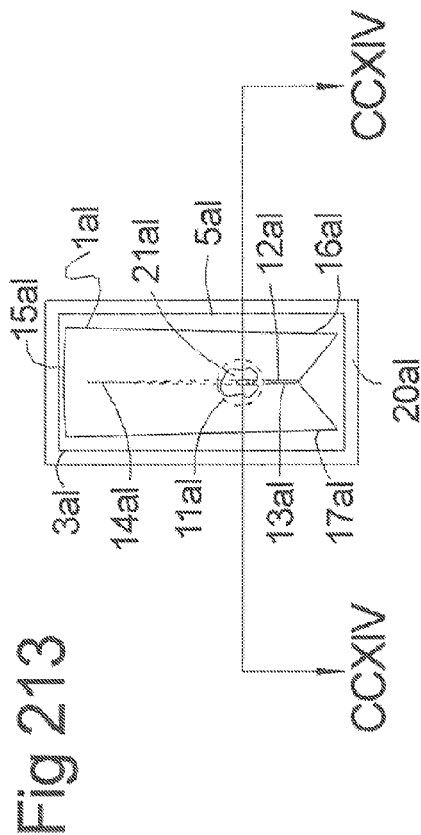

FIG. 213 is an overview illustrating how the aperture in the squeezed together section in FIG. 212 is pulled over the skin tag, how the section is stuck on the skin, and how the legs spring back such that the skin tag is occluded between the inner legs.

Figure 214:
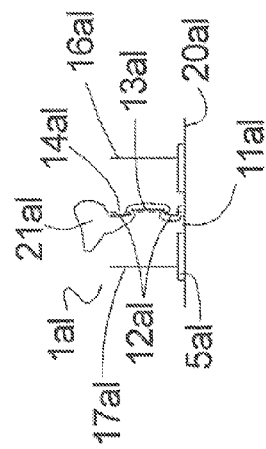

FIG. 214 is a cross section along the line CCXIV-CCXIV illustrating how the skin tag is occluded between the inner legs.

Figure 215:
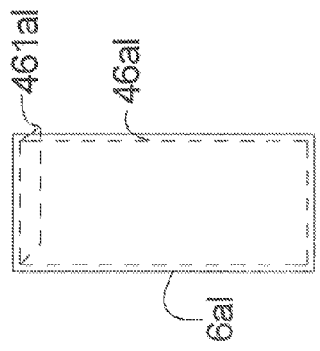

FIG. 215 is an overview of a band-shaped device with an adhesive underside.

Figure 216:
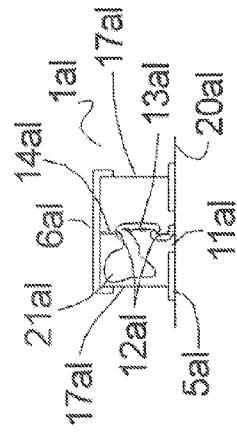

FIG. 216 illustrates how the section in FIG. 215 is applied on top of the clip in the section shown in FIG. 214, stabilising the clip and concealing the occluded skin tag.

Figure 217:
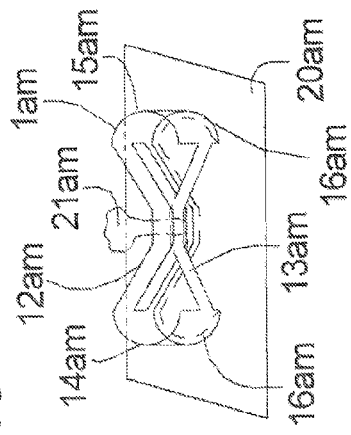

FIG. 217 is a perspective view of a device in the form of a double elastic clip with an adhesive bottom edge.

Figure 218:
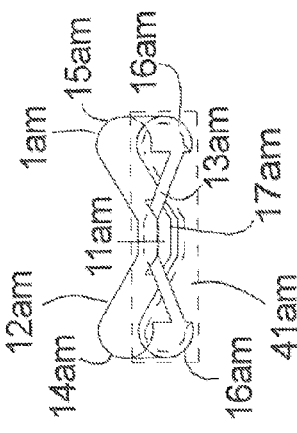

FIG. 218 is a perspective view of the section in FIG. 217 where the two elastic sides are clamped together.

Figure 219:
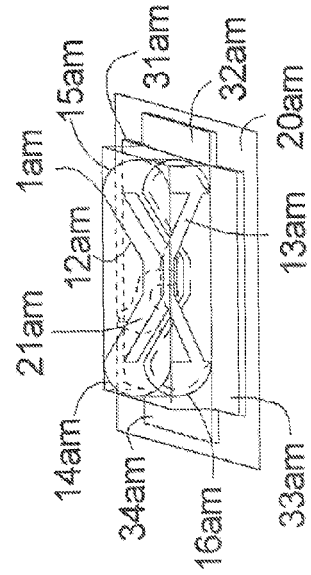

FIG. 219 is a perspective view of the section in FIG. 218 where the squeezed together clip is pulled over the skin tag and stuck to the skin.

Figure 220:
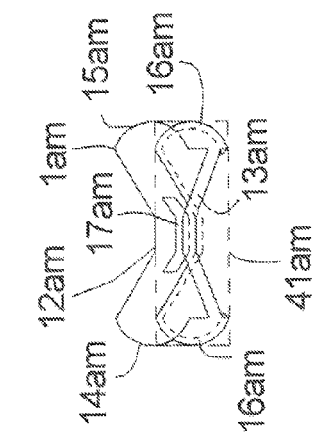

FIG. 220 is an overview of a band-shaped thin section with an adhesive underside.

Figure 221:
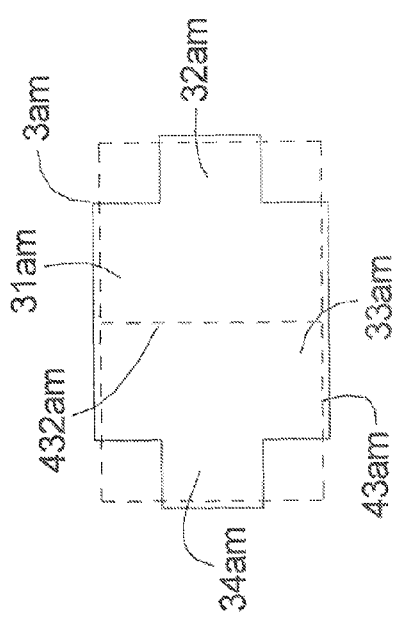

FIG. 221 is a perspective view where the adhesive section in FIG. 220 is stuck on top of the occluding section in FIG. 219, and the surrounding skin area.

Figure 222:
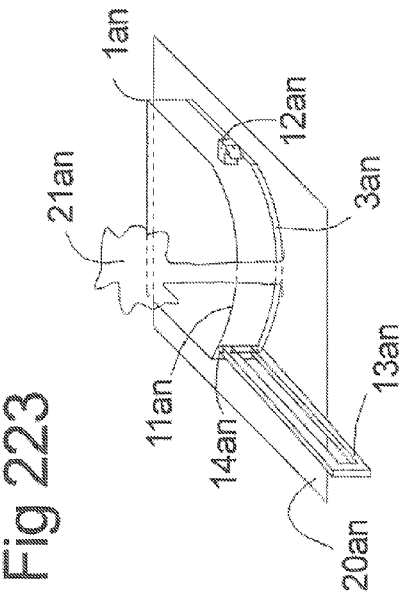

FIG. 222 is a perspective view of a section with a movable elastic strap and an adhesive underside.

Figure 223:
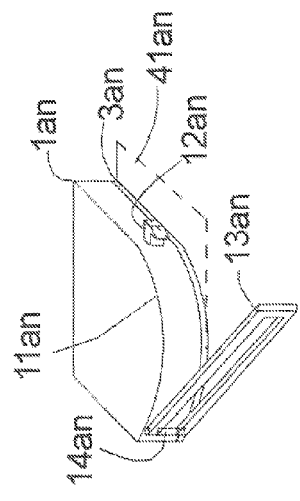

FIG. 223 is a perspective view of the section shown in FIG. 222 which is stuck to the skin against the base of the skin tag.

Figure 224:
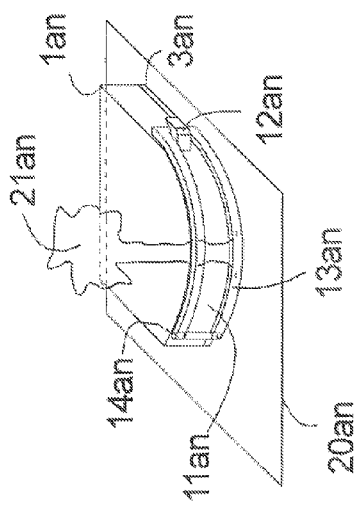

FIG. 224 is a perspective view illustrating how the strap is pulled around the base of the skin tag in FIG. 223.

Figure 225:
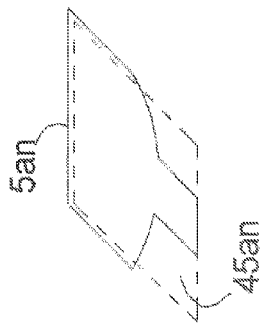

FIG. 225 is a perspective view of a thin, shaped section with an adhesive underside.

Figure 226:
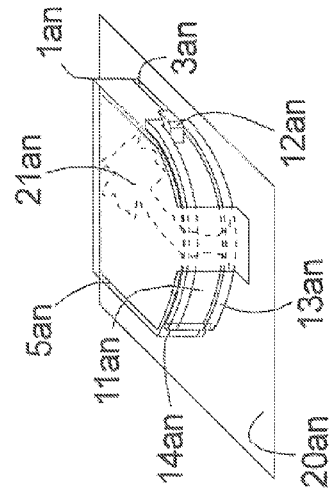

FIG. 226 is a perspective view illustrating how the section in FIG. 225 is stuck on top of the section in FIG. 224 such that the occluded skin tag is concealed and stabilised on the skin.

Figure 227:
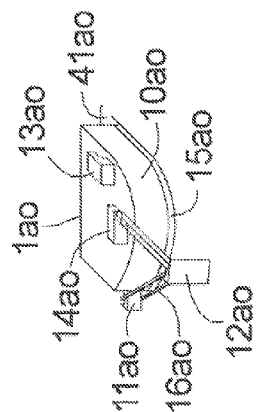

FIG. 227 is a side view of a section with an adhesive underside, where a strap extends from one side to an arm located on the upper side of the section.

Figure 228:
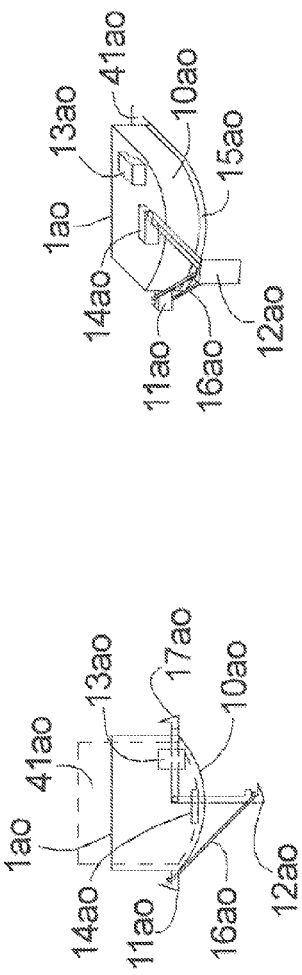

FIG. 228 is an overview of the section in FIG. 227 showing the range of movement of the arm and the two locks in the extreme positions of the arm.

Figure 229:
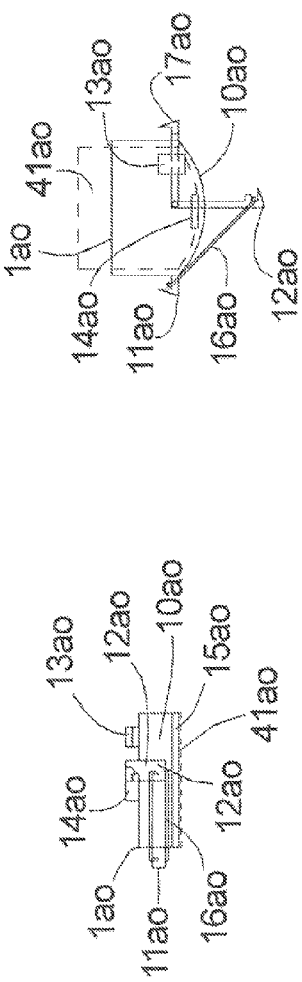

FIG. 229 is a perspective view of FIGS. 227 and 228 showing the size of the arm's handle.

Figure 230:
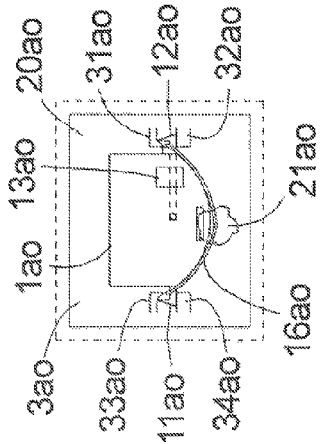

FIG. 230 is a perspective view showing how the skin tag is folded into the space between the circular edges, the arm and strap as shown in FIG. 229 and how the section is then stuck to the skin.

Figure 231:
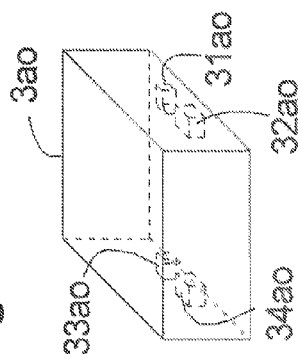

FIG. 231 is a perspective view of a section in the form of a little box with two small, specially formed heels on two of the opposing sides just above the open underside.

Figure 232:
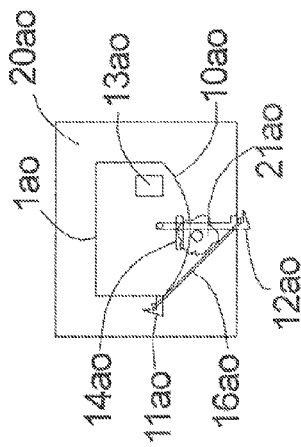

FIG. 232 is an overview of FIG. 230 where the arm has been moved to stretch the strap occluding the base of the skin tag, and where the section in FIG. 231 then is pulled over the occluded skin tag until the locking heel locks the two sections to each other.

Figure 233:
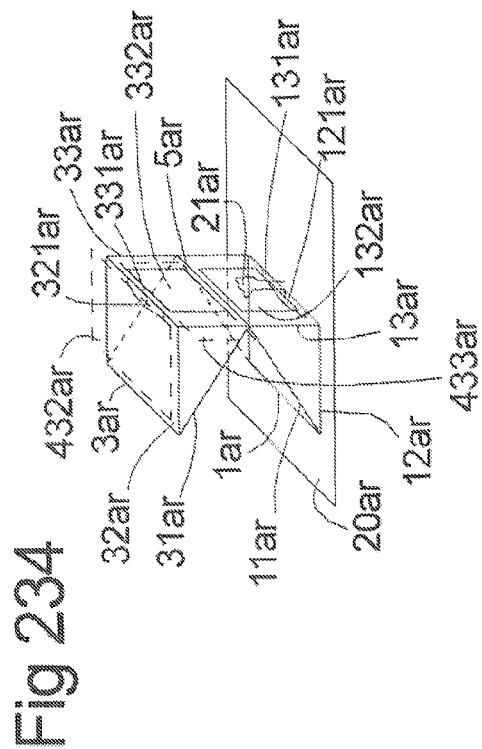

FIG. 233 is a perspective view of two connected, triangle-shaped sections each having an inverted aperture on the same side and on the opposite side.

Figure 234:
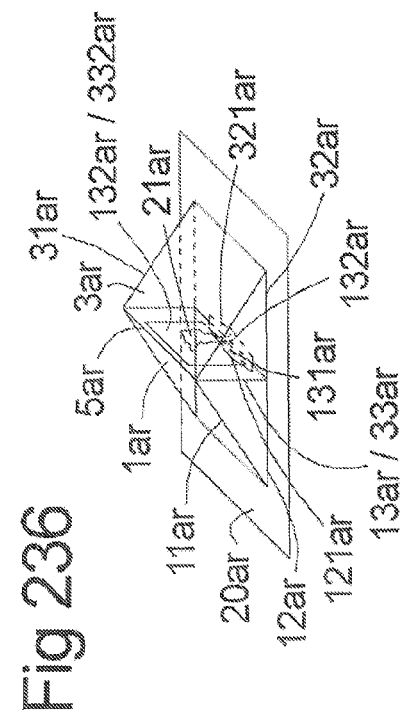

FIG. 234 is a perspective view where one of the sections in FIG. 233 is stuck to the skin tag on the skin.

Figure 235:
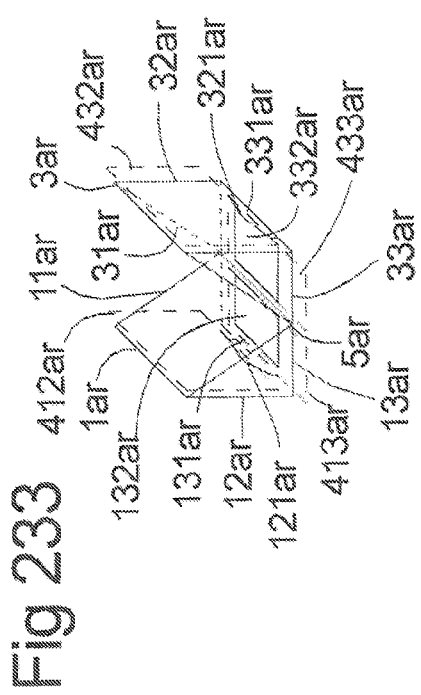

FIG. 235 is a perspective view where the other section in FIG. 234 has been rotated 90 degrees.

Figure 236:
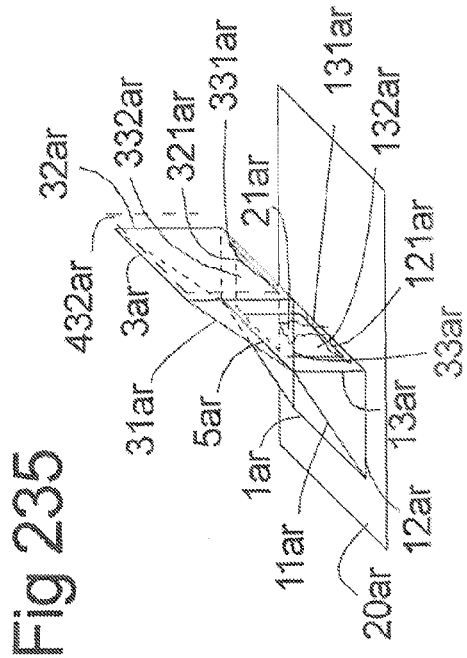

FIG. 236 is a perspective view where the other section in FIG. 235 has been rotated 180 degrees and stuck to both the skin surface and in the first section such that the skin is concealed and the base occluded.

Figure 237:
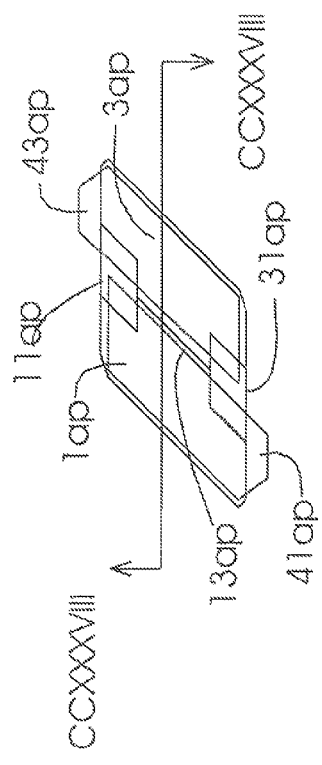

FIG. 237 is a perspective view of the section showing both the section and the surrounding, thin, elastic film.

Figure 238:
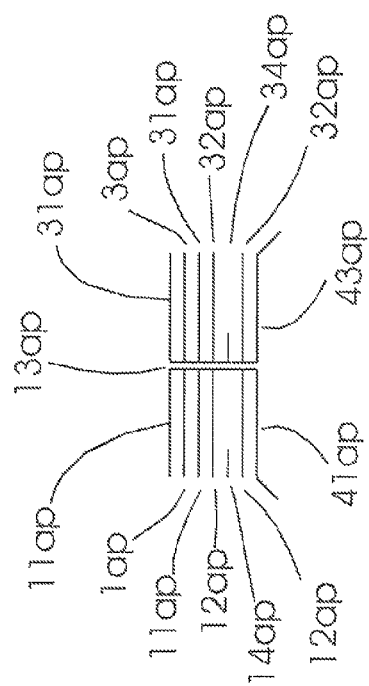

FIG. 238 is a cross section of FIG. 237 along the line CCXXVIII-CCXXXVIII in FIG. 237 and shows the central, thin slit and the different layers of the laminated device.

Figure 239:
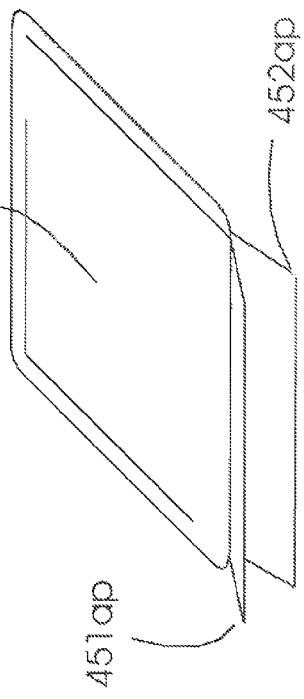

FIG. 239 is an overview of an enlarged, parallelepipedic section with an adhesive underside.

Figure 240:
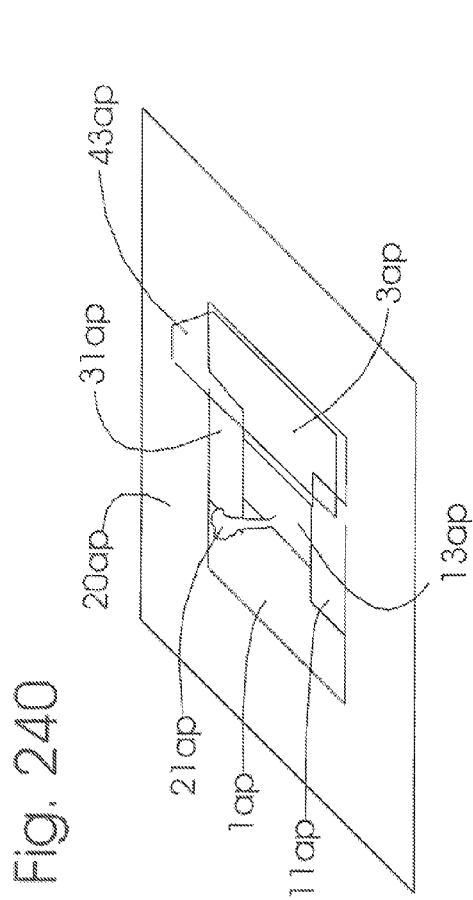

FIG. 240 is a perspective view of the device in FIG. 237 where the sections are separated and one section is stuck against the base of the skin tag.

Figure 241:
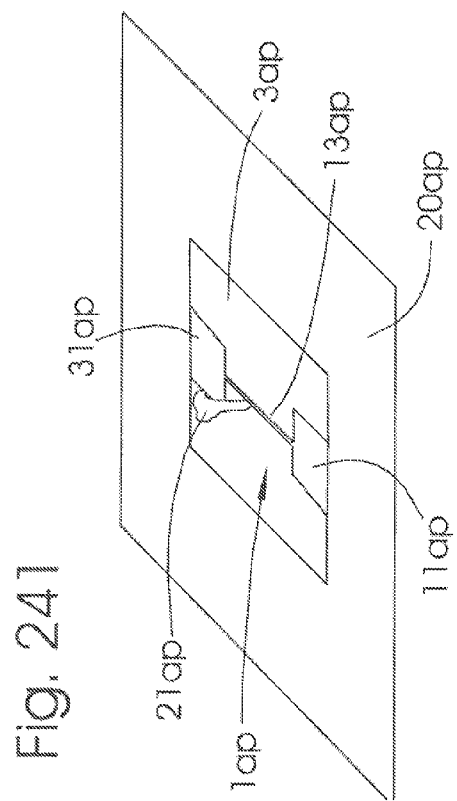

FIG. 241 is a perspective view where the other section of the device is pressed against the base of the skin tag and stuck on the skin.

Figure 242:
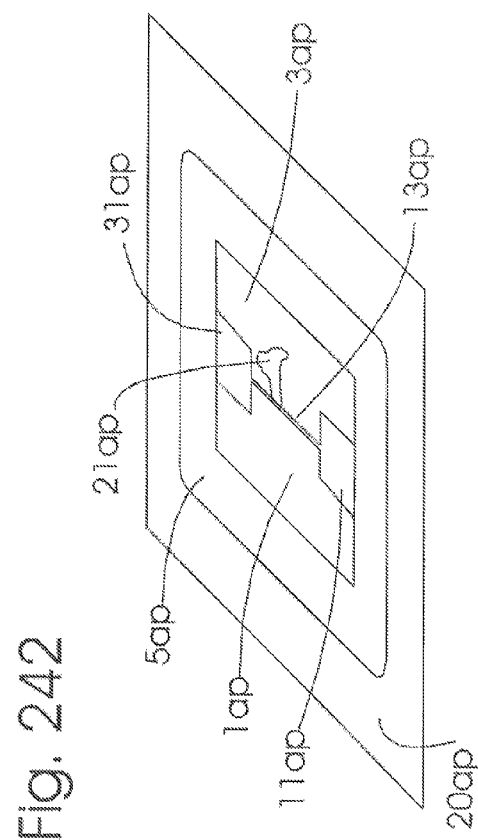

FIG. 242 is an overview showing how the protecting film in FIG. 239 is stuck on top of the device with the occluded skin tag on the skin surface.

DETAILED DESCRIPTION OF THE PREFERRED EMBODIMENTS

Skin tags or acrochordons are a commonly occurring problem in middle aged or old people of both sexes. Apart from professional treatment, folk medicine ties off the skin tag with sewing thread or rubber bands which remain on the skin tag for up to a week or until the skin tag falls off spontaneously.

The present invention provides a method for removing irritating skin tags using an adhesive, more or less flexible or elastic units. The different units form part of a little device which can be stuck or fastened to the skin with an adhesion member which surrounds or lies next to the base of the skin tag and which contains a pressure member which can provide some kind of pressure or stable mechanical influence between one to two or exceptionally up to four weeks on the fixation of the skin tag to the skin surface. The adhesion of the device to the skin surface can be more or less powerful, but a proper adhesion is necessary in areas where the skin moves a great deal, for example, the throat and axillae which also secrete more or less sweat in adults.

In the below-mentioned 41 examples, it is described how the central section of the device or adhesion member is placed on the skin and how the section or pressure member connected to the central part provides a gentle occlusion of the base of the skin tag by more than 14 different main mechanisms, at the same time as the locking member of the applied device protects the occluded skin tag from serious damage and from observation from the outside and stabilises and fixes the skin surface in a position which positively influences the final spontaneous detachment and removal from the skin.

Figure 5:
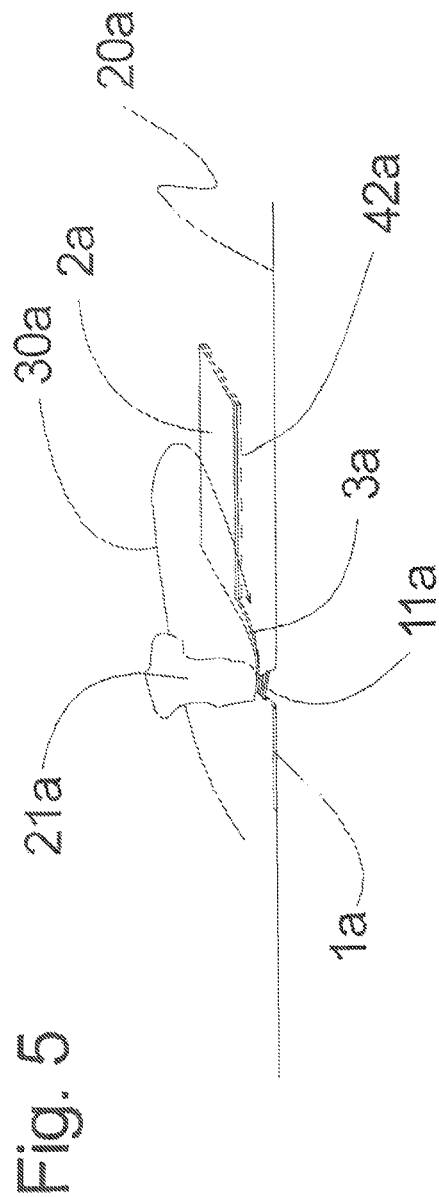
FIG. 5 is a descriptive overview of the application of the device in FIG. 3 and an occlusion of a skin tag.

In the overview FIGS. 1 and 3 in Example 1, the device consists of two thin, single-sided adhesive sections, 1 and 2, or 1a and 2 a respectively, where in the middle of the sections, there are thin thread-like sections 3 or 3a, with slits 51 and 52, or 51a and 52a respectively punched out or cut. When the protective films 41 and 42 or 41a and 42a in FIGS. 2 and 4 are removed from the adhesives surfaces, sections 1 or 1a are stuck to the skin 20 or 20a in FIG. 5, where the skin tag is then held between the thumb and the forefinger and stretched while section 2 and 2a is rotated by the other hand or is slid on the protective films, 42 or 42a, on the skin with the thumb of other hand such that the thin, thread-shaped, stretched, adhesive on one side sections 3 or 3a are wound around the base of the skin tag, 21 or 21a, according to the activity arrow 30 in FIG. 5. Because section 3 or 3a has an adhesive surface, each new turn will continually stick and lock the section either against the base of the skin tag or to one of the previous turns. The protective films 42 and 42a in FIG. 5 are then removed using removal flaps 421 or 421a so that the adhesive surfaces in sections 2 and 3 are activated. When continually stretched, the skin tag, 21 or 21a, is pushed against the skin surface with 20 or 20a, and the adhesive surfaces of section 2 or 2a, and is sealed in a horizontal position between section 2 or 2a and the skin surface 20 or 20a.

A preferred technique is when an unit, 2 or 2a, seals the skin tag, 21 or 21a, on top of section 1 or 1a. In addition to effectively concealing the skin tag, 21 or 21a, the total visible bandaged surface is reduced. Additionally, the skin tag, 21 or 21a, is easier to remove when it has withered. Because section 1 or the smaller section 1a will be stuck to the skin 20 or 20a and the unit 2 or the larger unit 2a of the device is stuck on top of the section 1 or 1a in FIG. 1 or 3, the device has been provided with corner radii 6 or 6a or 6 or 7a to prevent the corner from detaching from the skin or from the non-adhesive surface following a normal application, where the outermost surface of the device is chafed against clothes or rubbed against objects in one's surroundings.

A skin tag is usually less than 10 mm and has a diameter at the base on the skin which is less than 2 mm, which means that very little compression pressure is required to occlude the venous or the arterial blood flow in the capillary blood circulation located in the periphery. The capillary blood pressure in the outer dermal papillary is around 60 mm Hg. As a comparison it can be mentioned that with treatment of leg sores by compression in the lower leg, it is possible to calculate the compression effect using Laplace's general formula. This formula can be used to calculate the compression effect of the tag base 11 as a function of the stretch power of the unit 3 the device during rotation 30 (FIG. 5). Laplace's formula:

$$\text{Compression pressure (mmHg)} = \frac{\text{Stretch power } (Kp) \times \text{Number of layers} \times K(4630)}{\text{Skin tag's circumference (cm)} \times \text{Unit 3 width (cm)}}$$

The results of some examples are shown in the table below

| Example | Stretch Power Kp | Number of Layers | Skin tag Radius/ Circumference cm | Width unit 3 cm | Compression pressure mm Hg |
|---|---|---|---|---|---|
| 1 | 0.01 | 1 | 0.1/0.63 | 0.1 | 735 |
| 2 | 0.01 | 2 | 0.1/0.63 | 0.1 | 1470 |
| 3 | 0.01 | 3 | 0.1/0.63 | 0.1 | 2205 |
| 4 | 0.01 | 1 | 0.1/0.63 | 0.2 | 367 |
| 5 | 0.01 | 1 | 0.1/0.63 | 0.3 | 245 |
| 6 | 0.01 | 2 | 0.1/0.63 | 0.2 | 735 |
| 7 | 0.01 | 2 | 0.1/0.63 | 0.3 | 490 |
| 8 | 0.01 | 3 | 0.1/0.63 | 0.2 | 1102 |

From the table it is possible to establish that as little tangential stretch power as 0.01 Kp (10 g) can produce a full occlusion regardless of the width of unit 3 or the number of times it has been wound around the base of tag 11.

To occlude a skin tag with a radius of 1 mm, an occlusion pressure of around 60 mm Hg is required. If unit 3 has a width of 2 mm, the stretch power (F Kp) can be calculated according to Laplace's equation as:

$$F = 60 \times 0.63 \times 0.2/3 \times 4630 \quad F = 0.0005 \text{ Kp } (0.5 \text{ g})$$

However if it is preferred to occlude a skin tag with a radius twice the size, and the other parameters remain unchanged, the following is required according to Laplace's equation:

$$F = 60 \times 1.26 \times 0.2/3 \times 4630 \quad F = 0.001 \text{ Kp } (1 \text{ g})$$

Other examples of devices with one or several threads that are wound around the base of the skin tag producing an occlusion according to Laplace's formula are:

Example 11 which illustrates a band-shaped device in FIG. 70 with the four sections, 1k, 2k, 3k, and the transversal fold 31k and 5k; including threads 311k and 312k extending transversally between sections 1k and 3k, and threads 322k and 432k extending between sections 2k and 3k. FIG. 71 is a cross section of FIG. 70 showing protective films, their removal flaps and positions of the adhesive surfaces of the device. In FIG. 72, section 1k has been stuck on the skin with skin tag 21k between threads 311k and 3312k. In FIG. 73, section 3k has been bent over fold 33k together with the sections 2k and 5k and stuck together. In FIG. 74, the stuck together section 3k has been rotated over the skin tag 21k such that the adhesive threads 311k, 312k, 321k, and 322k are wound around the skin tag 21k so that the capillaries in the base are occluded. FIGS. 75 and 76 illustrate how section 33 and skin tag are placed down on the upper side of sections 1 and 2 on the surface of the skin in front of section 5 in FIG. 77; and are then folded and stuck over the occluded skin tag 21k which is fixed to the skin and concealed.

Example 35 illustrates in FIG. 197 a device where 2 loops or straps are connected to each other with knots or ties 14aq and 17aq round a central aperture 11aq in a thin, adhesive, band-shaped section 1aq. Outside the knots or ties 14aq and 17aq, the other part of the loops or straps 12aq, 126aq, and 16aq; as well as 13aq, 135aq, and 15aq run through guide channels 181aq and 182aq as well as 191aq and 192aq and are connected to sections 3aq and 5aq which are more or less bigger and more flexible than section 1aq. FIG. 198 shows the protective films and positions of the adhesive surfaces. FIG. 199 shows how section 1aq is stuck to the skin surface 20aq with skin tag 21aq in the middle of the aperture 11aq. In FIG. 200, the sections 3aq and 5aq are stretched according to the activity arrows 31aq and 51aq such that the loops or rings and knots 14aq and 17aq in section 1aq are contracted. In FIG. 201, the contraction in FIG. 200 is complete and skin tag 21aq is occluded. Additionally the stretched threads 12aq, 13aq, 15aq and 16aq have been placed on top of section 1ak before the protective films 43aq and 45aq have been removed from sections 3aq and 5aq, which have then been stuck on top of the occluded skin tag 21aq on section 1aq, on the skin surface and on top of each other to lock the loose threads, protect skin tag 21aq and by concealing the skin tag, rendering the device cosmetically pleasing.

Other examples where more or less adhesive threads are used to bind or tie together a skin tag or its base to a surface:

Example 29 shows a device in FIG. 167 with an adhesive section 12ac with the aperture 11ac under the larger lower wheel 1ac, which has an indentation 13ac at the aperture 11ac and the smaller upper wheel 3ac with a notch for the O-ring 31ac and the strap 32ac running around the O-ring 31ac. Section 5ac with the fold 51ac is adjacent to section 12ac. FIG. 168 is a longitudinal section of FIG. 167 illustrating the strap 32ac around the O-ring 31ac in notch 14ac, and the indentation 13ac in the aperture 11ac. In FIG. 169, section 12ac and the wheel 1ac have been stuck to the skin surface 20*ac* with the skin tag 21*ac* in the aperture 11*ac* at the indentation 13*ac*. The O-ring 31*ac* has been stretched over the skin tag by means of the strap 32*ac* and the fingers 22*ac* and 23*ac*. FIG. 170 is a longitudinal section of FIG. 169 where the O-ring 31*ac* on the wheel 1*ac* occludes the base of the skin tag 21*ac* which is bent in the wheel 3*ac* by notch 14*ac*. In FIG. 171 the adhesive surface of the section 5*ac* has been activated by removing the protective film 45*ac* with the removal flap 451*ac* and section 5*ac* has been bent over the fold 51*c* thus covering and protecting the occluded skin tag 21*ac* on the skin surface 20*ac*.

It is also possible to occlude the blood flow at the base of the skin tag using different types of small, fixed devices which are stuck to the skin as in Example 39 where a more or less elastic strap 13*an* has been fastened using fasteners 14*an* to a little more or less hard and massive disc-like section 1*an* with an adhesive underside 3*an* in FIG. 222. FIG. 223 shows how section 1*an* is placed immediately behind skin tag 21*an* on the skin surface 20*an*. In FIG. 224 the strap 13*an* has been drawn around skin tag 21*an*, which has been pressed against the surface 11*an* and then hooked on hook 12*an*. FIG. 225 illustrates a thin, flexible section 5*an* with an adhesive side covered by protective film 45*an*. In FIG. 226 the section 5*an* is stuck on top of section 1*an*, fixing and concealing the occluded skin tag 21*an* on the skin surface 20*an*.

According to Laplace's formula an occlusion of the capillaries in the base of a skin tag should occur using a circular applied device. A similar effect can be achieved by rotating the skin tag itself so that the connective tissue inside the base is stretched, producing an occlusion because the rotation itself lengthens the base of the skin tag which stretches the capillaries thereby reducing their lumen.

Example 5 illustrates a band-shaped device, shown in a longitudinal section in FIG. 31, where the underside has three sections 1*e*, 2*e* and 3*e* with a common upper side 5*e* laminated with a more rigid material than the more or less flexible, elastic, adhesive material mentioned previously. These sections can be activated at different points in time by removing the protective films, 41*e*, 42*e* and 43*e* using removal flaps 411*e*, 421*e* and 431*e*. In FIG. 32, sections 2*e* and 3*e* have been bent over section 1*e* which has been stuck to the skin 20*e* right next to the base of the skin tag 21*e*. FIG. 33 shows how the protective film 43 has been removed and the skin tag 21*e* has been stuck to the surface of the section 3*e*. In FIG. 34, section 3*e* has been bent over the other side of skin tag 21*e*. FIG. 35 shows how skin tag 21*e* is sealed in one of the folds created in section 3*e*. In FIG. 36 the adhesive surface 4*e* has been activated by removing the protective film 44*e* using the removal flap 441*e*, and the fold 3*e* shown in FIG. 35 is bent down and sticks the adhesive surface 4*e* to the upper side of the section 1*e* stuck to the skin surface 20*e*. Thereby, the rigid laminated side 5*e* creates a pointed fold which occludes the base of the skin tag 21*e*.

Figure 38:
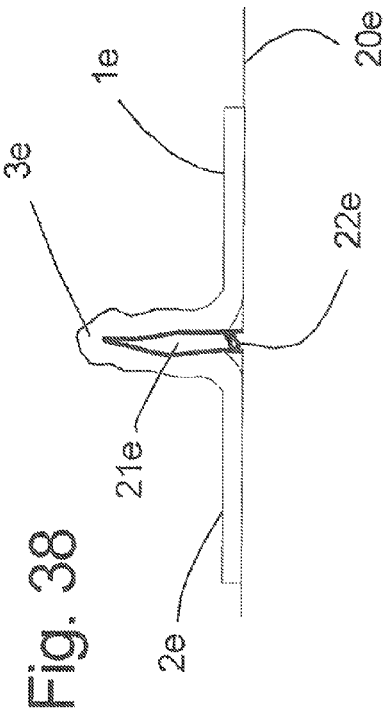
FIG. 38 is a longitudinal section which shows how the skin tag in FIG. 37 is stuck to the skin in rotated state.
Figure 37:
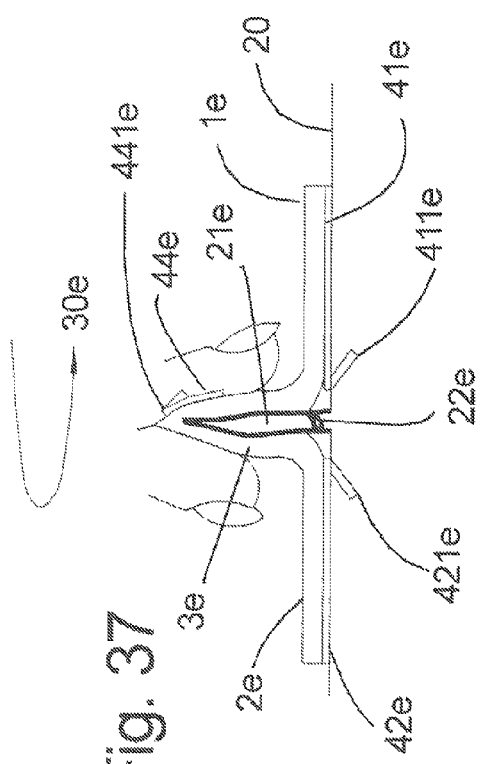
FIG. 37 is a longitudinal section which shows a different application of the device in FIG. 32, where the device is not stuck to the skin but rather forms a crease around the skin tag which is then rotated.
Figure 39:
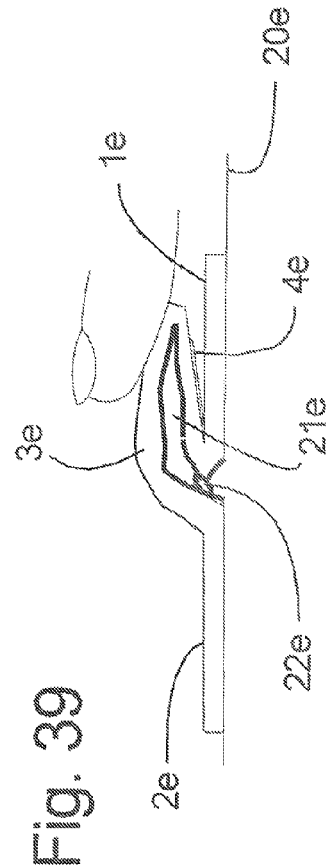
FIG. 39 is a longitudinal section of FIG. 38 which shows how the rotated skin tag in the crease is moreover folded down parallel to the skin surface in order to increase the occluding effect.

FIG. 37 is a variant of the application of the device previously described in Example 5. In Example 6 FIG. 37 the protective film 43*e* has been removed in FIG. 31 and skin tag 21*e* has been sealed in a fold in section 3*e* which is described in FIGS. 32, 33 and 34 without the protective film 41*e* being removed. Because the section has not been stuck to the skin surface, the sealed skin tag 21*e* could be rotated such that a rotation occlusion 22*e* occurs at the base. FIG. 38 illustrates how the base of the skin tag 21*e* in the fold 3*e* is rotated and occluded 22*e* as well as how sections 1*e* and 2*e* are stuck to the skin surface 20*e*. FIG. 39 shows how the adhesive surface 44*e* is activated and how the fold 3*e* is pushed down and stuck to the upper side of the section 1*e* and how the laminated fold reinforces the rotation occlusion 22*e*.

In Example 9 a very flexible occlusion of the base of the skin tag is produced by the band-shaped, more or less rigid device in FIG. 57, which consists of sections 1*h* and 3*h* where the outside of the more or less rolled outer edges 11*h* and 13*h* and the upper sides are adhesive, while section 2*h* has an adhesive underside and a transversally extending fold 22*h*. In FIG. 58A the protective film 41*h* has been removed and the rolled edge 11*h* has been placed against the base of the skin tag 21*h*. FIG. 58B shows how the protective film 42*h* has been removed and how section 2*h* is bent over fold 22*h* such that the rolled edge 31*h* in section 3*h* abuts the skin tag 21*h* and its base. In FIG. 59, the protective film 43*h* has been removed and the rolled edge 31*h* has been stuck to the skin tag 21*h*; section 2*h* has been pushed down such that, upon being rolled, the rolled edges 11*h* and 31*h* stretch and occlude the base of the skin tag 21*h*. Following continuous pressure on section 22*h* in FIG. 60, sections 1*h* and 3*h* are fixed to the skin and section 2*h* seals skin tag 21*h* to section 3*h*.

Example 13 is a variant of the circular occlusion according to Laplace, where an hourglass-shaped device 1*n* in FIG. 83 has two more or less adhesive sections 12*n* and 13*n* between which an oval aperture 11*n* is placed which creates two threads adhesive on one side, which kept sections 1*h* and 2*h* together. In FIG. 85, the aperture 11*h* has been pulled over the skin tag 21*h* on the skin surface 20*n* and the hourglass-shaped sections 12*n* and 13*n* are in the process of being rolled from diametrically opposite directions. FIG. 86 shows how sections 12*n* and 13*n* are rolled around themselves by fingers 22*n* and 23*n* which causes the base of the skin tag to rotate while at the same time the more or less adhesive threads on both sides of the aperture 11*n* are twisted around the base of the skin tag, 21*n*. FIG. 87 shows how the band-shaped section 2*n* which is adhesive on one side is stuck on top of the base of the skin tag 21*n*, occluded by rotation, such that sections 12*n* and 13*n* are locked to the skin surface, simultaneously concealing and fixing the skin tag 21*n*.

Example 30 illustrates additional tests with a circular occlusion where the cross-shaped section 1*af* in FIG. 172 has four fixed, arms 12*af*, 13*af*, 14*af* and 15*af* adhesive on the underside and two movable adhesive arms, 16*af* and 17*af*, which are placed above arms 15*af* and 12*af*. The six similar-sized arms are located around a central part, in the middle of which there is a minute aperture 11*af*. FIG. 173 shows how the device 1*af* is placed on the skin 20*af* against the skin tag 21*af*. FIG. 174 shows how the protective film 4*af* is removed using the removal flap 41*af* and how arms 12*af* and 15*af* and half of the central part of the device 1*af* are stuck on the skin surface 20*af* and how by pulling in arms 13*af* and 14*af* the free aperture 11*af* can be stretched and forced over the skin tag 21*af*. In FIG. 175, arms 13*af* and 14*af* are no longer drawn in; and the usually minute central aperture 11*af* has contracted again occluding the base of the skin tag 21*af*. The rest of the central part of the device 1*af* and arms 13*af* and 14*af* have been stuck to the skin 20*af*.

Another more or less hard, massive section is shown in Example 36 where the occlusion of the skin tag occurs in between two radii of different size between the screw and the screw-thread which creates a half-moon shaped occlusion. The device consists of an internally threaded block 1*ak* in FIG. 203 with an adhesive underside 14*ak* and an aperture 11*ak* located below the screw-thread; as well as a screw 3*ak*, described in FIG. 202, with its thread head 32*ak* and, relative to the thread, movable tip 31*ak*. FIG. 204 is a cross section of FIG. 203 and shows the flexible band 15*ak* located at the back edge of the aperture 1*ak*. FIG. 206 shows how the screw 3*ak* is screwed in the section 1*ak*. In FIG. 207, the section 1*ak* has been stuck to the skin 20*ak* with skin tag 21*ak* sticking into the internal thread 13*ak* near the band 15*ak* in the back wall of aperture 1*ak*. FIG. 208 shows how the screw 3*ak* is screwed into the thread 13*ak* in section 1*ak* until the movable tip 31*ak* presses the base of the skin tag 1*ak* against the flexible band 15*ak* and occludes the blood flow. In order to lock the screw in an occlusive position and at the same time hide the skin tag 21*ak* on the skin surface 20*ak*, the band-shaped section 5*ak* in FIG. 205 with an adhesive underside has been stuck on top of section 1*ak* and the head 32*ak* of the screw 3*ak*.

Example 38 uses another occlusion principle where the clip 1*am* in FIG. 217 has two resilient sides 14*am* and 15*am* and a narrow leg 13*am* and a broad leg 12*am* with a aperture 17*am* as well as a folded underside with an adhesive surface. In FIG. 218 the resilient sides 14*am* and 15*am* have been pressed together such that the leg, 13*am*, is pushed into the aperture, 17*am*, creating a new vertical aperture, 11*am*, on the other side. In FIG. 219 the skin tag 21*am* has been pulled through the in aperture 11*am* created in FIG. 218 and the clip 1*am* has been stuck to the skin 20*am* before leg 13*am* springs back and occludes the base of the skin tag 21*am*. FIG. 221*am* shows how the flap-like section 3*am* with an adhesive side in FIG. 220 has been stuck on top of the occluded skin tag in FIG. 219 and onto the skin surface in order to protect and hide the skin tag, preventing unintentional stresses on the fixation of the clip 1*am*.

Example 14 uses the inherent elasticity of a little tube where a little transversal cut which has been cut through the outer convex part of the tube can be opened, and when closed occludes the base of the skin tag. FIG. 88 shows a slice of a little tube with two openings 12*p* and 13*p* and a peripheral, transversal cut 11*p* and an adhesive inside and an adhesive surface 15*p* on the outside. FIG. 89 shows how the tube is bent together so that the cut expands. In FIG. 90 the expanded aperture 11*p* has been pulled over skin tag 21*p* on the skin surface 20*p*. In FIG. 91 some of the surface 15*p* has been stuck to the skin locking the aperture 11*p* in a contracted position. FIG. 92*a* illustrates how the tube is pushed together with a finger from above which partly sticks the inside of the tube together and partly sticks the tube to the skin surface with surface 15*p*. In FIG. 92*b*, section 1*p* is no longer contracted and the occluded skin tag 21*p* has been fixed inside the tube 1*p* to the skin surface 20*p*.

In Example 24 the occlusive effect of a spiral is used where the base is squeezed between two spiral twists and the rest of the skin tag is protected within the spiral. FIG. 142 shows a spiral 1*ä*, which is covered on both sides with the band-shaped sections 3*s* and 5*s*; and which through a straightened fold, 31*ä* or 51*ä* protrudes out of the spiral 1*ä*. FIG. 144 is a side view of 142, showing the design of the spiral, the fold and position of the adhesive surfaces on the protruding sections 3*ä* and 5*ä*. FIG. 145 is a side view where the protruding sections 3*ä* and 5*ä* are clamped together so that the spiral 1*ä* is opened on the side that is pulled over the skin tag 21*ä* on the skin surface 20*ä*. In FIG. 146, the spiral 1*ä* has sprung back; occluding skin tag 21*ä*, and section 52*ä* has been bent over fold 51*ä* and stuck to 5*ä*. The protective film 451*ä* has been removed with the removal flap 4521*ä* and the spiral has been wound around the base of skin tag 21*ä* and stuck on the skin 20*ä*. Section 32*ä* is then stuck to section 3*ä* using the fold 31*ä*. Finally, section 6*ä* is stuck over the section on the skin concealing and further fixing skin tag 21 to the skin surface 20*ä*.

By occluding the blood flow to the small base of the skin tag, a tying-off effect can be achieved which results in the spontaneous detachment of the skin tag from the skin surface proximal to the occlusion. The occlusion can be produced by ligation or compression of the skin tag or by twisting and/or bending a skin tag and fixing it so that it cannot go back to its natural state.

EXAMPLES

The following examples are provided as further illustrations of the preferred embodiments of the invention.

Example 1

In this example, an adhesive thread is tied around the base of the skin tag occluding the blood flow.

FIG. 1 is an overview illustrating an embodiment of the invention which consists of a device made of a thin, small strip of textile material, hydrocolloid or polymer or the like, with a single adhesive side. The device is made up of two similar-sized sections 1 and 2 which through two cuts 51 and 52 through both textile material or the like and the adhesive side of the device create a narrow connecting section 3. This has a side that is adhesive and another side that is not adhesive. The rounded corners 6 and 7 in FIG. 1 hinder rolling up and detachment from the skin during the time the device in place so that the skin tag can be twisted off. Radii 81 and 82 in FIG. 1 serve to absorb the pulling force from the application and the occlusive phase so that the narrow connection 3 does not become detached from sections 1 and 2.

From FIG. 2 which is a longitudinal section according to line II-II of FIG. 1, it appears that the adhesive surfaces of sections 1 and 2 are each covered by protective films 41 and 42 which inactivate or prevent these surfaces from sticking to the skin of human beings or animals. In order to more easily activate the adhesive properties, an edge of the covering films 41 and 42 has been turned up creating a little flap 411 and 421 through which covering films 41 and 42 can easily be drawn off from the adhesive sections 1 and 2.

FIG. 3 is an overview showing a variant of the invention in FIG. 1 where sections 1*a* with the protective film 41*a* and the removal flap 411*a* are smaller than section 5*a* with the protective film 42*a* and removal flap 421*a* and where the middle sections 1*a* and 5*a* connecting section 3*a* are much longer in Example 1 because the cuts 51*a* and 52*a* are not symmetrical. The size of the radii 6*a*, 7*a*, 81*a* and 82*a* depend upon the size of the sections and the magnitude and direction of the shearing force, pulling and rolling-up power that sections 1*a* and 2*a* are exposed to.

FIG. 4 is a longitudinal section along the line IV-IV in FIG. 3 and shows the positions of the sections 1*a* and 2*a* separated by the cuts 51*a* and 52*a* from the narrow section 3*a* as well as protective films 41*a* and 42*a* each with their removal flaps 411*a* and 421*a*.

FIG. 5 shows how the device according to FIGS. 1-2 and 3-4 is applied to achieve a satisfactory occlusion of the skin tag and is shown here for simplicity purely as a detailed description of the application of the device according to FIGS. 3 and 4. Upon application, the covering film 41*a* is first removed from the adhesive side of the smaller part 1*a* of the device. The covering film 41*a* is torn off using the flap 411*a* in FIG. 4 which is shown as a longitudinal section according to IV-IV in FIG. 3. It is now possible to separate the small part 1*a* from the connection 3*a* and fix the small part 1*a* to the skin right near the skin tag 21*a*. The skin tag 21*a* is then grabbed between the thumb and forefinger of one hand and lightly pulled away from the skin surface so that the base of skin tag is stretched right out. The larger part 2*a* of the device is held in the other hand and lightly pulled so that the connection 3*a* between the little part 1*a* fixed to the skin and the part 2*a* in the hand is stretched. The larger part of the device 2a is then wound around the base of the skin tag 21a which is still held in the other hand. This facilitates slipping the larger part 2a over the covering film 42a round the skin tag 31a with the stretched connection 3a and rotating it three times around the skin tag according to the activity arrow 30a. The adhesive part of 3a then sticks to the base of the skin tag 21a after the first rotation and through its stretched elasticity occludes the blood flow in the distal parts of the tag. With continued rotation around the skin tag according to the activity arrow 30a, the adhesive surface of 3a will stick to earlier rotations of 3a, creating a ring 11a, where each rotation continually seals earlier and current rotations of 3a which means that the adhesive laminated ring 11a reinforces the effect of the occlusion with every rotation, despite low and variable stretching in 3a during the rotating application according to 30a.

Figure 6:
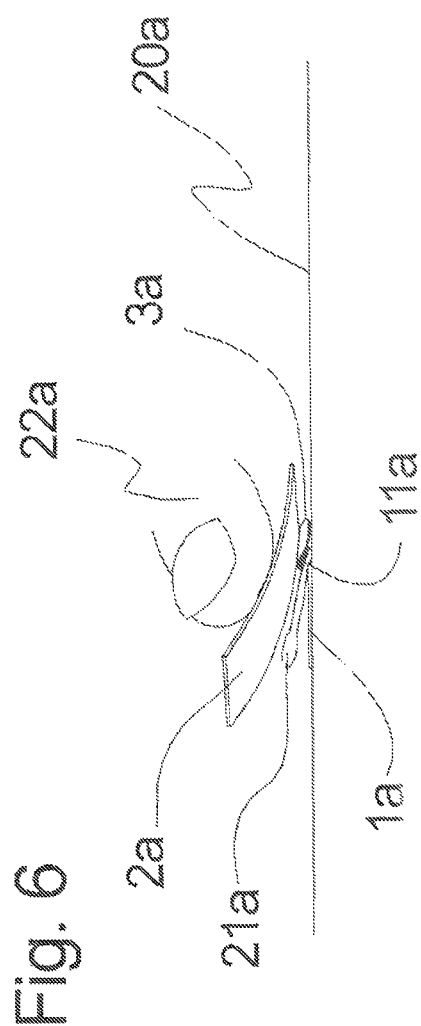
FIG. 6 illustrates how the occluded skin tag 5 is concealed under another part of the device.

FIG. 6 shows that the covering film 42a is removed from the adhesive section 2 of the device and how the larger section 2a is stuck to the small section 1a using a finger 22a. The occluded skin tag 21a is then fixed by the adhesive surface of the larger section on top of the non-sticking surface of the small section 1a of the device in a position parallel to the skin surface. The larger section 2a of the device will be completely covered by the small section 1a, concealing skin tag 20a and giving the applied device a cosmetically pleasing appearance.

Example 2

In this example the skin tag is rotated and folded onto the skin surface to create a satisfactory occlusion.

Figure 7:
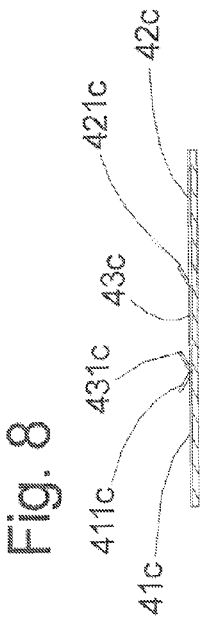
FIG. 7 is an overview of another embodiment of the invention, with three different surfaces on the same side of the device, which can be activated independently of each other.

FIG. 7 shows another embodiment of the invention where a band-shaped device consisting of a skin adhesive material, such as latex, elastic fabric, polyurethane film or another polymer material, gels, foams, or hydrocolloids or other solid or semi-solid materials known to a person skilled in the art. The band-shaped device in FIG. 7 is divided into 3 different areas 1c, 2c and 3c. A fold 33c is made right in the middle of the area 3c in FIG. 7, which is perpendicular across the band and easily can be angled into two similar-sized legs.

Figure 8:
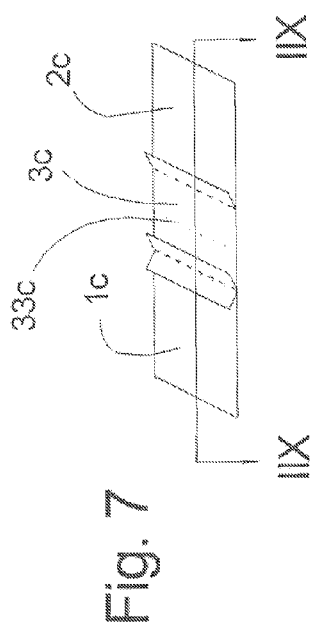
FIG. 8 is a cross section of the device along the line IIX-IIX in FIG. 7.

FIG. 8 is a longitudinal section along the line llX-llX in FIG. 7 where the adhesive surfaces of the three areas are covered by protective films 41c, 42c and 43c with respective removal flap 411c, 421c and 431c.

Figure 9:
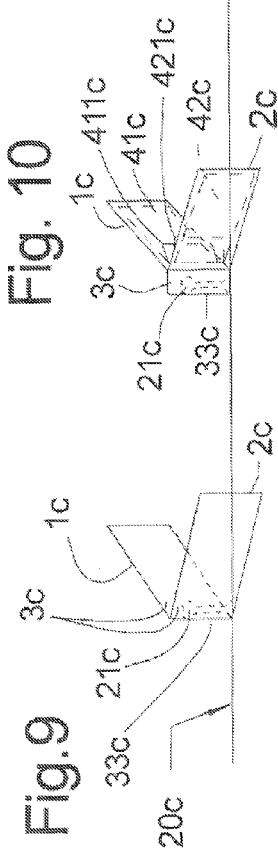
FIG. 9 is an overview of how a skin tag is gripped in the middle of the device.

FIG. 9 reveals how the protective film 43a with removal flap 431c has been removed prior to the application of the device, and the device has been angled in fold 33c on the skin 20c by the skin tag 21c.

Figure 10:
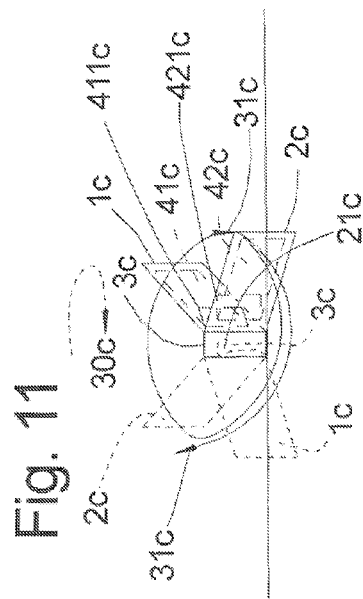
FIG. 10 shows how a skin tag is glued and sealed in the adhesive middle zone of the band-shaped device in FIG. 7.

FIG. 10. The angled device in FIG. 9 has been immediately placed behind the skin tag 21c, which, if necessary, can be held stretched up between the thumb and forefinger of one hand. Using the other hand, the device is held between the thumb and forefinger on both sides of the fold 33c on the non-adhesive outer surface of the legs. The skin tag is pressed down and completely fixed and enclosed between the two adhesive surfaces in area 3c.

Figure 11:
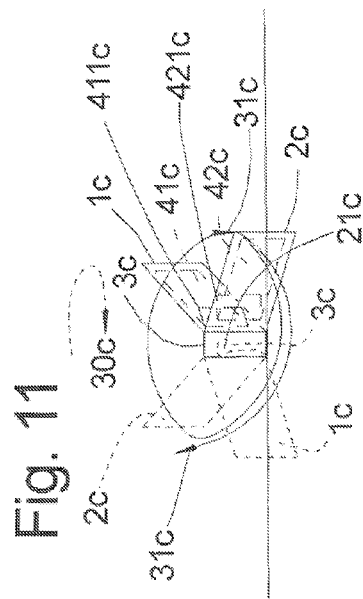
FIG. 11 illustrates how a skin tag is rotated in order to achieve a degenerative occlusion of the blood flow in the proximal part of the tag.

FIG. 11 shows how the sealed skin tag 21c in area 3c is rotated 180 degrees according to activity arrow 30c, which is shown in the FIG. in broken lines. If the skin tag is large, the occlusion can be increased by a full rotation with open legs as per activity arrow 31c. After this occluding rotation the protective films 41c and 42c are removed from the adhesive surfaces of areas 1c and 2c, using the removal flaps 411c and 421c, while the legs still are free.

Figure 12:
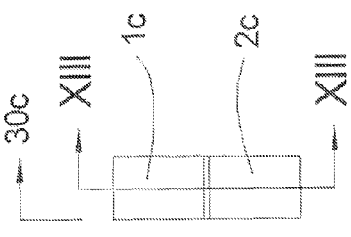
FIG. 12 is an overview which shows how the rotationally occluded skin tag is turned so that it is parallel to the skin surface and stuck to the skin surface.

FIG. 12 shows how the device with the skin tag, which has been rotated one turn, has now been bent down on the skin surface 90 degrees according to activity arrow 30c, where the adhesive surfaces in areas 1c and 2c fix the occluded skin tag to the skin surface.

Figure 13:
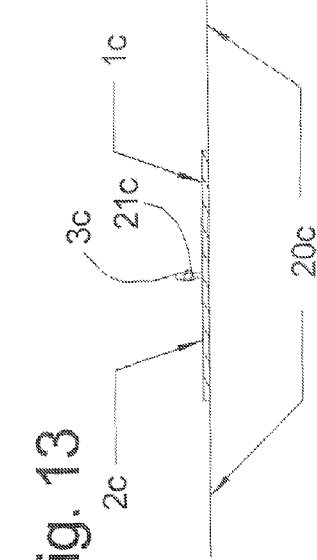
FIG. 13 is a longitudinal section along the line XIII-XIII in FIG. 12 and illustrates an occluded skin tag which is fastened to the skin surface.

In FIG. 13, which is a longitudinal section along the line Xlll-Xlll in FIG. 12, it can be seen that the rotation-occluded skin tag 21 in a fold in area 3c is firmly fixed parallel to the skin surface 20c by areas 1c and 2c. When the device is removed after a full occlusion, the skin tag sealed to the device is detached from the skin without pain, bleeding or scarring.

Example 3

In a third embodiment of the invention, the adhesive surfaces are located on alternating sides of the thin, band-shaped device consisting of non-woven, hydrocolloid or other such textile, where the skin tag is occluded by twisting it towards the skin surface.

FIG. 14 shows the two sections 1d and 2d of the device and the removal flaps 411d and 421d extending up from the surface of the band.

FIG. 15 is a cross section along the line XV-XV in FIG. 14 showing how the adhesive sides of sections 1d and 2d of the band-shaped device are covered by protective films 41d and 42d with respective removal flaps 411d and 421d.

In FIG. 16, the device has been bent alongside the two removal flaps 411d and 412d, such that sections 1d and 2d form two legs which are slightly angled in relation to each other with their long sides towards the skin 20d. The protective film 41d has been removed from the adhesive side of the section 1d of the device. Skin tag 21d has been stretched between the thumb and the forefinger of one hand, after which the adhesive surface of part 1d extends in such a manner that the skin tag 21 can be stuck to the middle of the adhesive surface of part 1d.

FIG. 17 illustrates how it is possible, using the thumb and the forefinger of one hand, to press the non-adhesive side of part 1d round the skin tag 21d such that it is sealed in a fold 3d, after which the adhesive surface of part 1d is reduced. The sealed skin tag 3d is rotated vertically 180 to 360 degrees according to the activity arrow 30d.

FIG. 18 illustrates how the remaining adhesive side of section 1d is stuck to the skin fixing the rotation-occluded skin tag 21d parallel to the skin surface in a fold 3d in the band-shaped device.

FIG. 19 shows how the surface of section 2d is first activated by removal of the protective film 42d with removal flap 421d according to FIG. 17. The activated surface of section 2d has then been folded over the non-adhesive surface of part 1d fixing the skin tag 21d sealed in fold 3d securely to the skin surface 20d.

FIG. 20 is a cross section according to line XX-XX in FIG. 19 showing how the skin tag 21d sealed in fold 3d is securely fixed to the skin surface 20d and then covered by two layers of the device, rendering the skin tag invisible; and securely removed by the device from the skin surface following a sufficiently long occlusion.

Example 4

The band-shaped device has transversal slits allowing the device to fold over, facilitating the occlusion and fixing of the skin tag to the skin surface.

Figure 21:
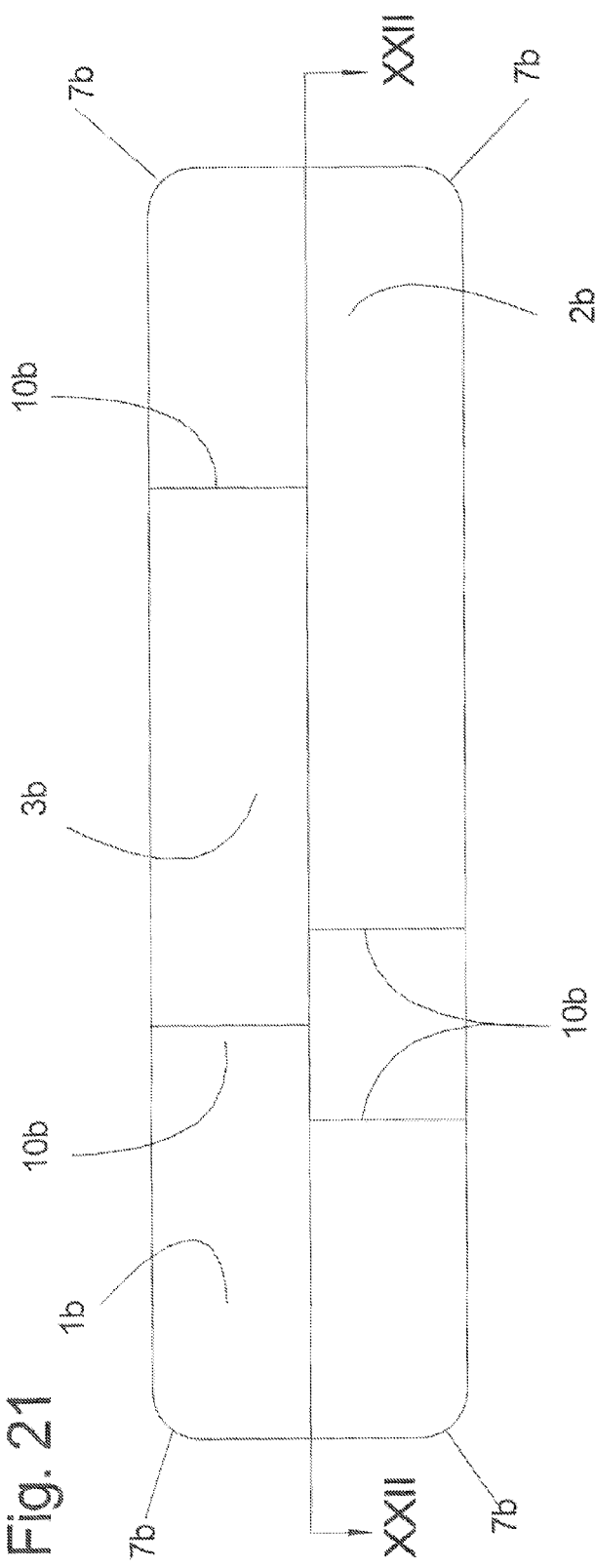
FIG. 21 is an overview of a fourth embodiment of the invention with transversal slits.

FIG. 21 shows a fourth embodiment of the invention, where a narrow band of adhesive material, such as for example a hydrocolloid which is a material known to a person skilled in the art, through semi-transversal slits 10b has been divided into three sections 1b, 2b and 3b, where 3b where 3b is the central part. To increase adhesion to the skin surface and reduce the risk of detachment, the corners of the band have been rounded by a radius 7b.

Figure 22:
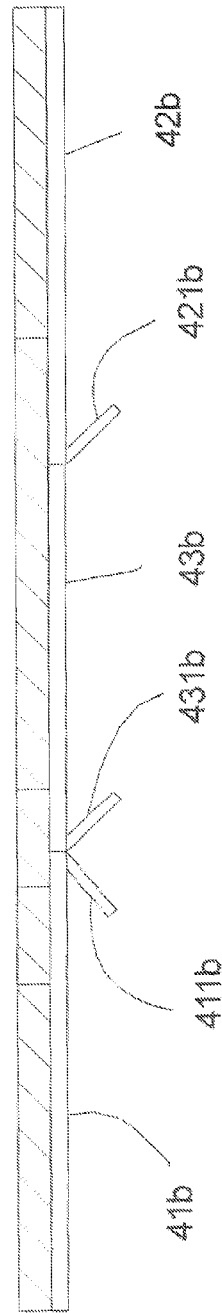
FIG. 22 is a longitudinal section of the device taken at XII-XII in FIG. 21.

FIG. 22 is a longitudinal section along XXII-XXII in FIG. 21, and shows how the adhesive surfaces of the three sections 1b, 2b and 3b are covered with protective films 41b, 42b and 43b, making it possible to separately remove the protective film and activate the respective adhesive surfaces at different points in time using flaps 411b, 421b, and 431b. The protective films 41b and 43b extend over the slits 10b, which increases the rigidity and maneuverability of sections 1b, 2b, and 3b upon application of the device.

Figure 23:
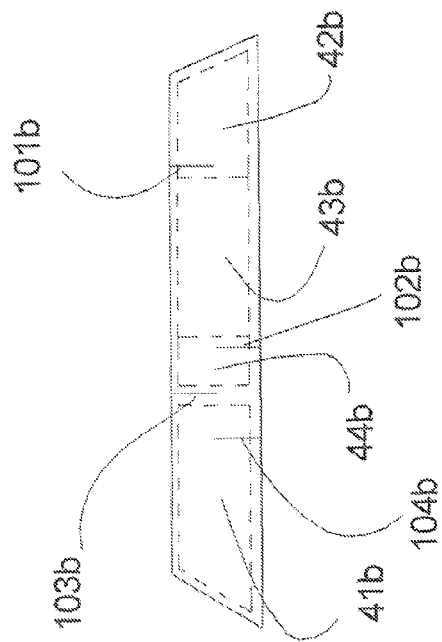
FIG. 23 illustrates the device in perspective according to FIG. 21, with covering strips or protective films, which stabilize the slits in the band-shaped device according to the invention.

FIG. 23 is a perspective view of FIG. 21 where cuts 101b, 102b, 103b and 104b have been cut transversally halfway through the device in four different places.

Figure 24:
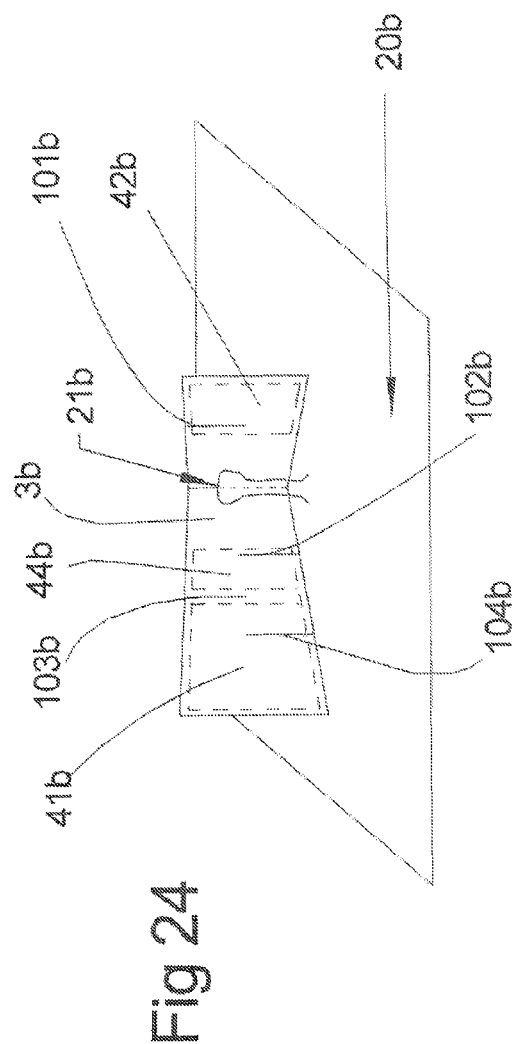
FIG. 24 illustrates how the skin tag is fixed to an activated adhesive section of the device.

FIG. 24 shows a device which is ready for use to remove a skin tag where the protective film 43b has been removed and the adhesive surface of the central part 3b of the device has been exposed and the device has been angled and placed upright behind skin tag 21b.

Figure 25:
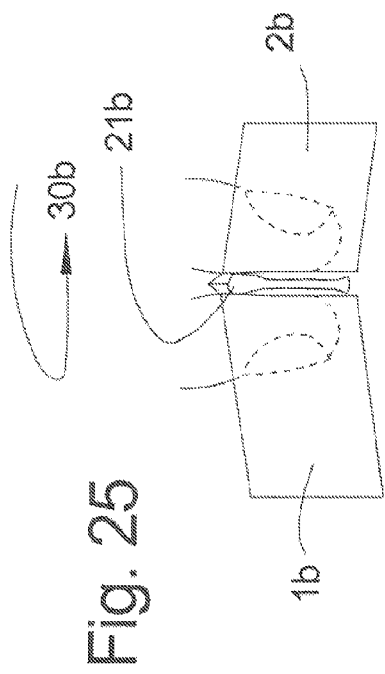
FIG. 25 illustrates how the skin tag is sealed using the device and occluded by rotation.

FIG. 25. The skin tag is held slightly stretched between the thumb and finger of one hand, while the device is positioned with the other hand, such that the edge of the long side lies against the skin surface; the adhesive surface is then pushed against the vertically positioned skin tag 21b so that it sticks to the middle of the adhesive surface of 3b. The skin tag 21b is then pinched on both sides from behind such that the it is completely surrounded by one of the sealed folds created by the adhesive surfaces in section 3b. In the upright position, the sealed skin tag 21b is rotated 180 to 360 degrees according to the activity arrow 30b.

Figure 26:
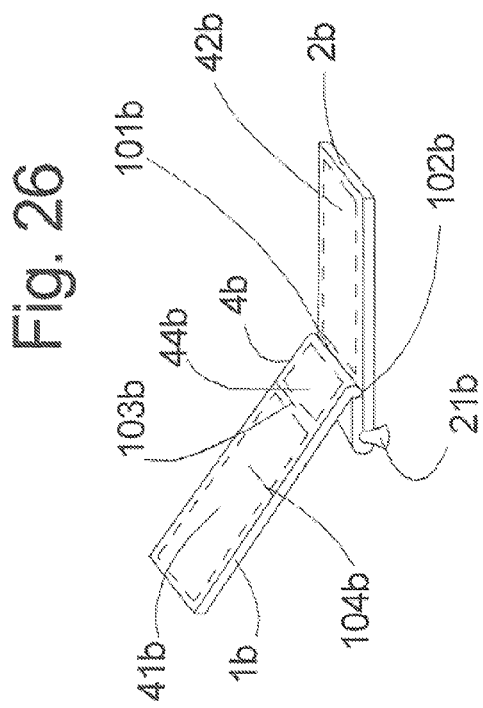
FIG. 26 illustrates how the device is prepared for fixing the occluded skin tag on the skin.

FIG. 26 shows how the sealed and rotated skin tag is placed against the skin surface with the adhesive sections 1b, 4b and 2b covered by protective films upwards. Protective films 42b and 44b are removed, thus activating the adhesive surface of part 2b and part 4b.

Figure 27:
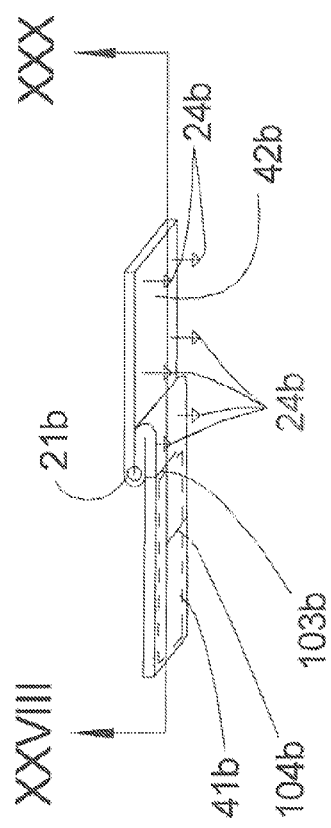
FIG. 27 illustrates how part of the device with the sealed and rotation occluded skin tag is fixed to the skin.

FIG. 27 shows how the device in FIG. 26 has been turned 180 degrees over the long side, and sections 2b and 4b have been stuck to the skin according to arrows 24b, where the sealed top of the skin tag 21b is marked with a little radius.

FIG. 28 is a cross section of FIG. 27 along the line XXVIII-XXX, where the section 1b of the device has been tilted so that it is positioned vertically in slits 103b in FIG. 27.

In FIG. 29, the protective film 41b in FIG. 28 has been removed, and section 1b of the device has been rotated 180 degrees round a line between the central borders of slits 104b and 103b, which stick the base to section 1b between slits 104b and 103b. As a consequence, the adhesive side of section 1b of the device is turned towards the non-adhesive surface of the section 2b of the device.

In FIG. 30, section 1b of the device has been stuck on top of section 2b, which is then covered by section 1b, whereby the applied device fixes the skin tag 21b to the skin surface 20b in a rotated and occlusive position. The skin tag is no longer visible from the outside, and the applied device simply appears as a bandage to an observer. The device shown in FIG. 30 can be easily removed by pulling it from the skin 3-7 days later after the occlusion; the skin tag 21b sealed in the device comes away with the device. Because the occlusion entails the degeneration of nerves and other tissue in the surrounding area, the skin tag can be removed without pain or bleeding. It has also been shown that the removal of a skin tag via occlusion does not lead to scarring.

Example 5

In a fifth embodiment of the device, an occlusion can be achieved via a device induced sharp fold which prevents the blood flow to the skin tag.

FIG. 31 shows a longitudinal section of the band-shaped, laminated device according to the invention, where a thin, more or less more rigid, yet flexible unit is combined with a more or less elastic, adhesive layer. The adhesive underside of the device is divided by three sections 1e, 2e and 3e with protective films 41e, 42e and 43e which have removal flaps 411e, 421e and 431e. A narrow, transversally extending, adhesive surface 4 is on the upper side of the device, which is covered by a protective film 44e with a removal flap 441e.

FIG. 32 shows how the protective film 41e is removed from the adhesive surface of section 1e of the device using the removal flap 411e, after which section 1e is stuck to the skin 20e as near the skin tag 21e as possible. The protective film 43e is then removed by means of the removal flap 431e so that the adhesive surface 3e of the device is exposed.

FIG. 33 shows how, using a finger, skin tag 21e can be bent and stuck to the adhesive surface of section 3e. Section 2e of the device is then bent backwards so that skin tag 21e is caught in a fold in the adhesive surface of part 3e, shown in FIG. 34. The skin tag 21e is sealed in the fold by exerting a heavy pressure from two directions with the thumb and forefinger as shown in FIG. 35.

FIG. 35 shows how, after removal of the protective film 42e using the removal flap 421e (see FIG. 34), the adhesive section 2e of the device is exposed and stuck to the skin 20e. The skin tag 21e is now enclosed in a vertical fold which is extending transversally over the band-shaped device which is fixed to the skin 20.

In FIG. 36, the adhesive surface 4e has been activated by removal of protective film 44e using removal flap 441e, and the transversal flap 3e with the adhesive surface 4e is folded down and sticks to the non-adhesive surface of section 1e. As a result, a sharp fold 23e has, through the laminate, been created along the base of the stuck together flap 3e, which nips the lowest part of the skin tag and occludes the blood flow. After an acceptable period of time, the applied device can easily be removed from the skin; the occluded and sealed skin tag in fold 3e comes off too without pain or other discomfort.

Example 6

This Example is a variant of Example 5 where rotation and folds can be combined to enhance the occlusion.

The sealed skin tag can be rotated in fold 3e in the direction shown by arrow 30e in FIG. 37, if it is nipped with the fingers while protective films 41e and 42e are in place and protective film 43e is removed from the adhesive surface of section 3e of the device in FIG. 31.

In FIG. 38, the flaps 421 and 411 have been used to remove the protective films 42e and 43e such that the sections 1e and 2e and skin tag 21e with the rotated base 22e can be stuck to the skin 20e.

FIG. 39. If the device consists of an adhesive surface 4e on the backside of section 3e, as shown in FIG. 37, the rotated skin tag can be folded down over the non-adhesive surface of section 1e, enhancing the occlusion. Regardless of whether sealed skin tag 21e, as shown in FIG. 36, is only rotated, or rotated and folded as shown in FIG. 39, the thin blood vessels in the base of the skin tag will be occluded, which means that it can degenerate within a few days. The occluded skin tag can then be easily removed from the skin surface together with the device without difficulty.

Example 7

Another embodiment of the invention consists of a band-shaped device of a more or less rigid material where one side has adhesive properties. The device is divided into sections 1f, 2f, 3f, 5f and 6f which are defined by a pre-made fold such that the different sections can be bent and moved in relation to each other.

In FIG. 40, section 1f of the device has a protective film 41f protruding from the underside of the section instead of a removal flap. The border to section 2f consists of two imprinted folds 11f and 12f on either side of a punched-out flap 211f which extends into section 2f. Sections 2f, 3f and 5f have a common protective film 43f which also projects from the underside of the section. Between sections 2f and 3f there is an imprinted, curved fold 31f, likewise between sections 3f and 5f. The curved fold between section 6f and 5f is divided into two halves 61f and 62f by the flap 511f extending into section 6f in 5f. Under 61f there is a projecting protective film 46f on top of the adhesive surface.

Upon application of the device, sections 2f, 3f, 5f and 6f are folded over the imprinted folds 11f and 12f which are shown 41. The protective film 41f is then removed to activate the adhesive surface of section 1f, after which one should first put the punched-out flap 211f as near the base of the skin tag 21f as possible before section 1f is stuck to the skin surface. During this manoeuvre, the protective film 43f stabilises handling of sections 2f, 5f and 5f and prevents unnecessary bending of the imprinted curved folds 31f.

In FIG. 42, the protective film 43f has been removed and the flap 511f projecting from section 6f is pushed at an angle upwards directly towards the base of the skin tag 21f. The curved fold 31f can then be activated so that the sections 2f, 3f and 5f can be folded in relation to each other, as shown in FIG. 42.

Finally the protective film 46f is removed and section 6f is stuck to the skin surface with flap 511 as near the skin tag 21f as possible as shown in FIG. 43. By carefully tipping one of the curved folds 31f to one side, it is possible to stick the top of the skin tag 21f to underside of section 3f and bend it to one side. If the sections of 3f, lying above sections 5f and 2f just in front of fold 31f, are pressed downwards, flaps 211f and 511f will slide towards each other and occlude the base of the skin tag.

FIG. 44 is a longitudinal section of FIG. 43 in perspective, where section 3f has been pressed so far down that 2f and 5f have been stuck to adhesive underside of 3f, completely sealing skin tag 21f in the double fold, which in turn is stuck to the skin by sections 1f and 6f. Given that the skin tag is sealed between two adhesive surfaces and that the base is occluded, it will come away with the device without difficulty when the device is removed from the skin surface after a few days.

Example 8

The section in FIG. 45 is made up of a thin, more or less rigid and elastic band of polymer or natural material, with five sections each of which having an adhesive surface and which because of an imprinted fold between sections can be moved in relation to each other. The combined length of the sections 1g and 2g of the device is as long as section 6g and the total length of 1g, 2g and 6g is as long as sections 3g and 5g.

FIG. 45 is an overview of the sections 1g, 2g, 3g, 5g and 6g of the device, where section 1g has a protective film 41g on the upper side and a little projection 12g on the short side of the section. Section 6g has a notch on the short side of the device and a protective film 46g on the upper side. On the lower side of section 2g there is a protective film 42g, on section 3g there is a protective film 43g, and on section 5g, a protective film 45g.

As in Example 7, the protective films project from one side of the sections, which facilitates removal when the adhesive surface is to be activated.

FIG. 46 is a longitudinal section of FIG. 45 along the lines XLVI-XLVI illustrating how protective film 41g has been removed from section 1g which is stuck to the skin surface with notch 12g located in direct contact with the base of the skin tag 21g.

FIG. 47 is a longitudinal section of FIG. 46; where the protective films 42g, 43g and 45g have been removed, activating the adhesive surfaces of sections 2g, 3g, 5g. Using the still inactivated section 5g, the entire device is bent over the skin tag 21g.

FIG. 48 is a longitudinal section of FIG. 47 illustrating how the notch in section 6g is now placed against the base of the skin tag 21g such that an enclosed, ring-shaped structure is created encircling the skin tag. By manipulating the sections before or after the ring has been created, skin tag 21g is stuck to one of the adhesive surfaces 1g, 2g or 3g inside the ring.

FIG. 49 shows how using pressure on section 3g, skin tag 21g is enclosed and sealed in a fold created by 1g, 2g and 3g. Protective film 46g is then removed, and section 6 is pressed down against the skin and sticks to it. Given that sections 1g, 2g and 6g altogether are as long as 3g and 5g, the volume of the enclosed skin tag will produce an eccentric effect when section 6 is stuck to the skin, enhancing the occlusion of skin tag 21g.

FIG. 50 shows that, while section 6g is being stuck to the skin, section 5g is stuck to the non-adhesive side of section 6g, which encloses and seals off the ring-shaped device, while at the same time enclosing and permanently sealing skin tag 21g to the device. The permanently enclosing of skin tag 21g ensures that the skin tag comes away too when the device is removed from the skin a few days after the occlusion.

Example 9

Another embodiment of the eccentric principle in Examples 7 and 8 is described in FIGS. 51-60. A controllable occlusion of the blood flow to the skin tag can be achieved with a simple hard or rigid device.

FIG. 51 is a perspective view of the device made up of three sections 1h, 2h and 3h with two pre-prepared, elastic, curved folds between the three sections, thereby connecting them to each other via the folds. Sections 1h and 3h each have a projecting protective film 41h and 43h on their upwardly directed adhesive surfaces. These two sections combined are as long as 2h, which has its adhesive surface with a projecting protective film 42h on its underside.

In FIG. 52, the protective films 41h on sections 1h and 42 of section 2h have been removed, sections 2h and 3h have been bent upwards and 1h has been stuck to the skin as near the base of the skin tag as possible. The protective film 43h is now removed, exposing the adhesive surface of section 3h. This section is then moved, as shown by the arrows 30h and 31, against the base of the skin tag, and the curved fold between sections 2h and 3h is then pressed down towards the skin. By doing this, the curved fold between 1h and 2h will expand to compensate for the compressed volume of the skin tag while the elasticity in the curved fold between 2h and 3h presses the edge of section 3h abutting the base of the skin tag harder against the base, thus enhancing the occlusion.

FIG. 53 shows how the skin tag is bent down, clamped and sealed by the adhesive surface of section 2h against the surfaces of sections 1h and 3h which are stuck to the skin surface.

FIG. 54 is a perspective view showing another embodiment of the invention, where the device is made up of three sections 1h, 2h and 3h. Section 1h has an asymmetrical edge with a small indentation 12h with which to grip the base of the skin tag 21h. On the upper side, there is a protective film 41h on the adhesive surface, and on the lower side or in the middle of the section, there is a thin, hard film 11h, covering most of the surface, leaving a 1-5 mm narrow, elastic edge 13h around 1h. Section 2h is symmetrical with a protective film 42h on the underside. On the top side of the section 3h there is a protective film 34h and on the underside a thin, hard film 31h, which leaves a small, elastic edge 32h round 3h, where the free short side 32h of the device also is asymmetrical.

In FIG. 55, the protective film 41h has been removed and the indentation 12h of section 1h has been placed directly against the base of skin tag 21h. Sections 2h and 3h have been bent upwards, protective films 42h and 43 have been removed and 3h has been rotated in the direction of the arrow 30, until the asymmetrical edge 32h touches the base of skin tag 21h. In this example the volume of 21h has been taken up by the more or less rigid section 2h, while the elastic edge 32h has been pressed against the base of skin tag 21h which is located in the indentation, with a careful angling because of the asymmetry. This makes it possible to control the compression pressure on the base of 21h and as a consequence, control the occlusion of the blood flow.

FIG. 56 shows how the adhesive surface of 2h pushes down and fixes skin tag 21h against the hard films 11h and 31h, which are connected to the skin surface on the backside by sections 1h and 2h.

FIG. 57 reveals a device consisting of three parts 1h, 2h and 3h, where the total length of 1h and 3h is longer than 2h. This is compensated for by zone 22h which is more elastic than the rest of section 2h. Section 1h has adhesive top side with a protective film 41h which extends over a semi-circular strip 11h which can be stuck or fixed to the upper or under side of the section 1h and which has a convex adhesive surface. The strip 11h can also be made of 1h itself or of section 1h with the addition of films, foils, strips, foams, gels, or fibres of polymer or natural materials. Section 2h has an adhesive underside covered by protective film 42h. Right in the middle of 2h there is a zone 22h which is more elastic than the rest of section 2h. Like 1h, section 3h has adhesive top side, a semi-spherical strip 31h of polymer or natural material, with an adhesive convex surface covered by protective film 43h.

In FIG. 58A, the device is held vertically and the protective film 41 is removed from the section 1h and the strip 11h is placed with its elastic side against the skin tag 21h. The perspective FIG. 58 B shows how sections 2h and 3h have been bent so that the device, through the elastic, curved fold 22h, takes form of an open ring around skin tag 21h. By doing this, protective film 43h is removed, and the strip 31h is placed touching the base of skin tag 21h.

FIG. 59 shows how, by pressing both parts of section 2h downwards against the skin surface 20h as shown by the arrows 23h and 24h in FIG. 58 B, the two strips 11h and 31h stick to each other and to the lower end of the skin tag; the elastic influence on zone 22h means that the pressure against the base of skin tag 21h will not be too great. The semi-spherical strips 11h and 31h are simultaneously pressed against each other and turned at the same time as being stuck, which lifts and stretches the base of the skin tag, rendering the area of the occlusion larger and making it more effective.

FIG. 60 shows how the occluded skin tag 21h has been stretched, stuck and fixed to the adhesive surface of section 2h against surfaces 1h and 3h, which in turn are stuck to skin surface 20h. Through the application manoeuvre in FIGS. 58B and 59, the elastic zone 22h is now stretched to its fullest; section 2h is stuck to the surfaces of 1h and 3h thus securing a long lasting occlusion of the base of skin tag 21h.

Example 10

By rotating each of the discs with their adhesive surfaces in relation to each other, a device for the occlusion of skin tag 21i on the skin surface can be formed.

FIG. 61 is an overview of a disc which has been divided into 3 sections 1i, 2i and 3i each with their protective films 41i, 42i and 43i on the adhesive underside of the disc. At one edge of section 3i there is a small radius 31i which has been punched out of the disc.

FIG. 62 describes another more or less larger disc than that shown in FIG. 61, where the adhesive top side has been divided by protective films 45i, 46i and 47i in sections 5i, 6i and 7i. At one edge of section 6i, a small radius 61 has been punched out of the disc.

In FIG. 63, the smaller and more or less larger discs have been connected by pulling up slit 31i through slit 61e, after which protective films 43i and 46i have been removed, and the adhesive surface 3i on the underside has been stuck to the surface 6i which is adhesive on the upper side to a new non-adhesive section 8i.

FIG. 64 is a cross section of FIG. 63 along the line LXIV-LXIV and shows how two new semi-circular discs have been fused, where disc 1i+5i is asymmetrical because area 5i is greater than 1i. Likewise, disc 7i+2i is asymmetrical because area 7i is greater than area 2i. The two discs are connected through surface 8i.

FIG. 65 shows how by punching out the area in common, in 8i; all materials have been removed other except two narrow sections 83i and 84i. Some material from the long sides of are 8i have been retained in a narrow edge 815i which connects the two semi-circles 1i and 5i and edge 827i which connects semi-circles 2i and 7i. Centrally in the two edges, a little bit extra material has been punched out in order to create an aperture 81i in disc 1i+5i and another similar-sized aperture 82i in disc 2i+7i.

In FIG. 66, protective films 41i and 45i have been removed and disc 1i+5i has been opened along the narrow edge 815i.

In FIG. 67, disc 1i+5i in FIG. 67 has been folded completely up so that the aperture 81i is opened. Skin tag 21i has been pulled through aperture 81i in disc 1i+5i, which has then been stuck to the skin surface.

In FIG. 68, Disc 2i+7i is folded out with the protective films 42i and 47i facing the disc 1i+5i located against the skin 20i, and the skin tag 21i has been pulled through the narrow sections 83i and 84i and through aperture 82i. Disc 2i+7i is then rotated in the direction indicated by the arrow 30i; as a result, both narrow sections 83i and 84i wind themselves around skin tag 21i.

FIG. 69 shows how sections 83i and 84i occlude the base of the skin tag and how protective films 42i and 47i are removed from the disc 2i+7i which is then stuck to the top side of the more or less smaller disc 1i+5i and to the skin surface 20i.

Example 11

In this embodiment of the invention, the thin, band-shaped device is first folded so that narrow, adhesive, elastic sections are created which are then rotated around the base of the skin tag.

FIG. 70 is a perspective view of a band-shaped device which consists of four connected sections 1k, 2k and 3k which all have an adhesive surface on the same side while section 5k has an adhesive surface on the top side. Sections 1k and 2k each have an adhesive protective film 41k and 42k on the underside which can be removed using the removal flaps 411k and 421k. The section 5k of the device is larger than sections 1k and 2k combined and has a protective film 45k on the top side with removal flap 451k. Between sections 2k and 5k, there is an imprinted, curved fold 51k which enables sections 2k and 5k to move in a controlled fashion in relation to each other. Section 3k does not consist of a homogenous single surface, on the contrary it has been divided into a central part 31k and 32k, between which is an imprinted, curved fold 33k extending transversally over the band-shaped device. Between sections 1k and 31k there are two diagonally asymmetrically extending narrow bands 311k and 312k, extending from the outer edges of section 31k to the central part of section 1k, made of the same material as the device, or of another polymer or natural material. Between sections 3k and 2k are similar asymmetrical narrow bands extending diagonally from the edges of section 32k to the central part of section 2k, made of the same material as the device, or of another polymer or natural material. To stabilise and keep the structure together, protective films 431k and 432k with removal flaps 4311k and 4321k are located on the underside of section 3k.

FIG. 71 is a cross section of FIG. 70 along the line LXXl-LXXl and shows the two opposing removal flaps 4311k and 4312k which stabilise the imprinted, curved fold 33k between the adhesive surfaces of sections 31k and 32k. The adhesive surface with protective film 45k of section 5k lies on the top side of the band-shaped device while the other adhesive surfaces on the other sections are located on the underside of the device and are covered by protective films 41k, 431k, 432k and 42k.

In FIG. 72, sections 5k, 2k, 321k, 322k, 32k, 31k and sections 311k and 312k have been rotated 180 degrees over section 1k. The protective film 41k has then been removed using removal flap 411k and section 1k has been stuck on the skin 20k as near skin tag 21k as possible.

FIG. 73 shows how covering films 431k and 432k have first been removed using the removal flaps 4311k and 4321k, after which sections 5k, 2k, 321k, 322k and 32k have been bent together over the curved fold 33k such that sections 32k and 33k are stuck to a new section 3k and section 2k ends up on the other side of skin tag 21k. Because the four sections 312k and 322k, and 311k and 321k were asymmetrically placed between sections 31k and 1k each between 32k and 2k in FIG. 70, both pairs 312k and 332k, and 311k and 321k of the four narrow sections extend in parallel, which means that 2k with sections 321k and 322k can be moved in relation to section 1k on the skin, the parallel sections 311k and 312k and the new section 3k.

In FIG. 74, protective film 2k has been removed using the removal flap 421k, after which section 2k has been stuck to the skin on the other side as near skin tag 21k as possible and edge to edge with section 1k. Following this, it is rotated by the double thick, stabilised section 3 in the direction of the arrow 30k, winding the four narrow, adhesive sections 322k, 312k, 321k and 311k around the base of skin tag 21k.

After one to three twists, the narrow sections 322k, 312k, 321k and 311k have been wound around and stuck to the base of the skin tag occluding both the venous and arterial capillaries in skin tag 21k, FIG. 75.

In FIG. 76, it is possible to bend the occluded skin tag 21k and section 3k on the top side of the sections 1k and 2k which are stuck to the skin surface. The adhesive surface of section 5k is activated by means a removal flap 451k to remove protective film 45k.

FIG. 77 shows how it is possible to fold section 5k in the direction of the arrow 52k in FIG. 76 over the imprinted, curved fold 51k, which fixes section 3k and the occluded skin tag 21k parallel to the skin surface and at the same time hides them from sight, which increase the cosmetic acceptance of the invention.

Example 12

In the embodiment of this invention, the base of the skin tag is compressed against a hard surface of narrow, adhesive sections which are wound several times around one side of the skin tag.

FIG. 78 is an overview of the band-shaped device which is made up of four thin, more or less connected sections 1m, 2m, 3m and 5m, consisting of a more or less elastic or flexible material of polymer or natural material, and a massive or ring-shaped section 6m of a more or less flexible material of polymer, metal, salt or natural material with a more or less hard and incompressible surface and a height which can vary between 0.1 and 15 millimetres. Section 6m is stuck between the two thin, band-shaped sections 1m and 2m, where at least section 1m lying on top of the skin has a larger area than section 6m. Section 2m has an adhesive surface underneath which is facing away from section 6m, while section 1m has an upper side which can either be adhesive or non-adhesive. Between sections 1m, 2m and 5m, there is an aperture 11m extending through both sections 1m and 2m, which extends right to the more or less hard and incompressible surface of section 6m. Section 5m has an adhesive upper side which is covered by protective film 45m with removal flap 45m and connected to section 2m by the imprinted fold 51m. Sections 3m and 31m has adhesive upper sides and are independent sections of 5m and are covered by the transparent protective film 431m with removal flap 431m. The flap-formed section 3m is fixed by the narrow, independent section 31m to section 5m by the side of the common imprinted fold 51m between sections 2m and 5m.

FIG. 79 is a perspective view showing how protective film 42m on section 2m has been taken off using removal flap 421m, after which section 2m of the device has been stuck to the skin 20m such that skin tag 21m is located as near as possible to the more or less hard and incompressible surface of section 6m.

In FIG. 80, protective film 431m has been removed using removal flap 4311m, flap 3m has been gripped with two fingers 22m and 23m and section 31m is stretched out and twisted one turn clockwise around section 6m between sections 1m and 2m, as shown by the arrow 30m, such that skin tag 21m is squeezed against the more or less hard and incompressible surface of section 6m.

FIG. 81 is a cross section along the line LXXXl-LXXXl in FIG. 80, showing how section 3m is wound three times around section 6m and how the base of the skin tag is then compressed and pushed against the hard and incompressible surface of section 6m. The occluded skin tag 21m is then bent and stuck to the adhesive surface 1m.

In FIG. 82, protective film 45m has been removed using removal flap 451m and section 5m is bent down on the imprinted fold 51m over the skin tag 21m in section 1m. Because the area of sections 1m and 2m is smaller than section 5m, the areas of section 5m lying outside the range of sections 1m and 2m will be stuck to the skin, thus fixing, concealing and sealing skin tag 21 on the skin.

Example 13

In this embodiment of the invention the device is made up of two parts, where one part produces an occlusion of the skin tag as a result of the torsional force that arises when the more or less flexible and elastic device is turned or rolled.

FIG. 83 is an overview of the part of the band-shaped device 1n, which has a centrally located aperture 11n between sections 12n and 13n on either side of the aperture. On the outer edge of short side, sections 12n and 13n each have their own projecting, pointed flaps 14n and 15n, facing in opposite directions. The underside of the device 1n has an adhesive surface which is covered by protective film 41n which is extended on the short side of device such that a removal flap 411n arises.

In FIG. 84, a perspective view of the other part of device 2n is shown which is also band-shaped of a length which is more or less longer and a width which is narrower than section 1n of the device. Section 2n of the device has an adhesive underside which is inactivated by protective films 42n and 43n each with removal flaps 421n and 431n.

In FIG. 85, protective film 41n has been removed from section 1n of the device using the removal flap 411n and the aperture 11n has been pulled over skin tag 21n, after which sections 12n and 13n of the device have been carefully stuck to the skin 20n. One finger is drawn along the skin surface towards the point of the flap 14n and another finger is drawn in the opposite direction towards the point of the flap 15n. Because sections 12n and 13n with flaps 14n and 15n are stuck to the skin 20n, continuous movement and exertion of pressure of the fingers on the top side of sections 12n and 13n will result in flaps 14n and 15n being rolled up onto each side of these sections 12n and 13n. Because sections 12n and 13n are hour-glass shaped, with more material on the short sides than at the aperture 11n; the rolled up sections 12n and 13n will move in circle around skin tag 21n as indicated by the activity arrow 75n.

FIG. 86 is a perspective view showing that continuous rolling 22n and 23n with two fingers from a diametrically opposing direction, as indicated by activity arrows 71n and 72n, the hour-glass shaped surfaces of sections 12n and 13n will be rolled up, as indicated by activity arrows 73n and 74n. Sections 31n and 32n on either side of aperture 11n will be turned around each other because of the opposing rotational direction of sections 12n and 13n. After a certain number of turns, sections 31n and 32n will have turned around and got stuck to each other and to the base of skin tag 21n. They will then be stuck to each other; their more or less flexible and elastic qualities will occlude the base of the skin tag.

FIG. 87, is a cross section showing how the adhesive surface of section 2n of the device is activated by removal of protective films 42n and 43n each with their respective removal flaps 421n and 431n, after which section 2n is stuck over the rolled up section 1n. The skin tag 21n which is occluded in the section in of the device is then sealed on the surface of the skin 20n.

Example 14

This embodiment of the invention is made up of a bent, tube-shaped, adhesive device, which through the more or less flexible and elastic polymer or natural materials of the device, and a slit in the tube can occlude and fix the skin tag to the skin surface.

FIG. 88 shows a device, 1p, which is made up of a short and narrow, more or less bent tube with radius 14p consisting of more or less flexible and elastic polymer or natural materials, where both the inner and outer surface 15p of the device 1p are adhesive. The tube-shaped device 1p has two open ends 12p and 13p as well as a slit, 11p, cut transversally in the wall in the pipe in the middle of the convex part of the device 1p with the radius 14p.

To apply the tube-shaped device 1p, in FIG. 89, the open surfaces 12p and 13p are held between the thumb 22p and the forefinger 23p and the ends of the tube are squeezed together so that the radius 14p is reduced and the tube curves, whereby the transversal slit 1p widens.

In FIG. 90, while device 1p is still being squeezed, the two open ends 12p and 13p are pushed through the widened slit 11p such that the edges of the slip 1p extend to the base of the skin tag 21p.

FIG. 91 shows how squeezing of the open sides 12p and 13p of device 1p with fingers 22p and 23p has ceased, whereby the slit, 1p, by the inherent flexibility and elasticity of the polymer or natural material in device 1p, is pressed together occluding the base of the skin tag 21p. To enhance the squeezing effect of slit 11p, the lowest part of the gap of both open sides 12p and 13p is pressed down using the fingers, 22p and 23p, until part of the adhesive surface 15p is stuck to the skin surface 20p which causes the radius 14p to be straightened out in a line which follows the skin surface, and causes a narrow section of the cylindrical, total surface area of device 1p to stick to the skin surface 20p.

In FIG. 92A, the open, circular side is pushed together with a finger, 22p, causing it to take on a more elliptical shape, where the adhesive outside 15p sticks to the skin 20p and the two increasingly parallel, adhesive inner walls stick to each other.

In FIG. 92B, the cylindrical device 1p has been pressed together and the inner surfaces stuck to each other around skin tag 21p which has then been sealed within device 1p. At the same time, the adhesive outer surface 15p of the cylindrical device 1p is stuck to the skin 20p, fixing the sealed skin tag 21p to the skin. The top surface of the device 1p stuck to the skin is then easily covered with a conventional plaster or the like in order to enhance cosmetic acceptance.

In another embodiment of the invention, the upper half of the short, more or less bent, tube-shaped device 1p can be covered by a non-removable, more or less flexible, non-adhesive protective film which facilitates squeezing of device 1p in FIGS. 92A and 92B and eliminates the risk of device 1p stuck on the skin adhering to clothes and other objects in the environment.

Example 15

This embodiment of the invention is based upon the skin tag first being placed in an aperture in the device, after which a V-shaped section of the device is pulled against the base of the skin tag, thus occluding it with its V-shaped point. During the occlusion, the section slide on the protective film which, because it is stuck to the V-shaped section when removed, simultaneously pulls the two legs of the V-shaped section thus resulting in an occlusion of the base of the skin tag.

FIG. 93 is a perspective view showing a device consisting of three connected parts 1r, 2r and 3r, all of which have an adhesive underside. Section 1r has a circular, centrally located aperture 11r and a protective film 41r with a removal flap 411r on the underside and on the similarly adhesive upper side another protective film 4111r, which extends past the adhesive surface of 1r. Section 2r has a larger area than section 1r, with a protective film 42r and a removal flap 421r on the adhesive underside. On the underside of section 3r there is a protective film 43r which projects on both sides of the section, eliminating the need for a special removal flap. On the upper side of section 3r, there is a protective film 4311r, which extends past the adhesive surface of section 3r, through a fold which lies between sections 3r and 1r. Through the two protective films 4111r and 4311r, a V-shaped recess has been punched out in the central part of section 3rr, which causes section 3r to have two legs, which are V-shaped with points pointing towards section 1r.

In FIG. 94, the two protective films 4111r and 4311r have been bent upwards as indicated by activity arrow 70r in FIG. 93, such that the point where the two legs of section 3r coincide can be seen more easily.

In FIG. 95, the protective film 41r has been removed using removal flap 411r and section 1r of the device has been stuck to the skin 20r, such that skin tag 21r sticks up through aperture 11r.

In FIG. 96, notch 31r in the two protective films 4111r and 4311r has been folded over skin tag 21r, as shown by activity arrow 71r in FIG. 95. The stabilising protective film 43r has then been removed and notch 31r in section 3r has been folded over skin tag 21r using section 2r. Then protective film 4311r is removed to activate the adhesive surfaces of the two V-shaped legs 3r.

In FIG. 97A, the two protective films 4311r and 4111r can slide towards each other causing the power used for rolling off the protective film 4311r from the adhesive underside of section 3r and protective film 4111 from the upper side of section 1r to a stretching of the two V-shaped legs 3r, and at the same time move section 2r in the direction indicated by activity arrow 74. When the correct amount of stretching of the two legs 3r has been reached and the base of skin tag 21r has been stuck and occluded by the sides of the two legs 3r facing notch 31r, some of the adhesive surface of 3r will stick to section 1r at protective film 411r. When protective film 4111r is then removed as indicated by activity arrow 74, the two legs 3r are stretched further because of the slight adhesion between section 3r and the protective films and the adhesive surfaces and the adhesive surfaces of sections 1r and 3r will finally be stuck to each other.

In an alternative embodiment of the invention, shown in FIG. 97B, the more or less flexible and elastic legs 3r are stretched using 2r in accordance with activity arrow 74r and then the stretched legs are successively locked by pulling off the protective film 4111r as indicated by the arrow 73r. By stretching the two legs 3r, the base of skin tag will be occluded from the sides by the tapered V-shaped notch.

FIG. 98 illustrates how skin tag 21r is bent down onto the adhesive surface of section 3r, after which protective film 42r is removed using removal flap 421r, and section 2r is then bent down over the skin tag 21r which has been occluded by sections 1r and 3r and thereby sealed and fixed to the skin surface.

Example 16

This embodiment of the invention is based upon tangential slits being punched, cut, incised, or in another way created in a concentric zone between the central and peripheral parts of a circular device.

FIG. 99 is a perspective view of a thin, circular, more or less flexible and elastic disc consisting of two sections 1s and 2s. The underside of the disc is adhesive and covered by a centrally positioned protective film 41s and by a peripheral protective film 42s which projects beyond the outer circular area of the device. In the centre of the disc-shaped device is an aperture 11s, at the bottom of which a slit line 43s emanates, extends through protective film 41s and right up to the periphery of protective film 42s. Two removal flaps for each of the protective films are then created.

FIG. 100 is a perspective view, showing how a number of thin bow-formed cuts 3s have been punched, cut or incised in the outer peripheral part 31s of section 1s.

FIG. 101 is a perspective view showing how protective film 41s has been removed from the central section 1s and its outer part 31s, and how aperture 11s in the device has been pulled over skin tag 21s and the central part of section 1s has been stuck to the skin surface 20s.

FIG. 102 shows how section 2s has been turned clockwise around section 1s which is stuck to the skin, as indicated by activity arrow 73s. The more or less flexible and elastic, peripheral part 31s in FIG. 101 is pulled through the cuts 3s and transformed to thin, band-shaped units 32s in FIG. 102 with an adhesive underside. These units 32s, which slide on protective film 42s during the clockwise twisting of section 2s in relation to section 1s, will wind themselves around the base of skin tag 21s through their elasticity and flexibility and occlude the capillary blood flow. Protective film 42s is then removed and section 2s is stuck to the skin. The flexible and elastic units 32s tied around the base of the skin tag cause atrophy and rejection of the skin tag 21s. To conceal and fix the occluded skin tag 21s, a disc without an aperture 11s can be applied as indicated in FIG. 99, or a conventional plaster can be applied.

Example 17

In this embodiment of the invention, the occlusion is obtained through a double-sided eccentric mechanism, where the base of the skin tag is squeezed from two diametrically opposite sides.

FIG. 103 is a perspective view of a thin, more or less flexible and elastic device, consisting of four connected sections 1t, 2t, 3t and 4t. Section 1t has an adhesive underside covered by protective film 41t with removal flap 411t, and a centrally located square aperture, 11t, more or less larger than the two sections 31t and 32t, which through a fold are placed opposite each other on either side of section 1t. Sections 31t and 32t have adhesive top sides covered by protective films 431t and 432t; and thin, flexible, harder, central parts 313t and 323t, surrounded by a softer frame of thin, adhesive, flexible and elastic material with the small indentations, 312t and 322t, opposite each other. Running transversally over the thin, flexible, harder central parts of each of the sections, 313t and 323t are the imprinted folds 311t or 321t. Section 2t, located on the other side of section 1t, has a larger area than 1t with an adhesive top side covered by protective film 42t with removal flap 421t.

In FIG. 104, protective film 41t has been removed using removal flap 41 it and section it has been pulled over the skin such that skin tag 21t ends up as near as possible to the middle of the square aperture, 11t, after which section 1t of the device is stuck to the skin, 20t.

In FIG. 105, the two protective films, 431t and 432t, have been removed and sections 31t and 32t have been folded over the edges of section 1t and the square aperture 11t. By carefully bending the pre-prepared folds 311t and 321t in sections 31t and 32t, it is possible to bend the thin, flexible and harder sections 313t and 323t, and place their surrounding soft, flexible and elastic frames with indentations 312t and 322t as near as possible to the skin tag without them sticking to the skin in the aperture lt.

FIG. 106 illustrates how by pressing the upright pre-prepared folds, 311t and 321t down, it is possible to get the indentations 312t and 322t, located opposite each other at the base of skin tag, 21t, to move nearer to each other. The thin, flexible and harder parts 313t and 323t then stick to the skin in the aperture 11t, and at the same time, the base of the skin tag 21t is occluded and stabilised on the skin.

FIG. 107 illustrates how protective film 421t is removed using removal flap 42t, and section 2t is bent over the occluded skin tag, 21t. Because of its size, section 2t will completely cover the occluded skin tag in section 1t. The skin tag is then sealed to the skin surface.

Example 18

In this embodiment of the invention, a reversed eccentric principle with two opposing units is used to occlude the base of the skin tag.

FIG. 108 is a perspective view of a device which is made up of four more or less elastic and flexible, connected sections 1u, 2u, 31u and 32u with protective films on the adhesive surfaces of the sections, indicated by the broken lines. Section 1u has an adhesive underside which is inactivated by protective film 41u with removal flap 411u. In the central part of section 1u, there is a notch 11u which is as wide as the two sections 31u and 32u combined. Its length is correlated to the length of sections 31u and 32u, allowing a sufficient occlusion of the base of the skin tag to be achieved during the inversed eccentric movements. In the middle of sections 31u and 32u located opposite each other, there are two transversal pre-imprinted folds which give rise to two zones 313u and 312u, or 323u and 322u, which in relation to the rest of the device are more or less more rigid, and which more easily can be bent in relation to each other and to the other part of each of the sections 31u and 32u. Each of the sections 31u and 32u have a triangle-shaped aperture, 311u and 321u, with the point pointing out towards the free, short side of respective sections and an adhesive top side which is covered by its own protective film 431u and 432u with removal flaps 4311u and 4321u. On a third side of section 1u, there is a section 2u, the length and width of which is more or less greater than that of section 1u. Section 2u has an adhesive top side which is covered by protective film 42u with removal flap 421u.

In a perspective view of the device in FIG. 109, the protective film 41u has been removed using removal flat 411u, and section 1u has been stuck to the skin so that the skin tag 21u ends up in the middle of notch 1u. The protective film 431u is then removed using removal flap 431u and section 31u is then folded over section 1u in such a manner that the aperture 311u is pulled over the skin tag, 21u. By bending sections 312u and 313u, as shown in FIG. 109, the pointed fold in the triangle-shaped aperture 311u can be drawn against the base of the skin tag 21u to achieve an occlusion of the blood flow.

FIG. 110 shows how the adhesive sides of sections 312u and 313u are almost completely pressed together, and how the occlusion is initiated from the other side by removing protective film 432u, using removal flap 4321u; folding in section 32u, and pulling the triangle-shaped opening 321u over the skin tag 21u such that section 32u ends up lying on top of section 31u.

FIG. 111 shows how, by continuing folding and successively sticking sections 322u and 323u to each other, the pointed tip of the triangle-shaped aperture 321u occludes the base of the skin tag 21u from the opposite direction compared to the pointed tip of the triangle-shaped aperture in section 31u, significantly enhancing the effect of the occlusion.

In FIG. 112, the two joined sections 312u and 313u, and 322u and 323u, have been folded over sections 31u and 32u, respectively. The protective film 42u in section 2u has been removed using removal flap 421u and stuck on top of sections 31u, 32u and 1u to lock, fix and conceal the occluded skin tag, 21u to the skin surface.

Example 19

This embodiment of the invention is based upon a band-shaped device with three sections, each of which has a central aperture. The sections can be bent, stretched or stuck on top of each other in such a manner that the central aperture in each section is moved in relation to the aperture in the other sections, leading to an occlusion of the base of the skin tag.

FIG. 113 shows an overview of a thin, more or less flexible, band-shaped device consisting of an H-shaped section with two legs 1v and 2v and a narrower connection 31v with the central aperture 311v in the middle of the legs. The first section has an adhesive underside, covered by protective film 41v with removal flap 411v. Another H-shaped section consists of legs 5v and 6v with a connection 32v with aperture 321v in between the legs, and an adhesive top side, with protective film 45v and removal flap 451v. A third section has legs 7v and 8v with a connection 33v in between the legs, and a central aperture 331v, and an adhesive top side with protective film 47v and removal flap 471v.

FIG. 114 shows how protective film 41v has been pulled from underneath sections 1v and 31v and the central aperture 311v has been pulled over the skin tag, 21v. Section 31v has then been stretched in the direction indicated by activity arrow 71v; the round aperture 311v1 is thus stretched into an oval aperture 311v2, and the right side of the base of the skin tag, 21v, is thus occluded. When the stretching and occlusion is deemed satisfactory, and section 2v is stretched a distance 72v; the protective film 41v is removed from underneath section 2v, and then stuck to the skin.

FIG. 115 is a cross section along CXV-CXV in FIG. 114 showing how by stretching section 2v a distance 72v has lengthened section 31v and aperture 311v, as indicated by the activity arrow 71v, such that the aperture 311v is extended on one side into position 311v1, enabling the other side of skin tag 21v to be occluded.

FIG. 116 shows how protective film 45v has been removed from section 5v and 32v using removal flap 451v. Sections 5v, 32v and 6v are then folded over sections 1v, 31v and 6v lying on the skin, and aperture 321v is pulled over skin tag 21v, after which section 5v is stuck on top of section 2v. Section 32v is then stretched using section 6v, distance 76v, as indicated by the activity arrow 75v, until the aperture 321v is extended to a position 321v1 which is sufficient to enable the base of the skin tag 21v to be occluded from the side opposite to that achieved with aperture 311v in position 311v1.

FIG. 117 is a cross section of FIG. 116 along to line CXVII-CXVII and shows how the base of skin tag 21v is subjected to tightening in the same direction as the elongation of different layers 1v, 31v, 2v and 5v, 32v 6v, thus occluding the blood flow.

In FIG. 118, the upright sections 7v, 33v and 8v in FIG. 116 have been folded down, stretched and stuck over sections 6v, 32v and 5v, such that the aperture 331v is stretched to a new form 331v2 to increase the occlusion of the base of the skin tag 21v.

FIG. 119 is a cross section of FIG. 118 along the line CXIX-CXIX and shows how section 1v has been stuck to the skin and 20v and how section 31v with aperture 311v1 has been stretched to the new position 311v2 using section 2v, thus pressing and occluding the lower part of skin tag 21v. Likewise section 5v is stuck on top of section 2v and this extension 22v and how section 321v is stretched to a new position 321v2, using section 6v, which presses and occludes the base of the skin tag in the opposite direction. Finally, FIG. 119 shows how section 7v is stuck to the stretched sections 6v and 62v, and how section 33v is stretched with section 8v so that the aperture 331v reaches a new position, 331v2, which presses and occludes skin tag 21v in the opposite direction compared to the underlying layers 5v, 32v and 6v.

FIG. 120 is a simplified and reduced overview of FIG. 118 showing how 1v and 2v of the original band-shaped device in FIG. 113 is stuck to the skin and how the two other sections 5v and 6v as well as 7v and 8v are then bent over each other and together form three layers on top of the skin around the occluded skin tag 21v.

FIG. 121 shows an independent, more or less elastic section 9v, originating from the original band-shaped device in FIG. 113, which has a surface which on all sides is larger than the total area created by the three joined sections 1v, 31v, 2v and 5v, 32v, 6v, and 7v, 33v and 8v. The independent section 9v has an adhesive side which is covered by protective film 49v with removal flap 491v.

In FIG. 122, the protective film 49v has been removed using removal flap 491v and section 9v has been stuck on top of the three layers of the band-shaped device in FIG. 113, which occludes skin tag 21v. Section 9v is applied in such a manner that the entire device in FIG. 120 is completely covered and the occluded skin tag 21v is folded down and fixed parallel to the skin surface, using the adhesive side of 9v.

Example 20

The embodiment of the device is based upon a device consisting of a softer, adhesive under layer and a harder top layer with flaps bending in, which when bent into the centre from different sides, will occlude the base of the skin tag in the centre.

FIG. 123 is an overview of a device, consisting of two layers, where the bottom layer consists of a square or circular thin, soft, more or less flexible section 2x with a centrally located aperture 11x, which on the underside is covered by a protective film 42x with a removal flap 421x. On top of the bottom section 2x, there is an upper, more rigid section 1x with an adhesive underside which in its peripheral outer edge is connected with the bottom section 2x. The central area of the upper part of the section 1x is cut out for example flaps 31x, 32x, 33x and 34x, which are bent backwards over the outer edge of the peripherally connected sections 1x and 2x and covered by a protective film 41x, with removal flap 411x. Flaps 31x, 32x, 33x and 34x have in their free points a little radius which when folded in towards the central aperture 11x in the bottom part 2x of the device occludes the base of the skin tag 21x in an optimum manner.

FIG. 124 is a cross section of FIG. 123 along the line CXXIV-CXXIV and shows how section 1x and 2x are connected in the periphery and how the incised flaps 31x and 33x with their respective free pointed radii 311x and 331x in the upper section 1x of the device have been folded back from the central part with aperture 11x in the bottom part 2x of the device and fixed permanently in this position by protective film 41x.

FIG. 125 shows how protective films 41x and 42x have been removed using removal flaps 411x and 421x, and how the bottom part 2x of the device has been stuck to the skin 20x such that the skin tag 21x sticks up through the centrally located aperture 11x.

In FIG. 126, the four flaps 31x, 32x, 33x and 34x in FIG. 125 have been folded and at the same time drawn back in towards the central aperture 11x, until the pointed radii 311x, 321x, 331x and 341x push against the base of skin tag 21x. A finger is then pushed against the top side of each flap 31x, 32x, 33x and 34x such that the adhesive underside of the respective flaps sticks to the top side of the bottom part 2x of the device located on the skin 20x.

FIG. 127 illustrates, relative to sections 1x and 2x; an independent, thin, more or less elastic section 5x, whose adhesive side is covered by protective film 45x with removal flap 451x. The area of 5x is more or less larger than the area of section causing the occlusion of the skin tag 21x with sections 1x and 2x in FIG. 126.

In FIG. 128, protective film 45x is removed 451x from section 5x, which is then stuck on top of the occluded skin tag 21x in FIG. 126. Skin tag 21x is then folded down and stuck to one or some of the top sides of flaps 31x, 32x, 33x, or 34x of section 1x. Additionally, section 5x is applied to the skin 20x on top of skin tag 21x which has been occluded by section 1x in such a manner that the entire section 1x is covered, further sealing the device on the skin 20x.

Example 21

This Example is a variant of the previous Example 20, where the different flaps are given reinforced radii, facilitating the application of the device and occlusion of the skin tag. The device also consists of a built-in section for final covering and fixing of the occluded skin tag to the skin surface.

FIG. 129 is an overview of the band-shaped, more or less hard device consisting of two connected sections 1y and 2y united by a pre-prepared fold 12y, which is stuck to the skin 20y such that the skin tag 21y ends up in the middle of the big, open, central part of section 1y. The central part of section 1y is cut out into flaps 31y, 32y, 33y and 34y, each of which has an adhesive underside. In each of the four more or less hard flaps 31y, 32y, 33y and 34y, two sector-shaped folds have been imprinted, giving the flap the profile of a truncated cone, thus achieving greater stability and an enhanced, more controllable occlusion of skin tag 21y. In flap 31y, by punching out the flap, the tip of the flap has been given a little radius 313y, while simultaneously imprinting radii 311y and 312y from above. In the opposite flap 33y, the tip of the flap has been given a radius 333y and folds 331y and 332y have been imprinted from below. Equivalent punching out and imprinting has been carried out for flaps 32y and 34y each with tip radii 323y and 343y and reinforcing folds 321y and 322y and in 341y and 342y.

FIG. 130 is a cross section along the line CXXX-CXXX in FIG. 129 and shows how the two folds 31y and 33y from the beginning take on positions 31y1 and 33y1. The flaps opposite each other 31y and 33y, with their adhesive sides upwards, are then turned in towards the base of the skin tag, 21y, to positions 31y2 and 33y2 respectively. They finally end up in positions 31y3 and 33y3 respectively, where they stick to the skin and occlude the base of the skin tag 21y by means of radii 313y and 333y. The equivalent happens with the opposite flaps 32y and 34y, whose radii 323y and 343y will occlude the base of the skin tag in a straight angle to the flaps 31y and 32y already stuck to the skin, as shown in FIG. 131.

FIG. 131 is an overview showing how protective film 42y is removed using removal flap 421y in section 2y in FIG. 129 and is then bent along fold 12y over section 1y with the occluded skin tag 21y which is then turned down and stuck on top of one or some of the flaps 31y, 32y, 33y or 34y. FIG. 131 also shows how the opposing flaps 31y and 32y, and 33y and 34y with their reinforcing folds 311y and 312y, 321y and 322y, 331y and 332y, 341y and 342y and their radii 313y, 323y, 333y and 343y occlude the base of the skin tag 21y as previously described in FIG. 130.

Example 22

This Example according to the invention is a variant of Examples 10 and 16, where the astringent section of the device consists of a thin, elastic cone-shaped film or cloth, running from a central position in one section out to a peripheral position in the outer section.

FIG. 132 is an overview of a device illustrating a circular section 1z with an adhesive underside, consisting of a central circular disc. Stuck around the central aperture 11z in the disc, is a cone-shaped, more or less elastic and adhesive, thin film or cloth 3z. The other end of the cone-shaped film 3z is fixed around the inside of a ring-shaped section 2z, also with an adhesive underside, the diameter of which is more or less greater than the outer diameter of section 1z.

In FIG. 133, the central section 1z and the outer section 2z of the device according to the invention is divided such that the cone-shaped film 3z, located between them, is stretched to show its extend.

FIG. 134 is a cross section along the line CXXXIV-CXXXIV in FIG. 133, illustrating the positions of the ring-shaped protective films, 41z and 42z, the outer side of which projects beyond the adhesive areas forming continuous removal flaps. Also illustrated is the cone-shaped, more or less elastic, adhesive film 3z.

In FIG. 135, the protective film 41z has been removed from section 1z in FIG. 134 and the central aperture 11z has been pulled over the skin tag 21z, following which section 1z has been stuck to the skin 20z.

In FIG. 136, the outer section, 2z, is rotated concentrically outside the inner section 1z, as indicated by the activity arrow 70z, whereupon the existing film 3z between sections 1z and 2z is stretched, extended and folded over, thus occluding the base of the skin tag, 21z.

FIG. 137 illustrates how the protective film 42z is removed from the adhesive surface of section 2z using slit lines 421z and 422z; and then stuck to the skin surface 20z, locking occluding film 3z into an occlusive position around the skin tag 21z.

Example 23

This Example according to the invention is a modification of Example 16, where the occlusive sections are fixed to the device via a flexible upwards movement. The part of the section causing the occlusion consists of a reinforced, adhesive outer part and posterior notch making it more elastic and flexible.

FIG. 138 is an overview of a device consisting of a larger central section 3å with a centrally located aperture 11å and an adhesive underside covered by protective film 43å with a removal flap 431å. On one side of the central aperture 11å in section 3å, there is a lever 31å fixing and dividing a section into a central part 2å and a peripheral part 1å, and a lever 32å with section with the central part 5å and a peripheral part 4å. Located on the underside of sections 1å and 5å are protective films 41å and 44å respectively; and between section 2å and lever 31å and section 5å and lever 32å are protective films 42å and 45å, respectively. Part of the edges of sections 2å and 5å facing aperture 11å has been bent into folds 22å and 52å, and a number of notches 23å and 53å have been punched, incised or cut out in each section.

FIG. 139 is a cross section along the line CXXXIX-CXXXIX showing the central aperture 11å and how the lever 31å and 32å with their protective films 42å and 45å have been bent such that the distance between the turned up edges 22å and 52å is as great as possible. The positions of protective film 45å with removal flap 431å on the underside of section 3å and the two protective films 41å and 44å on the underside of the peripheral part of each section 1a and 4a are also shown.

FIG. 140 is an overview where the protective film 43å has been removed, skin tag 21å has been placed into aperture 11å and the entire section 3å has then been stuck to the skin, 20å. Protective films 42å and 45å in FIG. 139 have then been removed and the two levers 31å and 32å together with both their sections have been lifted up and bent forwards such that the turned up edges 22å and 52å are orientated towards the base of the skin tag 21å.

FIG. 141 is a cross section along the line CXXXXI-CXXXXI in FIG. 140, where the central parts 2å and 5å of the sections are maneuvered by means of peripheral parts 1å and 4å of the sections, together with levers 31å and 32å such that the edges 22å and 52å are stuck to the base of the skin tag 21å. Protective films 41å, 42å, 44å and 45å are then removed and sections 2å, 1å, 5å and 4å are stuck on top of section 3å. As a result, notches 23å and 53å are distorted, and via the opposite edges 22å and 52å exert a constant pressure on the base of the skin tag, 21å, occluding the blood flow. The skin tag 21å fixed upright on the skin surface can then be covered by a plaster, or operating tape, or a bandage to enhance its cosmetic appearance.

Example 24

In this example, the skin tag is squeezed between the turns of a spiral such that the base is occluded. The skin tag is lying inside the spiral and is then bent downwards and sealed to the skin surface.

FIG. 142 is an overview of a device constituting a short, more or less resilient spiral consisting of metal, polymer or a textile band 1ä which is covered on both sides by both sections 3ä and 5ä. Section 3ä has outside the spiral a one direction fold 31ä and a band-shaped section 32ä with an adhesive upper side, covered by protective film 43ä with removal flat 431ä. The other side of the spiral 1ä is covered by section 5ä, which via one direction fold 51ä, continues into the band-shaped section 52ä which has two adhesive sides covered by protective films 451ä and 452ä and their respective removal flaps 4511ä and 4521ä.

FIG. 143 is an overview showing an independent section of the device consisting of a thin, more or less flexible and elastic circular disc 6ä. Its adhesive side is covered by protective film 46ä, which has a slit line 461ä which facilitates removal of the protective film.

FIG. 144 is a vertical side view of the device in FIG. 142, where the spiral section 1ä is covered on both sides by sections 3ä and 5ä. After fold 51ä, section 5ä continues out the folded section 52ä, both sides of which are adhesive and covered with protective films 451ä and 452ä with respective removal flaps 4511ä and 4521ä. After fold 31ä, section 3ä is similarly angled out to section 32ä with an adhesive side, covered by protective film 43ä with removal flap 4321ä.

In FIG. 145, the two folded sections 32ä and 52ä, shown in FIG. 144, have been clamped together, upon which 3ä and 5ä, because of the one direction folds 31ä and 51ä, will open the more or less resilient spiral 1ä on the opposite side. The spiral 1ä is then pulled over skin tag 21ä and down onto the skin surface 20ä.

FIG. 146 shows how spiral 1ä is clamped around the base of skin tag 21ä, and how the protective film 451ä, which has been removed using removal flap 4511ä, has been bent over fold 51ä, and stuck to section 5ä. Protective film 452ä has then been removed using removal flap 4521ä and spiral 1ä containing the occluded skin tag 21ä has been bent downwards 90 degrees and stuck to the skin with section 52ä. Protective film 43ä has then been removed using removal flap 4321ä and bent over fold 31ä and stuck to section 3ä which is located on the horizontally fixed spiral 1ä encompassing the occluded skin tag 21ä. Finally, protective film 46ä is removed from section 6ä using slit line 261ä, as shown in FIG. 143, and section 6ä has then been stuck over the spiral section 1ä lying on the skin, which further fixes skin tag 21ä to the skin and conceals this occluded base rendering it cosmetically pleasing.

Example 25

In this example, according to the invention, the force used to occlude the base of the skin tag is taken up by a flexible and very short hinge-like connection between the two sections of the device.

FIG. 147 shows a thin, band-shaped device consisting of two equally large sections 1ö and 2ö with an adhesive underside covered by protective films 41ö and 42ö each with their own removal flaps 411ö and 421ö and which are held together by a thin, small and strong connection 12ö. A larger section 3ö with protective film 43ö and removal flap 431ö on the top side is connected to the long side of section 2ö in a foldable manner.

In FIG. 148, protective film 41ö is removed using removal flap 421ö, after which sections 1ö and 2ö are folded up over the short, flexible connection 12ö and section 1ö is stuck to the skin 20ö with skin tag 21ö as near as the connection 12ö as possible. After the protective film 42ö in FIG. 148 has been removed, section 2ö is stuck to the skin 20ö in FIG. 149 so near the long side of section 1ö that the base of skin tag 21ö is clamped and occluded near the short, flexible and strong connection 12b.

FIG. 150 shows how section 3ö is bent down over the occluded skin tag 21ö which then is sealed and immobilised parallel to the skin surface 20ö on top of sections 1ö and 2ö.

Example 26

The device in this example consists of a little, two-piece box with an adhesive underside which is stuck to the skin. The top side of the box can be moved, whereby the base of the skin tag in the box is occluded and finally is encased in the closed box.

The device consists of an upper part which is described in FIG. 151 and consists of a disc of metal, polymer or natural material 3aa, where three of the outer edges 32aa, 33aa and 35 of the disc are bent under the disc. On top of the fourth side there is a downwardly directed groove 34aa which forms part of a snap-lock. In section 3aa there is a transversal, vertical, parallel epipedic disc 31aa which is fixed to the surface of the disc. The vertical disc 31aa has a slightly resilient under edge 311aa allowing a gentle occlusion of the base of the skin tag 21aa as shown in FIG. 154.

The other part is described in FIG. 152, where a small, parallel epipedic box 1aa on the top side has three smooth, flared edges 14aa, 15aa and 15aa, while on the fourth side 13aa there is an upwardly directed groove which forms the second part in a snap-lock. Centrally in the bottom of the box 1aa, there is a semi-circular aperture 11aa, beside the edge of which there is a skewed, parallel epipedic disc 12aa hanging from the long side of box 1aa, the under edge of which is lightly resilient to, when in contact with the resilient edge 311aa in section 3aa, effectively and gently occlude skin tag 21aa. Under the bottom of the box 16aa, there is an adhesive layer which is covered by protective film 41aa with removal flap 411aa.

In FIG. 153, folds 32aa and 33aa in 3aa have been pulled over the flanges 14aa and 15aa in box 1aa in FIG. 152. Section 3aa in FIG. 151 now acts as a lid for box 1aa and can be moved backwards and forwards with precision, as shown by the activity arrow 36aa, which is necessary to ensure that the device according to the invention produces an occlusion.

FIG. 154 shows how protective film 41aa is first removed and how the skin tag 21aa is pulled through the aperture 1aa and placed in contact with the under edge of disc 12aa. Section 3aa which functions as a lid has then been permanently fixed to section 1aa using folds 32aa and 33aa, controlled by the flanges 14aa and 15aa which stabilise the movement of disc 31aa and the resilient edge 311aa against skin tag 21aa. The disc 31aa is then resilient against disc 12aa occluding base of the skin tag 21aa which is simultaneously bent over and behind the lower disc 12aa.

In FIG. 155, section 3aa has been moved on top of the entire section 1aa such that the snap-lock 33aa and 34aa are locked and the lock tension is maintained by the flange 16aa which is locked in fold 35aa. The resilient discs 31aa and 12aa are now locked against each other and stabilise the occluded skin tag within the device consisting of sections 1aa and 5aa locked in relation to each other.

Example 27

The device consists of two double-flanged, narrow wheels on top of each other, where the smaller upper wheel has an O-ring which can be bent down over the larger lower wheel and thereby occlude the base of the skin tag.

FIG. 156 is an overview showing the smaller double-flanged wheel 3ab with O-ring 31ab on top of the lower double-flanged wheel 1ab, where a little indentation 11ab has been made in the flanges. On the adhesive side of the lower wheel 1ab, there is a protective film 4ab with slit line 42ab.

FIG. 157 is a cross section of FIG. 156 along the line CLVll-CLVll, where the adhesive layer 41ab with its protective film 42ab is located on the underside of the double-flanged wheel 1ab with indentation 11ab. Above wheel 1ab is a similar double-flanged wheel 3ab with O-ring 31ab.

In FIG. 158, the protective film 4ab separated by slit line 42ab has been removed and the adhesive layer 41ab has connected the double-flanged wheel 1ab to skin surface 20ab, in such a manner that skin tag 21ab fits in the indentation 11ab.

In FIG. 159, O-ring 31ab has been rolled or folded down with the fingers 22ab and 23ab from the double-flanged upper wheel 3ab over the upper flange of the lower wheel 1ab which is stuck on the skin. Because of the greater radius of the lower wheel, 1ab, the O-ring 31ab will stretch and occlude the base of the skin tag, 21ab.

Example 28

This Example is a variant of Example 27, where the smaller, double-flanged, upper wheel is turned in relation of the under, larger, adhesive wheel.

FIG. 160 is an overview of the device where the upper double-flanged, smaller wheel 3ad is turned in relation to the larger, double-flanged wheel 1ad having its adhesive layer 4ad covered with protective film 41ad, the removal of which is facilitated by slit line 42ad and the area 13ad in between the wheels with aperture 12ad above indentation 11ad.

FIG. 161 is a cross section of FIG. 160 along the lines CLXl-CLXl demonstrating how the angle between the two double-flanged wheels 3ad with the O-rings 31ad and 1ad lying on the outside are covered by a thin wall 13ad with aperture 12ad. The lower double-flanged wheel 3ad with indentation 11ad and the adhesive underside 4a with protective film 41ad can also be seen.

FIG. 162 shows a thin, more or less flexible and elastic film 5ad with an adhesive side covered by protective film 34ad, the removal of which has been facilitated by slit line 451ad.

FIG. 163 is a front view of the device, showing the lower wheel 1ad with an indentation 11ad and the adhesive layer 4ad. Also shown are the upper wheel 3ad with O-ring 31ad and the thin wall 13ad with aperture 12ad lying between.

In FIG. 164, the protective film 41ad has been removed using slit line 42ad and the lower double-flanged wheel 1ad with its adhesive surface 4ad has been stuck to the skin 20ad in such a manner that the skin tag 21ad has ended up as far into the indentation 11ad as possible. The O-ring 31ad is then rolled or folded with a finger 23ad down over the thin wall 13ad causing the skin tag 21ad to be pushed through the aperture 12ad in the thin wall 13ad.

FIG. 165 shows how the O-ring 31ad occludes the base of the skin tag 21ad on the skin surface 20ad. Finally, the protective film 45ad is removed from the thin, adhesive, crescent-shaped film 5ad which is then stuck on top of the thin wall 13ad in FIG. 166, following which the occluded skin tag 21ad is enclosed and protected in the now enclosed space between the double-flanged wheels 1ad and 3ad.

Example 29

A third variant of the device with an occluding O-ring according to the invention is shown in FIG. 167, which is an overview of the band-shaped device, consisting of section 12ac with an adhesive underside covered by protective film 41ac with removal flap 411ac. Section 12ac has a aperture 11ac which is located next to the indentation 13ac in the double-flanged wheel 1ac. Placed concentrically above the upper wheel 1ac is an additional double-flanged wheel 3ac with a notch 14ac; over which the O-ring 31ac extends, and where the strap 32ac around O-ring 31ac can be clearly seen. The other section 5ac of the band-shaped device has an adhesive upper side which is covered by protective film 45ac with removal flap 451ac.

FIG. 168 is a cross section along the line CLXVlll-CLXVlll in FIG. 167 and shows section 12ac of the device with the double-flanged wheel 3ac with its notch 14ac; O-ring 31ac and strap 32ac extend concentrically on top of the other wheel 3ac with indentation 13ac and the aperture 11ac located outside. Section 12ac has an adhesive underside with protective film 41ac and removal flap 411ac. It is also possible to see that the other section 5ac of the device has an adhesive upper side with protective film 45ac and removal flap 451ac.

In the longitudinal section shown in FIG. 169, the removal flap 411ac has been used to remove the protective film 41ac, after aperture 11ac is pulled over skin tag 21ac and section 12ac is stuck to the skin 20ac. The strap 31ac is then gripped between the thumb 23ac and the forefinger 22ac and pulled out and over skin tag 21ac.

FIG. 170 is a longitudinal section where the strap 32ac has been released by the fingers 22ac and 23ac, and O-ring 31ac has contracted in the double-flanged wheel 1ac occluding the base of the skin tag 21ac in indentation 13ac. At the same time, skin tag 21ac has been folded in through the notch 14ac into the empty central space in the double-flanged wheels 3ac and 1ac.

FIG. 171 is a longitudinal section, showing how the strap 31ac has been folded in through the notch 14ac and how protective film 45ac in FIG. 170 has been removed using removal flap 451ac. The adhesive surface of section 5ac has been stuck over section 12ac which is then sealed with the occluded skin tag 21ac on the skin surface.

Example 30

In this example according to the invention, an occlusion can be achieved through a minute aperture and the inherent elasticity of the device.

The cone-shaped, elastic device 1af in FIG. 172 has according to the invention four arms 12af, 13af, 14af and 15af extending from a common central part, in the centre of which is a minute aperture 11af. The underside of the four arms 12af, 13af, 14af and 15af and the central part between the arms is adhesive and covered by protective films 4af and 44af and removal flaps 41af and 441af. Above arms 12af and 15af and fixed to the common central part is a pair of similar-sized arms 17af and 16af, each of which have their own adhesive underside which is covered by protective film 47af with removal flap 471af and protective film 46af with removal flap 461af.

In FIG. 173, protective film 4af has been removed using removal flap 41af and the two arms 12af and 15af and half of the common central part of section 1af has been stuck to the skin 20af such that the skin tag 21af is located as near the minute aperture 11af as possible. The FIG. also shows how the free arms 13af and 14af with protective film 44af and removal flap 441af are gripped between the thumbs and forefingers 23af and 22af, or 25af and 24af.

Using the thumbs and forefingers 23af and 22af and also 25af and 24af, the specially elastic, common, central part of the device is stretched 1af in FIG. 174, together with arms 13af and 14af such that the minute aperture 11af is stretched and pulled over the skin tag, 12af, while the arms 12af and 15af stuck to the skin, with their arms 17af and 16af fixed to the central part, resist the force produced by fingers 22af, 23af, 24af and 25af.

In FIG. 175, the stretching of the common elastic part of the device 1af has ceased and aperture 11af contracted to its original size, occluding the base of the skin tag 21af. The protective film 44af has been removed using removal flap 441af, after which the relaxed arms 13af and 14af stick to the skin surface 20af.

FIG. 176 shows how the protective films 46af and 47af are removed using removal flaps 461af and 471af, after which arms 16af and 17af are folded down from two different directions over the centrally placed skin tag 21af which is then stuck and fixed to the upper side of the common elastic part of the device 1af on the skin surface 21af. It is also possible to partially pull off protective films 4af and 44af in FIG. 172, and then grip the device with both hands and with one's fingers in the central part, stretch out the aperture 11af, pull it over the skin tag 21af, and then letting the central part between arms 12af, 134af, 14af and 15af contract such that the aperture 11af occludes the base of the skin tag shown in FIG. 175.

The protective films 4af and 44af are then removed, and the four arms 12af, 13af, 14af and 15af are stuck to the skin surface 20af, arms 16af and 17af are then folded over the skin tag, 21af, which is sealed to the skin surface 20af as shown in FIG. 176.

Example 31

The occlusion of the skin tag according to the invention in this example has been achieved by a low and a high wing in the lid or in the bottom of a round, portion-like, more or less hard device. When the lid of the device is turned in relation to the bottom, the base of the skin tag is clamped between the two wings such that an occlusion of the blood flow occurs.

FIG. 177 is an overview showing the bottom part of the device 1*ag* with an adhesive underside which is covered by protective films 41*ag* and 43*ag* which can be removed using slit line 42*ag*. A narrow tube 17*ag* is fixed centrally in the bottom of section 1*ag*, from which extends a low wing 15*ag* which is fixed in the outer wall of section 1*ag* and which has a free, more or less bent and slightly resilient under edge to 16*ag*. Under and next to the resilient edge 16*ag* is an aperture 11*ag* in the adhesive bottom of section 1*ag*. On the upper edge of the inside of the circular wall in section 1*ag*, there are two diametrically opposite, narrow bands, at the end of which are small, parallel epipedic areas 12*ag* and 13*ag*. Peripherally outside the circular wall of section 1*a* there is a circular track of two grooves 14*ag* facing towards each other.

FIG. 178 is an overview of the other section 3*g* of the device with a centrally placed tube 37*ag* in the lid, from which extends a fixed wing 36*ag* which does not reach the circular wall of the section. The high wing 36*ag* has a convex, bent, more or less resilient, and free under edge, 361*ag*. At the top edge of the outside of the circular wall in section 3*g*, there are two bands 32*ag* and 33*ag* located opposite each other with parallel epipedic surfaces which are turned towards the other side in relation to the areas on the bands 12*ag* and 13*af* in FIG. 177. On the lower edge of the circular wall of section 3*ag*, there is a narrow, outwardly directed, circular rim 34*ag*.

FIG. 179 shows how protective films 41*ag* and 43*ag* have been removed and how section 1*ag* has been stuck to the skin 20*ag* with skin tag 21*ag* sticking up through the aperture 11*ag* as near the low wing 15*ag* and its edge 16*ag* as possible.

In FIG. 180, section 3*ag* is positioned as a lid over section 1*ag* of device 31*ag*, where the connected tubes 17*ag* and 37*ag* help to centre and stabilise the device on the skin 20*ag*. The union formed by the rotatable snap-lock 143*ag* of the two grooves 14*ag* in FIG. 177 and the rim 34*ag* in FIG. 178 is also stabilised. The lid 3*ag* is positioned in such a manner that the two diametrically opposite bands 12*ag* and 13*ag*, as well as bands 32*ag* and 33*ag* do not get too near to each other and that the large wing 36*ag* with its free lower edge 361*ag* is placed behind skin tag 21*ag*.

In FIG. 181, the lid 3*ag* in device 31*ag* has been turned clockwise as indicated by the activity arrow 7*ag*, after which the two small, parallel epipedic, turned areas in bands 12*ag* and 32*ag* and 13*ag* and 33*ag* can slide over each other but lock into each other when the high wing 36*ag* and its lower edge 361*ag* compress the base of the skin tag 21*ag* against the low wing 15*ag* and its lower edge 16*ag*. At the same time, the high wing 36*ag* presses the occluded skin tag 21*ag* above the upper edge of the low wing 15*ag*. The skin tag 21*ag* is now concealed and occluded between the resilient edges 16*ag* and 361*ag* and is fixed on the skin surface 21*ag* as long as snap-lock 143*ag* is connected.

Example 32

In this example, according to the invention, the device consists of two sections, where in one of the adhesive sections, there is an arranged thread which is tied around the base of the skin tag, causing an occlusion, and where the other section conceals and stabilises the skin tag on the skin surface.

FIG. 182 is a perspective view showing a band-shaped, more or less elastic and flexible section 3*ah* with an adhesive underside covered by protective films 31*ah* and 32*ah* which is divided by slit line 321*ah*.

The other part of the device is shown in FIG. 183 and is made up of a primarily round, more or less flexible and elastic disc-shaped section 1*ah* with a centrally located aperture 11*ah*, and an adhesive underside which is covered by protective films 41*ah* and 43*ah* which are divided by slit line 431*ah* which facilitates the removal of the protective film. At the other side of the aperture 11*ah*, there is a weak adhesive tape, holding a mono- or polyfilament thread which has an area with a high friction coefficient, and where the free ends of the thread 13*ah* and 14*ah* are arranged around the aperture, 11*ah*.

In FIG. 184 protective films 41*ah* and 43*ah* are removed and section 1*ah*, with the centrally fixed thread by tape 12*ah* and its free ends 14*ah* and 15*ah* are stuck to the skin 20*h* in such a manner that the skin tag 21*ah* ends up in aperture 11*ah*.

FIG. 185 shows how both ends 13*ah* and 14*ah* of thread fixed by the tape have been twisted around each other and wound around the base of the skin tag 21*ah* such that a knot or tie 15*ah* is formed.

FIG. 186 is a continuation of FIG. 185 where both ends 13*ah* and 14*ah* of the thread are pulled in the direction of the arrows, such that the knot or tie 15*ah* is pulled so hard that the weak, adhesive tape 12 no longer can hold the thread which together with the knot or tie occludes the base of the skin tag 21*ah*. The protective films 31*ah* and 32*ah* are then removed and section 3*ah* is stuck to the skin, concealing and fixing the occluded skin tag 21*ah* to the skin surface 20*ah*.

Example 33

A variant of Example 32, where the device consists of two more or less hard and flexible circular sections 1*ai* and 3*ai* where the skin tag has been occluded by a more or less hard counterbalance.

FIG. 187 shows section 3*ai* in the form of a low cylinder 3*ai* which is open at one end with a circular edge turned out into a groove 31*ai*.

The other section of the device is shown in FIG. 188 and is made up of a thin, circular, more or less hard and flexible disc 1*ai* with an adhesive underside covered by protective films 41*ai* and 43*ai* divided by the removal slit line 431*ai*, and a centrally located aperture 11*ai* and an inwardly directed groove 13*ai* running around the circular edge locking it to groove 31*ai*, as described in FIG. 187. At the edge of the aperture 11*ai*, there is a more or less firm cylinder 12*ai* located on a double-sided adhesive ring 17*ai* extending around a thin, round aperture 11*ai* on the underside of section 1*ai*. On either side of the cylinder 12*ai*, there is a thin, mono- or multifilament thread draped around aperture 11*ai* with ends 14*ai* and 15*ai* fixed to the slightly adhesive top side of the disc-shaped section 1*ai*.

FIG. 189 shows how protective films 41*ai* and 43*ai* have been removed, after which aperture 11*ai* with cylinder 12*ai* has been pulled as closely as possible over the skin tag 21*ai* and section has been stuck to the skin 20*ai*.

In FIG. 190, the both ends 14*ai* and 15*ai* of the thread have been pulled in opposite directions around the cylinder 12*ai* and skin tag 21*ai*, the base of which is occluded. The occlusion is completed by a simple knot 16*ai*, after which the remaining thread ends 14*ai* and 15*ai* are stuck on the slightly adhesive top side of section 1*ai*.

FIG. 191 shows how section 3*ai* is pushed against section 1*ai* located on the skin 20*ai* such that the edges 13*ai* and 31*ai* snap together and lock sections 1*ai* and 3*ai* together concealing and fixing the occluded skin tag 21*ai* to the skin surface 20*ai*.

Example 34

This is another variant of Example 32 where the occlusion of skin tag 21*aj* is achieved by winding one or several threads around the base, where each thread is fixed to the small, upright, hard pins with a more or less adhesive surface.

FIG. 192 shows as FIG. 187 a low cylinder-shaped lid 3*aj* with an outwardly directed groove 31*aj* around the free edge.

The other section of the device, according to the invention is shown in FIG. 193, where the more or less hard and flexible, disc-shaped section 1*aj* has an adhesive underside covered by protective films 41*aj* and 43*aj*, a slit line 431*aj*, a central aperture 11*aj*, and a reinforced ring 12*aj* extending around the periphery, on which the reversed cone-shaped small pins 17*aj* and 19*aj* and the cylinder-shaped pins 16*aj* and 18*aj* are located, all of which have an adhesive surface. The outer peripheral edge is formed by a circular, inwardly directed groove 13*aj*. A mono- or multifilament thread is fixed to pin 16*aj*, said thread being placed as a tangle behind pin 17*aj* which is then pulled behind 18*aj*, where the flap 15*aj* is centrally placed for easy handling.

In FIG. 194, protective films 41*aj* and 43*aj* have been removed and section 1*aj* has been stuck to the skin 20*aj* such that skin tag 21*aj* sticks up through aperture 11*aj*.

FIG. 195 shows how the base of the skin tag 21*aj* is occluded by pulling the thread from 16*aj* once around the base of the skin tag 21*aj* to 17*aj* and back to the skin tag 21*aj* and once around the base and then to 18*aj*, and then back again and once around the base of the skin tag 21*aj*, and then to 19*aj*, and then once again around the skin tag 21*aj*; finally making a U-turn around 16*aj*, and winding it one last time around skin tag 21*aj* before passing 18*aj* and placing the flap on the disc 1*aj*.

As described in FIG. 196, section 3*aj* is then pushed towards section 1*aj* until grooves 13*aj* and 31*aj* lock into each other fixing and protecting the occluded skin tag 21*aj* on the skin surface 20*aj*.

Example 35

This Example is a third variant of Example 32 where the occlusion is achieved by preparing knots or ties which in a simple manner can be tightened at the base of the skin tag.

FIG. 197 is an overview of a band-shaped, more or less elastic and flexible device according to the invention, consisting of a central section 1*aq* with an adhesive underside covered by protective film 41*aq* and a more or less adhesive upper side and a centrally located aperture, 11*aq*. On each side of section 1*aq* are two similar free-standing sections 3*aq* and 5*aq* each with an adhesive upper side covered by protective films 43*aq* and 45*aq*, each with removal flaps 431*aq* and 451*aq*. The free-standing section 3*aq* is connected with section 1*aq*, while thread 12*aq*, stuck under protective film 43*aq* in section 3*aq*, on the slightly adhesive surface of section 1*aq* extends to thread 13*aq* from section 5*aq* in knot 1 or tie 4*aq*. The thread 12*aq* runs around knot 14*aq* into a strap on the other side of the aperture 11*aq* across section 1*aq* to knot 17*aq* and back to section 3*aq*, as thread 16*aq*, which through strap 126*aq* unites with thread 12*aq* in a closed loop. In the same way, threads 13*aq*, 135*aq* and 15*aq* are created, which are stuck to section 5*aq* under protective film 45*aq* together with knots 14*aq* and 17*aq* and the strap on the other side of the aperture 11*aq* on the slightly adhesive surface of section 1*aq*, similar to a closed loop. Along the sides section 1*aq* facing sections 3*aq* and 5*aq* are two narrow reinforcing bands 18*aq* and 19*aq*, each of which has two non-adhesive channels 181*aq* and 182*aq*, or 191*aq* and 192*aq* respectively, in order to ensure that the two loops tied into each other do not get entangled during storage or later usage.

FIG. 198 is a longitudinal section of FIG. 197 along the line CllC-CllC and shows the central section 1*aq* with aperture 11*aq* and reinforcing bands 18*aq* and 19*aq*, and the adhesive underside with protective film 41*aq*. From FIG. 198, it is possible to see that position of sections 3*aq* and 5*aq* with their adhesive upper sides covered by protective films 43*aq* and 45*aq* and the cut threads of both loops 126*aq* and 135*aq*.

FIG. 199 is perspective view of FIG. 197, where protective film 41*aq* has been removed and section 1*aq* has been stuck to the skin surface 20*aq* in such a manner that skin tag 21*aq* sticks up through the aperture 11*aq*. From FIG. 199, it is also possible to see that a loop is created by the two knots 14*aq* and 17*aq* and the straps 126*aq* and 135*aq* on the opposite side of the aperture 11*aq*, which is extending around the base of the skin tag 21*aq* at the surface of section 1*aq*.

In FIG. 200, sections 3*aq* and 5*aq* have been drawn out from section 1*aq* using the thumb and forefinger as indicated by the activity arrows, 31*aq* and 51*aq*, whereupon threads 12*aq*, 16*aq*, 126*aq*, 13*aq*, 15*aq* and 135*aq* stretch knots 14*aq* and 17*aq*, by passing 181*aq* and 182*aq*, 191*aq* and 192*aq* in reinforcing bands, 18*aq* and 19*aq*, which results in the loop around the base of skin tag 21*aq* being contracted.

FIG. 201 shows how sections 3*aq* and 5*aq* in FIG. 200 has been pulled as long out that the knots are contracted and occlude the base of the skin tag 21*aq* and how the stretched threads, 12*aq*, 13*aq*, 15*aq* and 16*aq* are stuck to the more or less adhesive upper side of section 1*aq*, after which protective films 43*aq* and 45*aq* are removed using removal flaps 431*aq* and 435*aq* and sections 3*aq* and 5*aq* are turned 180 degrees as indicated by the activity arrows 32*aq* and 52*aq* and stuck on top of section 1*aq*, upon which the occluded skin tag 21*aq* is fixed and concealed to the skin surface 20*aq*.

Example 36

In this example, the skin tag is occluded using a more or less hard screw arrangement that is stuck on the skin.

FIG. 202 shows the one section of the device, which forms an externally threaded, solid or hollow screw 3*ak* of metal, polymer or natural material with a head 32*ak* and at the other end of the screw, a cone 31*ak* which is placed in such a manner that the screw 3*ak* and cone 31*ak* can rotate independently of each other.

The other section 1*ak* of the device is shown in FIG. 203 and consists of a block of metal, polymer or natural material with an internal thread 13*ak*, an lumen 12*ak* corresponding to the thread, and a centrally placed aperture 11*ak* under the thread 13*ak*. The block 1*ak* has an adhesive under side 14*ak* which is covered by protective film 41*ak* with slit line 411*ak*, facilitating removal of protective film 41*ak*.

FIG. 204 is a cross section of FIG. 203 along line CCIV-CCIV showing block 1*ak* with aperture 12*ak* and the internal thread 13*ak*. Through the adhesive underside 14*ak*, there is an aperture 11*ak*, in the back wall of which is a flexible band 15*ak*. The aperture 11*ak* and the adhesive under side 14*ak* are covered by protective film 41*ak*.

FIG. 205 shows a semi-rigid band 5*ak* with an adhesive underside covered by protective film 45*ak*.

FIG. 206 is a side elevational view, showing how screw 3*ak* is screwed a few turns into thread 13*ak* with head 32*ak*.

In FIG. 207, the protective film 41*ak* has been removed and the device according to FIG. 206 has been stuck to the skin 20*ak* with skin tag 21*ak* as near the back wall 15*ak* of the aperture 11*ak* as possible.

In FIG. 208, the screw 3*ak* has been screwed into the internal thread 13*ak* in block 1*ak* with head 32*ak* until the cone 31*ak* compresses the skin tag 21*ak* against the band 15*ak*, thus occluding the base. Finally, the protective film 45*ak* is removed and the band 5*ak* is stuck to the upper side of block 1*ak*, whereby the screw 32*ak* is locked into position, fixing and concealing skin tag 21*ak* on the skin surface 20*ak*.

Example 37

This device according to the invention consists of a free-standing clip of metal, polymer or natural material, the elastic qualities of which occlude the stalk of the skin tag. The clip is mounted on two plaster-like sections which are fixed to the skin surface; an additional section conceals and fixates the skin tag to the clip on the skin.

FIG. 209 is a perspective view showing a parallel epipedic clip 1*al* of elastic metal, polymer or natural material, where one of the short sides is formed by a tongue 14*al* which is divided longitudinally into two parts 12*al* and 13*al* which are bent into the parallelepiped and where the other short side 15*al* forms an elastic counterpart between the long sides 16*al* and 17*al* of the clip. Under section 1*al*, there is a more or less elastic and flexible section 3*al* where the adhesive upper side sticks to the clip 1*al*, and where the adhesive underside is covered by protective film 43*al*. Under the clip 1*al*, section 3*al* pass into a new section 5*al*, the upper side of which is adhesive and the adhesive underside of which is protected by the two double-folded protective films 451*al* and 452*al*, or 453*al* and 454*al*, respectively, in the middle of the section there is a aperture 11*al*.

FIG. 210 is an overview of FIG. 209 where the inwardly directed tongue 14*al* with its two legs 12*al* and 14*al* is located in the middle of legs 16*al* and 17*al* and in the middle of the central aperture 11*al* in section 5*al*.

In FIG. 211, which is an overview, protective film 3*al* has been removed in FIG. 210 and the two legs 16*al* and 17 have been squeezed together so that skin tag 21*al* can pass through the open crossed legs 12*al* and 13*al* before section 3*al* is stuck to the skin surface 20*al*.

FIG. 212 shows how the two protective films 451 and 452, 453 and 454, respectively, in FIG. 211 have been removed, and legs 16*al* and 17*al* have sprung back with the help of the short side 15*al* such that the skin tag 21*al* is squeezed between the tongues 12*al* and 13*al* in the clip 1*al*.

FIG. 213 is an overview of FIG. 212 where the skin tag 21*al* has been occluded between the legs 12*al* and 13*al* in section 1*al* in the aperture 11*al* on the skin surface 20*al*.

FIG. 214 is a cross section along the line CCXIV-CCXIV in FIG. 213 showing section 1*al* and the double occlusion of the skin tag, 21*al*, which has been produced by the interaction between legs 12*al* and 13*al* and by pushing legs 16*al* and 17*al* down on the adhesive upper surface of section 5*al* which is stuck to the skin 20*al*.

FIG. 215 is an overview of a thin, band-shaped, flexible, more or less elastic section 6*al* with an adhesive side covered by protective film 46*al* with removal flap 461*al*.

FIG. 216 is the same cross section as in FIG. 214, where the free-standing section 6*al* has been applied on top of the parallelepipedic clip, 1*al*, whereby the occluded skin tag 21*al* is concealed and fixed within section 1*al*.

Example 38

This Example is a variant of Example 37 where the clip is in the form of an eight with two elastic legs and an uneven, adhesive, lower side and is covered after the occlusion of the skin tag by a large covering and fixating device on the skin surface.

FIG. 217 is a perspective view of an elastic section made of metal, polymer or natural material, which is in the form of an eight with two large, resilient, sector-formed sides 14*am* and 15*am* between which a narrow, asymmetrically arranged side 13*am* and a broad side 12*am* are extending, said broad side has a notch 17*am*, in which the smaller side 13*am* can expand. One edge of sides 14*am*, 12*am* and 15*am* in section 1*am* has a rim 16*am*, the outside of which is adhesive and covered by protective film 41*am*.

In FIG. 218, the protective paper 41*am* has been removed and sides 14*am* and 15*am* have been clamped between the thumb and forefinger, whereby side 13*am* extends into the notch 17*am* so that an aperture 11*am* can be created.

In FIG. 219, the device 1*am* with aperture 11*am* in FIG. 218 is pulled over skin tag 21*am* and placed on the skin. The resilient sides 14*am* and 15*am* spring back and sides 12*am* and 13*am* occlude the skin tag 21*am* at the same time as rim 16*am* sticks section 1*am* to the skin.

FIG. 220 is an overview showing a thin, more or less flexible and elastic section 3*am* with two pairs of opposite, similar flaps 32*am* and 35*am* respectively 31*am* and 33*am*. Section 3*am* has an adhesive side, covered by protective film 43*am* with slit line 431*am* which facilitates removal of the protective film 43*am*.

In FIG. 221, section 3*am* is stuck on top of the section 1*am* so that the occluded skin tag 21*am* is bent down and concealed, and the whole section 1*am* is stabilised by the flaps 31*am*, 32*am*, 33*am* and 34*am* which are bent down on the skin surface.

Example 39

The occlusion of the skin tag takes place via a single flexible, more or less elastic strap which is stretched around the edge of a small disc placed on the skin.

FIG. 222 is a perspective view of the device according to the invention, consisting of a section in form of a more or less hard, small disc 1*an* with an adhesive underside 3*an*, covered by a protective film 41*an*. Section 1*an* has a rounded edge 11*an* and a more or less flexible and elastic strap 13*an* which is stuck in the edge of the disc 1*an* with attachment 14*an*. As a lock for the strap, there is a hook or a cleat 12*an*.

In FIG. 223, the protective film 41*an* in FIG. 222 is removed and section 1*an* is stuck to the skin 20*an* as near the base skin tag 21 as possible.

FIG. 224 shows how the more or less flexible and elastic strap 13*an* is pulled around skin tag 21*an*, occluding the base against to the rounded edge 11*an*, after which the strap 13*an* is locked to the hook 12*an* in section 1*an*.

FIG. 225 shows a thin, more or less elastic section 5*an* with an adhesive side covered by protective film 45*an*.

In FIG. 226 the protective film 45*an* in FIG. 225 has been removed, and section 5*an* has been stuck on top of section 1*an* and over the edge of section 1*an* and onto the skin 20*an* to conceal and fix the occluded skin tag 21*an* to the skin surface in the best way possible.

Example 40

This is a variant of Example 39, where the occluded part is located between the device and a movable arm or lifting rod on the device, which can be locked and produce an optimal occlusive effect.

FIG. 227 is a frontal view showing a device 1*ao* consisting of a more or less hard, preferably quadratic, thin disc, one edge of which is rounded 10*ao* and n the upper side of which there is a movable arm or lifting rod 12*ao* which in an open position is fixated by lock 14*ao* and the underside of which has an adhesive layer 15*ao* covered by protective film 41*ao*. On the upper side of the device is an additional lock 13*ao* which locks the arm or lifting rod 12*ao* in an occlusive position. Between the arm or lifting rod 12*ao* and the hook or cleat 11*ao* positioned on one side of the preferably quadratic disc 1*a*0 is a more or less flexible and elastic strap 16*ao*.

FIG. 228 is an overview of FIG. 227, showing how the more or less flexible and elastic strap 16*ao* is placed suspended between the cleat or hook 11*ao* and the arm or lifting rod 12*ao* retained on the upper side, which can be turned 90 degrees over the rounded edge 10*ao* to a new position 17*ao* and fixed there by lock 13*ao*.

FIG. 229 is a perspective view of FIG. 227, where the positions of the locks 13*ao* and 14*ao* and the strap 16*ao* located between the hook or cleat 11*ao* and the arm 12*ao* on the device 1*ao* are shown. The adhesive layer 15*ao* and the protective film 41*ao* of the device 1*ao* are also shown.

In FIG. 230, which is an overview, the protective film 41*ao* has been removed and the device 1*ao* is stuck to the skin 20*ao* with skin tag 21*ao* placed between the arm 12*ao* and the strap 16*a*.

FIG. 231 shows a more or less hard, quadratic box-formed section 3*ao* with an open underside, above which are located four control heels 31*ao*, 32*ao*, 33*ao*, and 34*ao* on two opposite sides.

In FIG. 232, section 3*ao* in FIG. 231 has been pulled over the device 1*ao* stuck to the skin with the skin tag 21*ao* occluded by strap 16*ao* so that the control heels 31*ao* and 32*ao* are locked against 12*ao* and control heels 33*ao* and 34*ao* are locked against 11*ao*, which fixes section 3*ao* on the device 1*ao*. The occluded skin tag 21*ao* is then concealed and stabilised on the skin surface 20*ao*.

Example 41

In this example of the invention, the skin tag is squeezed between two common sides in two triangular, inverted sections which are kept together by a common edge.

FIG. 233 is a perspective view of a section of metal, polymer or natural material according to the invention, which consists of two triangular, more or less more rigid sections with sides 11*ar*, 12*ar*, 13*ar* and 3*ar* with sides 31*ar*, 32*ar* and 33*ar*. Sides 12*ar* and 32*ar* have an adhesive outer side covered by protective film 412*ar* and 432*ar* and each have a notch 121*ar* and 231*ar* at the edges of the sides 13*ar* and 33*ar*. Sides 13*ar* and 33*ar* each have a large central hole 132*ar* and 332*ar* which is enclosed by a frame which is adhesive on the outer side and has a narrow section 131*ar* or 331*ar* and is covered by a protective film 413*ar* or 433*ar*. The sides are united along the shared edge of fold 5*ar* around which the two triangular sections 1*ar* and 3*ar* can be turned.

In FIG. 234, which is a perspective view of FIG. 233, the protective film 412*ar* has been removed and area 12*ar* on section 1*ar* in FIG. 245 has been stuck to the skin 20*ar* with skin tag 21*ar* in the middle in front of the thin frame section, 131*ar*, after which the protective film 413 is removed.

In FIG. 235 which is a perspective view, the protective film 433 has been removed from the surface 33 and section 3*ar* in FIG. 234 has been twisted around the fold 5*ar* into a horizontal position.

FIG. 236 shows how protective film 432*ar* is removed from surface 32*ar* before section 3 is twisted down towards the skin surface 20*ar* using fold 5*ar* so that the adhesive frame of sides 13*ar* and 33*ar* have been stuck together, including frame sections 131*ar* and 331*ar* which then press against the base of the skin tag 21*ar* each from their own side, and expand outwards into notches 121*ar* and 321*ar* during the occlusion of the blood flow in the proximal part of the skin tag 21*ar*. At the same time, area 32 is stuck to the skin, which further stabilises and conceals the skin tag 21*ar* on the skin surface 20*ar* and facilitates removal of the skin tag from the skin surface after the natural constriction effect.

Example 42

In this example of the invention the central, occluding, more or less hard sections are encircled by a thin, elastic film which levels the occluding edges against each other.

FIG. 237 is a perspective view of a device according to the invention, where the more or less hard and flexible sections 1*ap* and 3*ap* on both sides are surrounded by a thin, elastic film 11*ap* and 31*ap*. Between the sections 1*ap* and 3*ap* is a very narrow slot 13*ap* and a corresponding slit through the thin, elastic films. The underside of the device is adhesive and the underside of both sections 1*ap* and 3*ap* is covered by protective films 41*ap* and 43*ap*.

FIG. 238 is a cross section along the line CCXXXVIII-CCXXXVIII in FIG. 237 and shows the design of the thin, laminated device, where the sections 1*ap* and 3*ap* on both sides are surrounded by the elastic film 11*ap* respectively 31*ap* which retain and centres both sections of the device outside the slit 13*ap*. Outside the elastic films 11*ap* and 31*ap* on the underside of the device, a layer 12*ap* and 32*ap* is located, which is adhesive on both sides and on which an additional, thin layer 14*ap* and 34*ap* with moisture-absorbent and moisture-conveying properties is adhered. On the other side of the moisture-absorbent and moisture-conveying layers 14*ap* and 34*ap* is an additional layer 12*ap* and 34*ap* which is adhesive on both sides. Both adhesive undersides of the sections 1*ap* and 3*ap* are finally covered by protective films 41*ap* and 43*ap*.

FIG. 239 is an overview of a thin, more or less transparent film 5*ap* which is stabilised by protective film 451*ap* and the adhesive underside of which is covered by protective film 452*ap*.

In FIG. 240, protective film 41*ap* has been removed and slit 13*ap* has been extended to a parallelepipedic aperture which is pulled over skin tag 21*ap* so that the slit edge on section 1*ap* abuts the base of skin tag 21*ap*, after which section 1*ap* is stuck to the skin surface 20*ap*.

FIG. 241 shows how protective film 43*ap* is removed from section 3*ap* and how the other edge of slit 13*ap* is guided and pressed against the other side of the base of skin tag 21*ap* by means of the elastic film areas 11*ap* and 13*ap* located outside the slit, thereby occluding the skin tag. Subsequently, section 3*ap* is stuck on skin 20*ap*.

In FIG. 242, the protective film 452*ap* is removed from the underside of section 5*ap* which is then stuck on the upper side of the device which is located on the skin with the occluded skin tag 21*ap*. Finally, the protective film 451 is carefully removed from the upperside of section 5*ap*. As suitable polymers for the function of the device according to the invention, it can be mentioned that the thin, more or less hard and flexible core in Example 42 can be made of a thin polyethylene or polypropylene film or another polymer having the same properties which is of medical grade. The core in Example 42 is surrounded by a thin, elastic, polyurethane film, such as e.g., 3M 9842 or Opsite from Smith & Nephew.

As adhesives against the skin one of the bioinert adhesives 1510 or 1524 from 3M can advantageously be used.

What is claimed is:

1. A method for occlusive removal of a protruding skin tag from a skin area, the skin tag having an upper portion and a lower portion nearest the skin area, the method comprising:
    enclosing or enfolding the lower portion of the protruding skin tag nearest the skin area by an adhesion member,
    applying an occlusion pressure by a pressure member to the enclosed or enfolded lower portion of the skin tag, whereby sustained blood supply is occluded and necrosis of the skin tag is initiated,
    immobilizing the upper portion of the skin tag relative to the skin area with a locking member having adhesive for a period sufficient to allow release of the skin tag from the skin area, and
    removing the skin tag.

2. A method for occlusive removal of a protruding skin tag from a skin area, the skin tag having an upper portion and a lower portion nearest the skin area, the method comprising:
    enclosing or enfolding the lower portion of the protruding skin tag nearest the skin area,
    applying an occlusion pressure to the enclosed or enfolded lower portion of the skin tag, whereby sustained blood supply is occluded and necrosis of the skin tag is initiated,
    immobilizing the upper portion of the skin tag relative to the skin area with an adhesive for a period sufficient to allow release of the skin tag from the skin area, and
    removing the skin tag.

3. The method according to claim 2, wherein the adhesive adheres to the skin area.

4. The method according to claim 2, wherein the adhesive adheres to the skin tag.

5. A method for occlusion of a protruding skin tag on a skin area, the skin tag having an upper portion and a lower portion nearest the skin area, the method comprising:
    enclosing or enfolding the lower portion of the protruding skin tag nearest the skin area,
    applying an occlusion pressure to the enclosed or enfolded lower portion of the skin tag, whereby sustained blood supply is occluded for a period sufficient to initiate necrosis of the skin tag, and
    immobilizing the upper portion of the skin tag relative to the skin area with an adhesive.

6. The method according to claim 5, wherein the adhesive adheres to the skin area.

7. The method according to claim 5, wherein the adhesive adheres to the skin tag.

* * * * *